(12) United States Patent
Qian et al.

(10) Patent No.: US 11,613,545 B2
(45) Date of Patent: Mar. 28, 2023

(54) MACROCYCLIC COMPOUND SERVING AS WEE1 INHIBITOR AND APPLICATIONS THEREOF

(71) Applicant: WUXI BIOCITY BIOPHARMACEUTICS CO., LTD., Jiangsu (CN)

(72) Inventors: Wenyuan Qian, Shanghai (CN); Chundao Yang, Shanghai (CN); Zhengwei Li, Shanghai (CN); Jie Li, Shanghai (CN); Jian Li, Shanghai (CN); Shuhui Chen, Shanghai (CN)

(73) Assignee: WUXI BIOCITY BIOPHARMACEUTICS CO., LTD., Jiangsu (CN)

( * ) Notice: Subject to any disclaimer, the term of this patent is extended or adjusted under 35 U.S.C. 154(b) by 0 days.

(21) Appl. No.: 16/759,769

(22) PCT Filed: Oct. 31, 2018

(86) PCT No.: PCT/CN2018/112909
§ 371 (c)(1),
(2) Date: Apr. 28, 2020

(87) PCT Pub. No.: WO2019/085933
PCT Pub. Date: May 9, 2019

(65) Prior Publication Data
US 2020/0325145 A1 Oct. 15, 2020

(30) Foreign Application Priority Data

Nov. 1, 2017 (CN) .......................... 201711058653.5

(51) Int. Cl.
*C07D 487/14* (2006.01)
*A61P 35/04* (2006.01)
*C07D 519/00* (2006.01)

(52) U.S. Cl.
CPC .......... *C07D 487/14* (2013.01); *A61P 35/04* (2018.01); *C07D 519/00* (2013.01)

(58) Field of Classification Search
CPC .................................................. C07D 487/14
See application file for complete search history.

(56) References Cited

U.S. PATENT DOCUMENTS

| | | | |
|---|---|---|---|
| 7,834,019 B2 | 11/2010 | Sagara et al. | |
| 2005/0215556 A1 | 9/2005 | Lin et al. | |
| 2007/0254892 A1 | 11/2007 | Sagara et al. | |
| 2010/0063024 A1 | 3/2010 | Sakamoto et al. | |
| 2010/0221211 A1 | 9/2010 | Furuyama et al. | |
| 2011/0243891 A1 | 10/2011 | Bamba et al. | |
| 2012/0220572 A1 | 8/2012 | Tong et al. | |
| 2016/0122342 A1 | 5/2016 | Fosbenner et al. | |
| 2020/0377520 A1* | 12/2020 | Zhao ................... | C07D 471/04 |

FOREIGN PATENT DOCUMENTS

| | | |
|---|---|---|
| CN | 101432284 A | 5/2009 |
| CN | 2017110586535 | 11/2017 |
| CN | 108623615 A | 10/2018 |
| EP | 2213673 A1 | 8/2010 |
| EP | 3604306 A1 | 2/2020 |
| JP | 2012-511502 A | 5/2012 |
| JP | 2016-520645 A | 7/2016 |
| WO | WO-2007/126128 A1 | 11/2007 |
| WO | WO-2007126122 A1 | 11/2007 |
| WO | WO-2008133866 A1 | 11/2008 |
| WO | WO-2011034743 A1 | 3/2011 |
| WO | WO-2011049987 A2 | 4/2011 |
| WO | WO-2013012681 A1 | 1/2013 |
| WO | WO-2013013031 A1 | 1/2013 |
| WO | WO-2013059485 A1 | 4/2013 |
| WO | WO-2013126656 A1 | 8/2013 |
| WO | WO-2014167347 A1 | 10/2014 |

(Continued)

OTHER PUBLICATIONS

Office action dated Aug. 2, 2021 issued in counterpart Singapore application No. 11202003974X.
Office action dated Aug. 16, 2021 issued in counterpart Indian application No. 202027020882.
Jan. 12, 2021 Indian Office Action issued in Indian Patent Application No. 202027020882.
Jan. 17, 2019 International Search Report issued in International Patent Application No. PCT/CN2018/112909.
Jan. 17, 2019 Written Opinion of the International Searching Authority issued in International Patent Application No. PCT/CN2018/112909.

(Continued)

*Primary Examiner* — Susanna Moore
(74) *Attorney, Agent, or Firm* — Harness, Dickey & Pierce, P.L.C.

(57) ABSTRACT

Disclosed in the present invention are a macrocyclic compound serving as a Wee1 inhibitor, and applications thereof in the preparation of drugs for treating Wee1-related diseases. The present invention specifically relates to a compound represented by formula (II), an isomer thereof, and a pharmaceutically acceptable salt thereof.

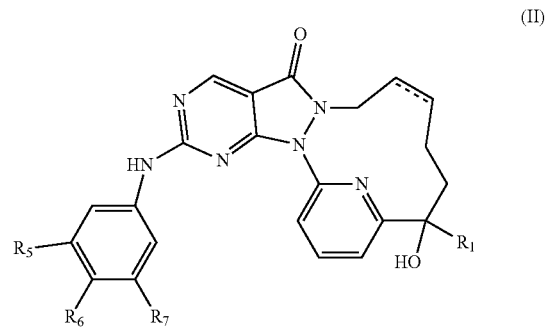

(II)

20 Claims, No Drawings
Specification includes a Sequence Listing.

(56) References Cited

FOREIGN PATENT DOCUMENTS

| | | |
|---|---|---|
| WO | WO-2015019037 A1 | 2/2015 |
| WO | WO-2015092431 A1 | 6/2015 |
| WO | WO-2017075629 A2 | 5/2017 |
| WO | WO-2018171633 A1 | 9/2018 |
| WO | WO-2020083404 A1 * | 4/2020 ............. A61K 31/55 |

OTHER PUBLICATIONS

Office action dated Nov. 30, 2021 issued in counterpart Russian application No. 2020117443.
Chinese Office Action regarding Application No. 201880071103.3, dated Mar. 9, 2022.
Second Russian Office Action regarding Application No. 2020117443, dated Apr. 21, 2022.
First Office Action issued in the counterpart Australian application No. 2018361010 dated Sep. 12, 2022.
First Office Action issued in the counterpart European application No. 18874492 dated Oct. 12, 2022.
May 17, 2022 Israel Office Action of Israel Patent application No. 274357.
First Office Action issued in the counterpart Japanese application No. 2020524447 dated Nov. 8, 2022.

* cited by examiner

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: polypeptide substrate

<400> SEQUENCE: 1

Leu Ser Asn Leu Tyr His Gln Gly Lys Phe Leu Gln Thr Phe Cys Gly
1               5                   10                  15

Ser Pro Leu Tyr Arg Arg Arg
            20
```

MACROCYCLIC COMPOUND SERVING AS WEE1 INHIBITOR AND APPLICATIONS THEREOF

CROSS-REFERENCE TO RELATED APPLICATIONS

This application is a 371 National Phase of International Application No. PCT/CN2018/112909, filed Oct. 31, 2018, which claims the benefit of Chinese Patent Application No. CN 201711058653.5, filed Nov. 1, 2017. The entire disclosures of the above applications are incorporated herein by reference.

REFERENCE TO A SEQUENCE LISTING SUBMITTED VIA EFS-WEB

The content of the ASCII text file of the sequence listing named "SEQUENCE LISTING" which is 997 bytes in size and was created on Jul. 22, 2022, and electronically submitted via EFS-Web is hereby incorporated by reference in its entirety.

FIELD OF THE INVENTION

The present invention relates to a macrocyclic compound, and a use thereof in the manufacture of a medicament for treating Wee1-related diseases, specifically relates to a compound represented by formula (II), an isomer thereof or a pharmaceutically acceptable salt thereof.

BACKGROUND OF THE INVENTION

The progress of the cell cycle is a complex process controlled by a series of cell cycle regulatory systems. The core component of the cell cycle regulatory systems is the CKDs/Cyclins complexes formed by the combination of cyclin-dependent kinases (CDKs) and Cyclins, which can promote the cell to enter the proliferation cycle, in which the CDK1 (human homologue, also known as CDC2)/Cyclin B complex plays a key role in controlling the cell to enter the M phase.

It is necessary to complete DNA replication before the cell enters the M phase. Due to the interference of various endogenous and exogenous factors, DNA will often be mutated or damaged. These abnormal DNA must be repaired, otherwise they will cause mitotic disaster and cell death. The main function of the cell cycle checkpoints is to suspend the cell cycle and allow the cell to complete DNA repair before entering the M phase. The G1/S checkpoint at the end of G1 phase and the G2/M checkpoint at G2 phase are the two main cell cycle checkpoints, which are responsible for the identification and repair of DNA damage. Normal cells can use the G1/S checkpoint to complete DNA repair in the G1 phase. However, nearly 50% of cancerous cells have the defect of the tumor suppressor gene p53, which makes them lack G1/S checkpoint function, so they need to rely more on G2/M checkpoint to complete DNA repair. G2/M checkpoint is rarely mutated. It is because of this that cancer cells can escape the treatment of DNA damage agents and radiation.

Wee1 protein kinase is a cell cycle regulator that belongs to the family of serine and threonine protein kinases in the nucleus and is a key kinase in the G2/M checkpoint. The human "Wee" protein kinase family mainly includes Wee1 and Myt1, which can phosphorylate the Tyr15 site of CDC2, inhibit the activation of CDC2/Cyclin B complex, and prevent cells from entering the M phase until DNA repair is completed. Myt1 can also phosphorylate the Thr14 site on CDC2, which is also a negative regulation of CDC2 activity. Wee1 kinase is highly expressed in many cancerous cells. By inhibiting Wee1 kinase, tumor cells can directly skip the DNA repair in G2 phase and enter mitosis in advance, leading to the death of tumor cells and achieving the purpose of treating cancer.

At present, a Wee1 inhibitor of AstraZeneca, AZD1775, has entered clinical phase II, and more than 30 clinical trials are under development, which have shown good therapeutic effects. AZD1775 was first developed by Merck, so it is also known as MK-1775. In September 2013, Merck transferred the compound to AstraZeneca worldwide, and the related patents mainly include US20070254892, WO2007126122, EP2213673, WO2008133866, WO2011034743 and so on. Abbott and Abbvie have also conducted research on Wee1 inhibitors, and related patents mainly include US2012220572, WO2013126656, WO2013012681, WO2013059485, WO2013013031, WO2013126656 and so on. Almac's patents on Wee1 inhibitors include WO2014167347, WO2015019037, and WO2015092431.

WO2008133866 discloses the compound AZD1775, the structure is as follows:

AZD1775

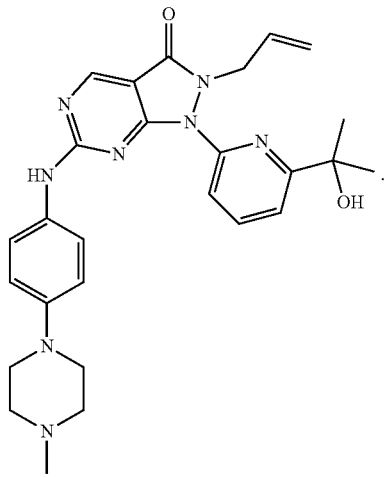

DETAILED DESCRIPTION OF THE PRESENT INVENTION

A compound represented by formula (II), an isomer thereof or a pharmaceutically acceptable salt thereof, (II)

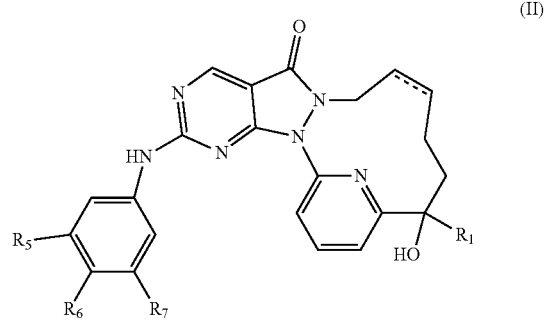

wherein,

⌇ is a single bond or a double bond;

$R_1$ is selected from H and $C_{1-3}$ alkyl, wherein the $C_{1-3}$ alkyl is optionally substituted by R, and the number of R is 1, 2 or 3;

$R_5$ is selected from H and $C_{1-3}$ alkyl, wherein the $C_{1-3}$ alkyl is optionally substituted by R, and the number of R is 1, 2 or 3;

$R_6$ is selected from $R_{61}$,

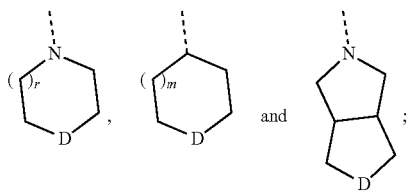

r is 1 or 2;
m is 1 or 2;
D is selected from —N($R_2$)—, —N$^+$(O$^-$)($R_2$)— and —C($R_3$)($R_4$)—;

$R_2$ is selected from H and $C_{1-3}$ alkyl, wherein the $C_{1-3}$ alkyl is optionally substituted by R, and the number of R is 1, 2 or 3;

$R_3$ and $R_4$ are independently selected from H, F, Cl, Br, I, OH, $NH_2$ and $C_{1-3}$ alkyl, wherein the $NH_2$ and the $C_{1-3}$ alkyl are optionally substituted by R, and the number of R is 1, 2 or 3;

alternatively, $R_3$ and $R_4$ together with the carbon atom to which they are attached form a 5-7 membered cycloalkyl or 5-7 membered heterocycloalkyl, wherein the 5-7 membered cycloalkyl and 5-7 membered heterocycloalkyl are optionally substituted by R, and the number of R is 1, 2 or 3;

$R_{61}$ is selected from H, F, Cl, Br, I, OH, $NH_2$, $C_{1-3}$ alkoxy and —O—$C_{3-6}$ cycloalkyl, wherein the $C_{1-3}$ alkoxy and the —O—$C_{3-6}$ cycloalkyl are optionally substituted by R, and the number of R is 1, 2 or 3;

$R_7$ is selected from H, F, Cl, Br, I, OH, $NH_2$, $C_{1-3}$ alkyl, $C_{1-3}$ alkoxy and 5-6 membered heterocycloalkyl, wherein the $C_{1-3}$ alkyl, $C_{1-3}$ alkoxy and 5-6 membered heterocycloalkyl are optionally substituted by R, and the number of R is 1, 2 or 3;

alternatively, $R_6$ and $R_7$ together with the ring atoms to which they are attached form ring A, and the ring A is selected from 5-7 membered heterocycloalkyl which is optionally substituted by R, and the number of R is 1, 2 or 3;

R is independently selected from F, Cl, Br, I, OH, $NH_2$, $C_{1-3}$ alkyl, $C_{1-3}$ alkoxy and $C_{1-3}$ alkylamino;

the 5-7 membered heterocycloalkyl contains 1, 2, 3 or 4 heteroatoms or heteroatom groups independently selected from —NH—, —S— and N.

In some embodiments of the present invention, the R is independently selected from F, Cl, Br, I, OH, $NH_2$, $CH_3$, Et, —$OCH_3$ and

and other variables are as defined in the present invention.

In some embodiments of the present invention, the $R_1$ is selected from H, $CH_3$ and Et, and other variables are as defined in the present invention.

In some embodiments of the present invention, the $R_2$ is selected from H, $CH_3$ and Et, and other variables are as defined in the present invention.

In some embodiments of the present invention, the $R_3$ and $R_4$ are independently selected from H, F, Cl, Br, I, OH, $NH_2$, —NH($CH_3$), —N($CH_3$)$_2$, $CH_3$ and Et, and other variables are as defined in the present invention.

In some embodiments of the present invention, the $R_3$ is selected from H, F, Cl, Br, I, OH, $NH_2$, —NH($CH_3$), —N($CH_3$)$_2$, $CH_3$ and Et, and other variables are as defined in the present invention.

In some embodiments of the present invention, the $R_4$ is selected from H, F, Cl, Br, I, OH, $CH_3$ and Et, and other variables are as defined in the present invention.

In some embodiments of the present invention, the $R_5$ is selected from H, $CH_3$ and Et, wherein the $CH_3$ and Et are optionally substituted by R, and the number of R is 1, 2 or 3; and other variables are as defined in the present invention.

In some embodiments of the present invention, the $R_5$ is selected from H, $CH_3$ and —$CH_2OH$, and other variables are as defined in the present invention.

In some embodiments of the present invention, the $R_{61}$ is selected from H, F, Cl, Br, I, OH, $NH_2$, —$OCH_3$,

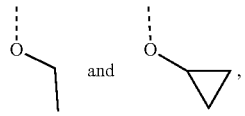

wherein the —$OCH_3$,

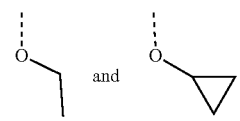

are optionally substituted by R, and the number of R is 1, 2 or 3; and other variables are as defined in the present invention.

In some embodiments of the present invention, the $R_{61}$ is selected from H, F, Cl, Br, I, OH, $NH_2$, —$OCH_3$,

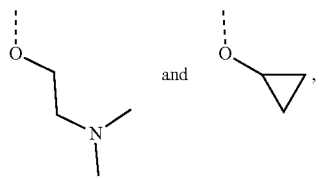

and other variables are as defined in the present invention.

In some embodiments of the present invention, the $R_6$ is selected from $R_{61}$,

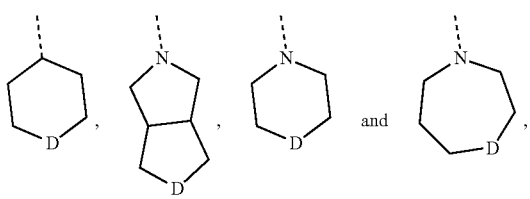

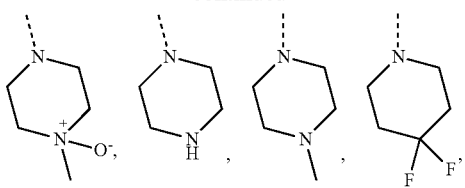

and other variables are as defined in the present invention.

In some embodiments of the present invention, the $R_6$ is selected from $R_{61}$,

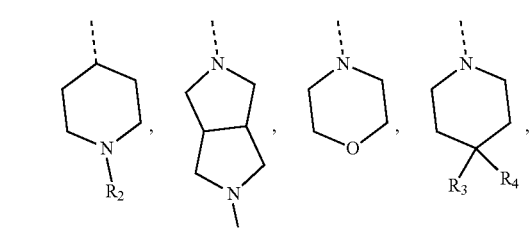

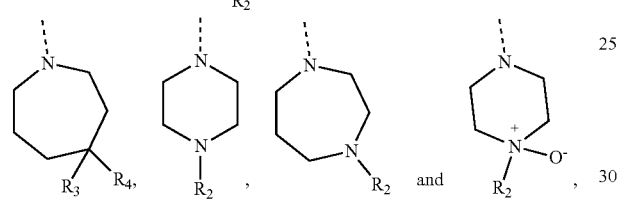

and other variables are as defined in the present invention.

In some embodiments of the present invention, the $R_3$ and $R_4$ together with the carbon atom to which they are attached form a 5-7 membered cycloalkyl or 5-7 membered heterocycloalkyl, the 5-7 membered cycloalkyl or 5-7 membered heterocycloalkyl is optionally substituted by R, and the number of R is 1, 2 or 3; then the moiety

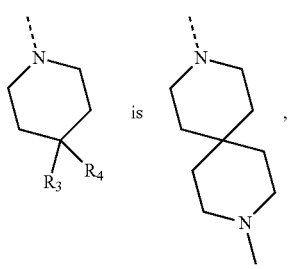

and other variables are as defined in the present invention.

In some embodiments of the present invention, the $R_6$ is selected from H, F, Cl, Br, I, OH, $NH_2$, $-OCH_3$,

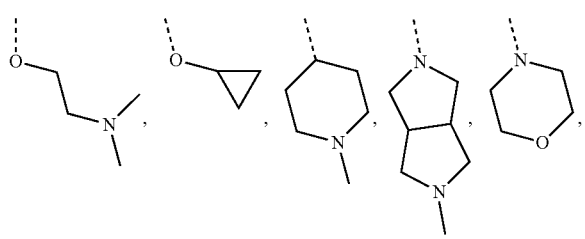

and other variables are as defined in the present invention.

In some embodiments of the present invention, the $R_7$ is selected from H, F, Cl, Br, I, OH, $NH_2$, $CH_3$, $-OCH_3$,

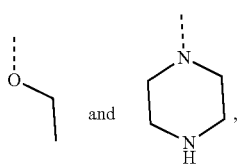

wherein the $CH_3$, $-OCH_3$,

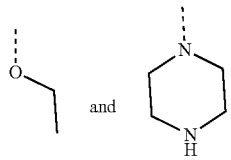

are optional substituted by R, and the number of R is 1, 2, or 3; and other variables are as defined in the present invention.

In some embodiments of the present invention, the $R_7$ is selected from H, F, Cl, Br, I, OH, $NH_2$, $CH_3$, $-OCH_3$,

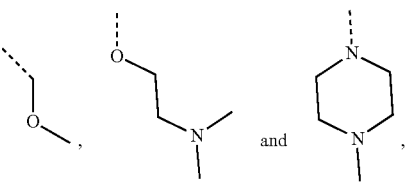

and other variables are as defined in the present invention.

In some embodiments of the present invention, the ring A is selected from piperidyl which is optionally substituted by R, and the number of R is 1, 2 or 3, and other variables are as defined in the present invention.

In some embodiments of the present invention, the moiety

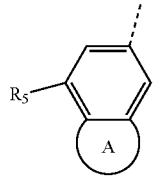

is

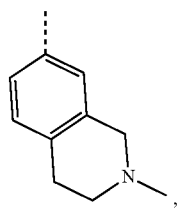

and other variables are as defined in the present invention.

In some embodiments of the present invention, the moiety

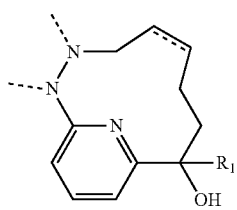

is selected from

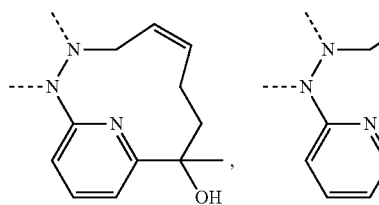

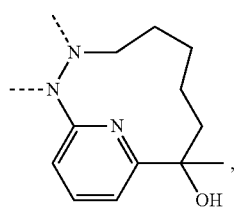

and other variables are as defined in the present invention.

In some embodiments of the present invention, the compound, the isomer thereof or the pharmaceutically acceptable salt thereof is selected from

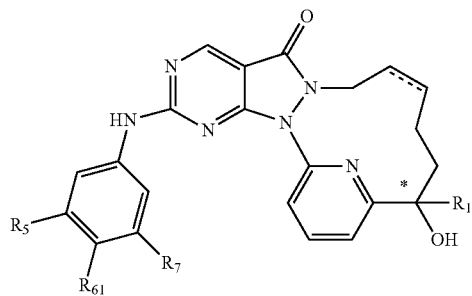
(II-1)

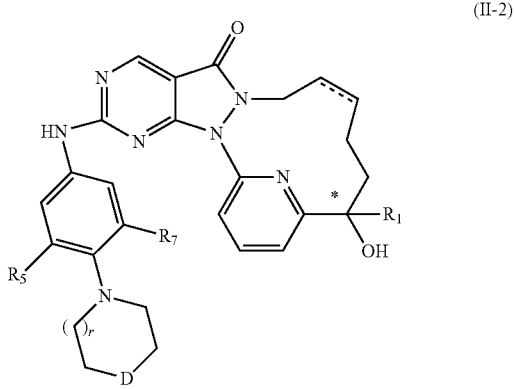
(II-2)

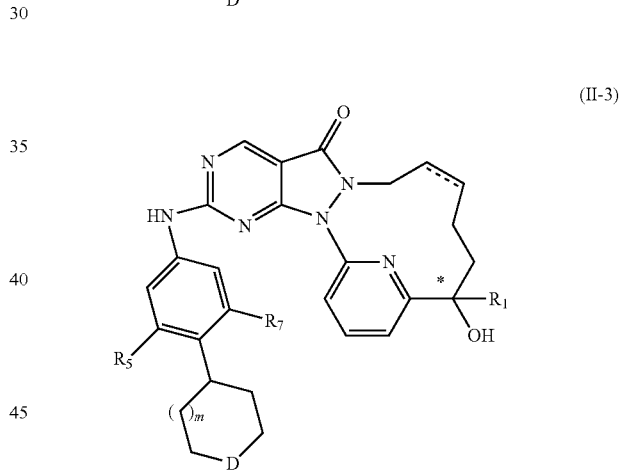
(II-3)

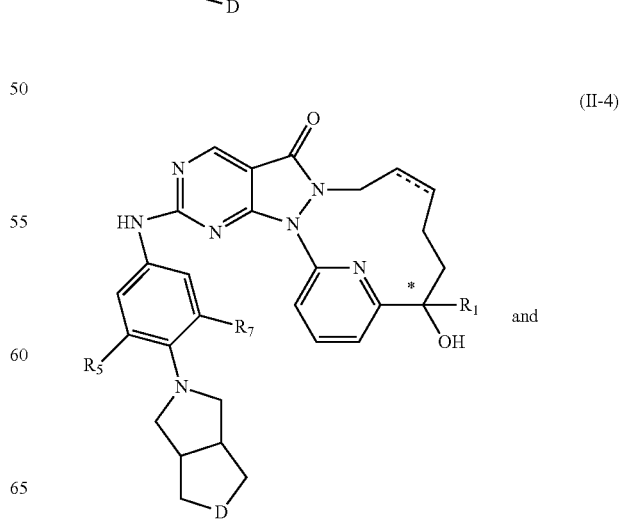
(II-4)

and

-continued (II-5)

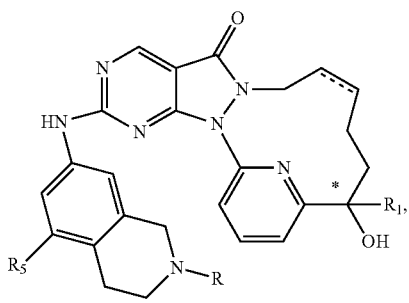

wherein,

D is selected from —N(R$_2$)—, —N$^+$(O$^-$)(R$_2$)— and —C(R$_3$)(R$_4$)—;

r, m, R$_1$, R$_2$, R$_3$, R$_4$, R$_5$, R$_{61}$ and R$_7$ are as defined in the present invention;

the carbon atom with "*" is a chiral carbon atom and exists in the form of (R) or (S) single enantiomer or enriched in one enantiomer.

In some embodiments of the present invention, the compound, the isomer thereof or the pharmaceutically acceptable salt thereof is selected from (I)

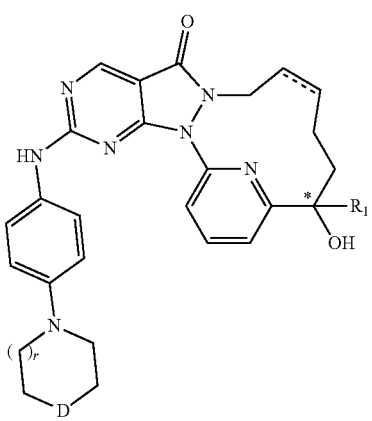

wherein,

D is selected from —N(R$_2$)—, —N$^+$(O$^-$)(R$_2$)— and —C(R$_3$)(R$_4$)—;

r, R$_1$, R$_2$, R$_3$, R$_4$ are as defined in the present invention;

the carbon atom with "*" is a chiral carbon atom and exists in the form of (R) or (S) single enantiomer or enriched in one enantiomer.

In some embodiments of the present invention, the moiety

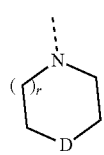

is selected from

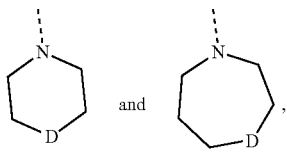

and other variables are as defined in the present invention.

The present invention provides a compound represented by formula (I), an isomer thereof or a pharmaceutically acceptable salt thereof, (I)

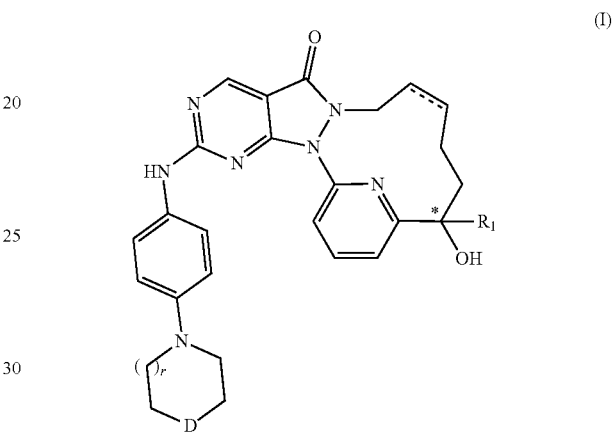

wherein,

⇌ is a single bond or a double bond;

r is 1 or 2;

D is selected from —N(R$_2$)— and —C(R$_3$)(R$_4$)—;

R$_1$ is selected from H and C$_{1-3}$ alkyl, wherein the C$_{1-3}$ alkyl is optionally substituted by R, and the number of R is 1, 2 or 3;

R$_2$ is selected from H and C$_{1-3}$ alkyl, wherein the C$_{1-3}$ alkyl is optionally substituted by R, and the number of R is 1, 2 or 3;

R$_3$ and R$_4$ are independently selected from H, F, Cl, Br, I, OH, NH$_2$ and C$_{1-3}$ alkyl, wherein the NH$_2$ or the C$_{1-3}$ alkyl is optionally substituted by R, and the number of R is 1, 2 or 3;

alternatively, R$_3$ and R$_4$ are connected to form a 5-7 membered cycloalkyl or heterocycloalkyl, the 5-7 membered cycloalkyl and heterocycloalkyl are optionally substituted by R, and the number of R is 1, 2 or 3;

R is independently selected from F, Cl, Br, I, OH, NH$_2$ and C$_{1-3}$ alkyl;

the 5-7 membered heterocycloalkyl contains 1, 2, 3 or 4 heteroatoms or heteroatom groups independently selected from —NH—, —S— and N;

the carbon atom with "*" is a chiral carbon atom and exists in the form of (R) or (S) single enantiomer or enriched in one enantiomer.

In some embodiments of the present invention, the R is independently selected from F, Cl, Br, I, OH, NH$_2$, CH$_3$ and Et, and other variables are as defined in the present invention.

In some embodiments of the present invention, the R$_1$ is selected from H, CH$_3$ and Et, and other variables are as defined in the present invention.

In some embodiments of the present invention, the R$_2$ is selected from H, CH$_3$ and Et, and other variables are as defined in the present invention.

In some embodiments of the present invention, the R$_3$ and R$_4$ are independently selected from H, F, Cl, Br, I, OH, NH$_2$, —NH(CH$_3$), —N(CH$_3$)$_2$, CH$_3$ and Et, and other variables are as defined in the present invention.

In some embodiments of the present invention, the R$_3$ is selected from H, F, Cl, Br, I, OH, NH$_2$, —NH(CH$_3$), —N(CH$_3$)$_2$, CH$_3$ and Et, and other variables are as defined in the present invention.

In some embodiments of the present invention, the R$_4$ is selected from H, F, Cl, Br, I, OH, CH$_3$ and Et, and other variables are as defined in the present invention.

In some embodiments of the present invention, the moiety

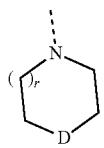

is selected from

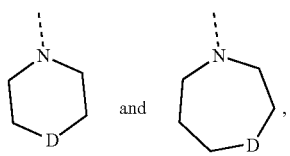

and other variables are as defined in the present invention.

In some embodiments of the present invention, the moiety

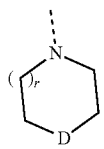

is selected from

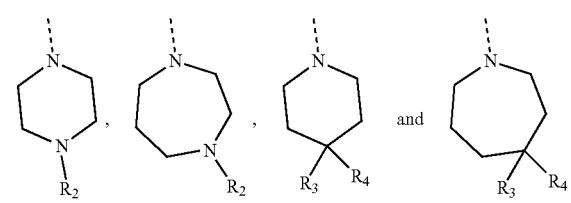

and other variables are as defined in the present invention.

In some embodiments of the present invention, the R$_3$ and R$_4$ are connected to form a 5-7 membered cycloalkyl or heterocycloalkyl, the 5-7 membered cycloalkyl or heterocycloalkyl is optionally substituted by R, and the number of R is 1, 2 or 3; then the moiety

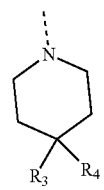

is

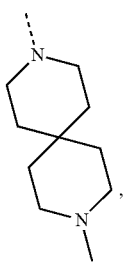

and other variables are as defined in the present invention.

In some embodiments of the present invention, the moiety

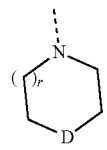

is selected from

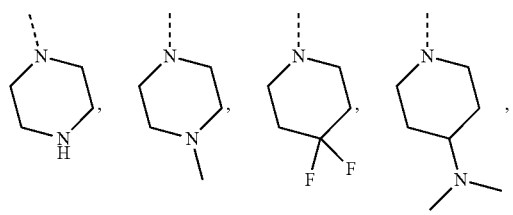

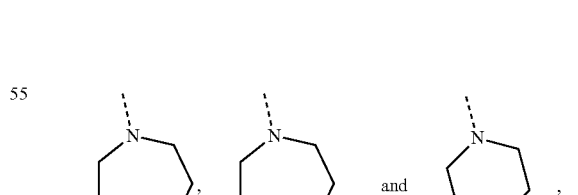

and other variables are as defined in the present invention.

In some embodiments of the present invention, the moiety

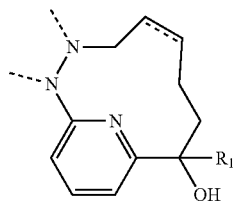

is selected from

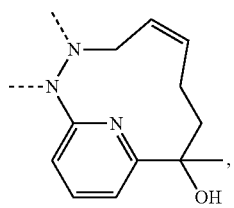 , 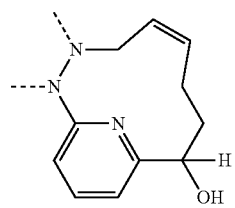 and

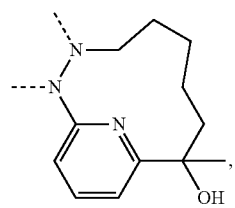 , and other variables are as defined in the present invention.

Some embodiments of the invention are derived from any combination of the above variables.

In some embodiments of the present invention, the compound, the isomer thereof or the pharmaceutically acceptable salt thereof is selected from

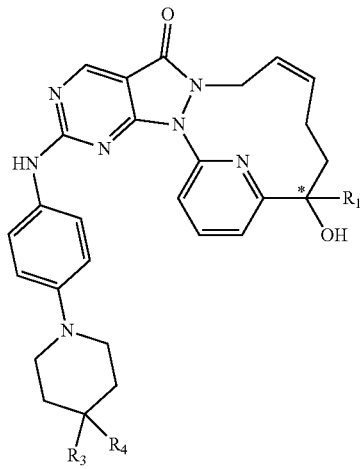

(I-1)

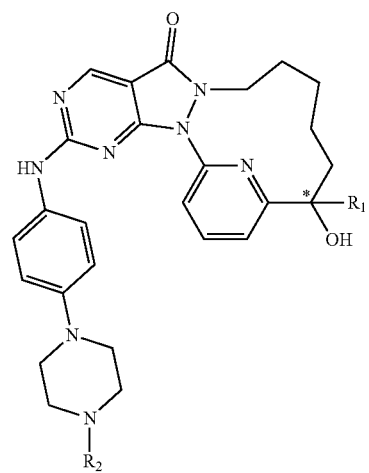

(I-2)

(I-3)

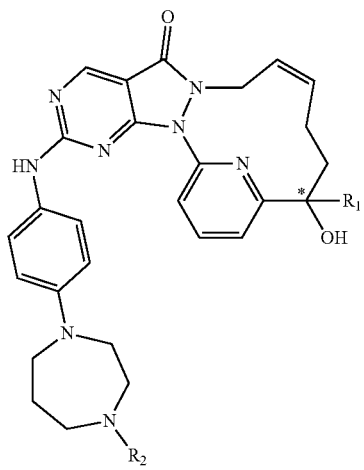

and (I-4)

wherein, $R_1$, $R_2$, $R_3$, $R_4$ are as defined in the present invention.

The present invention also provides a compound as shown below, an isomer thereof or a pharmaceutically acceptable salt thereof, which is selected from

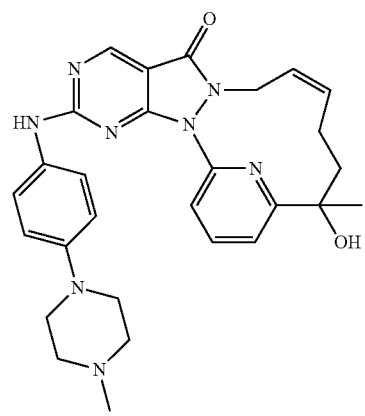
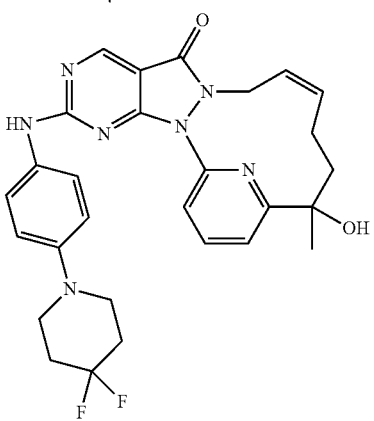
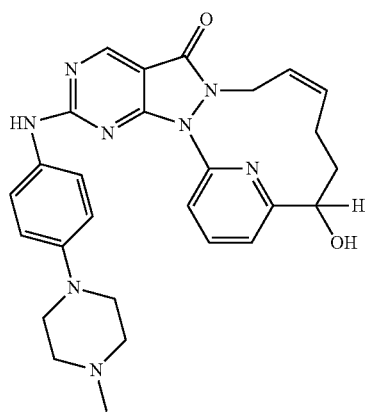
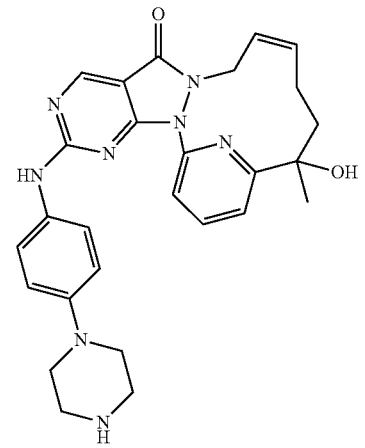
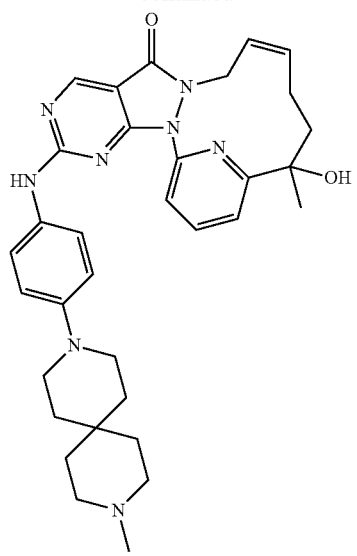
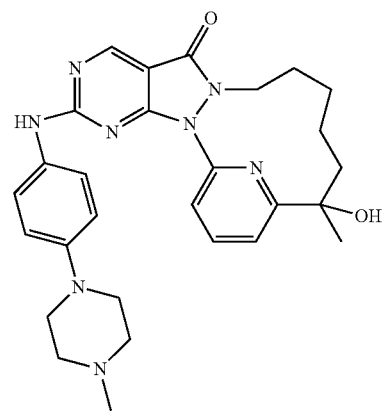
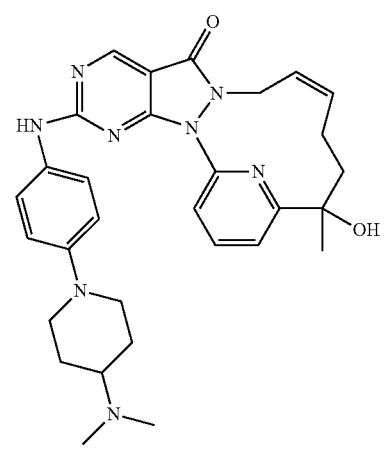

-continued
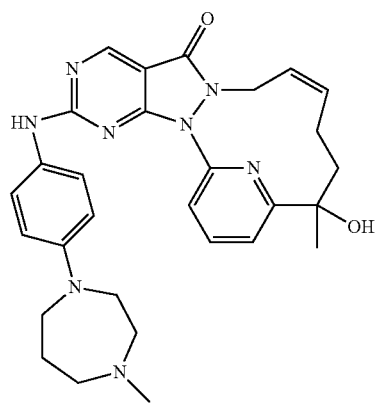
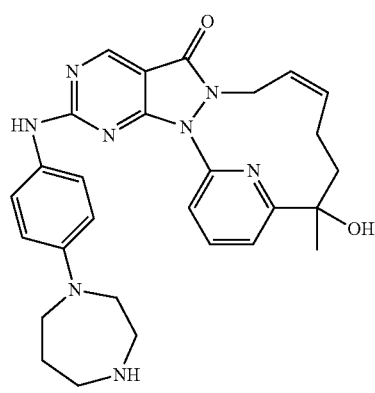
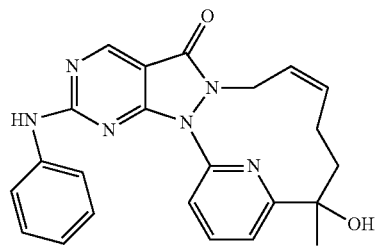
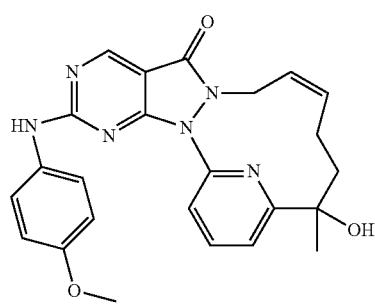
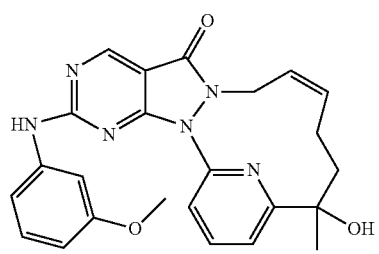
-continued
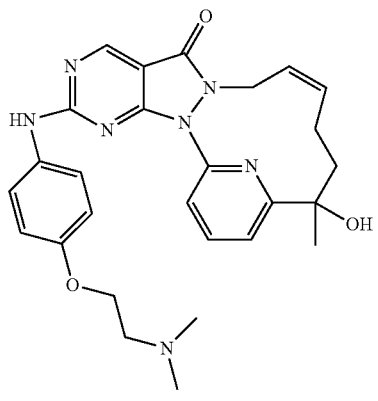
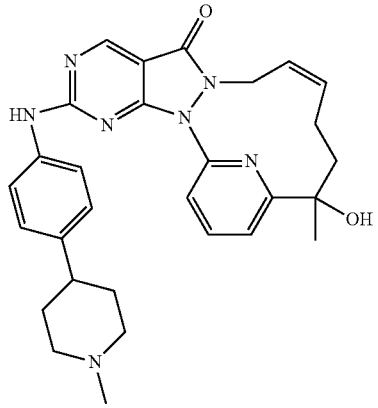
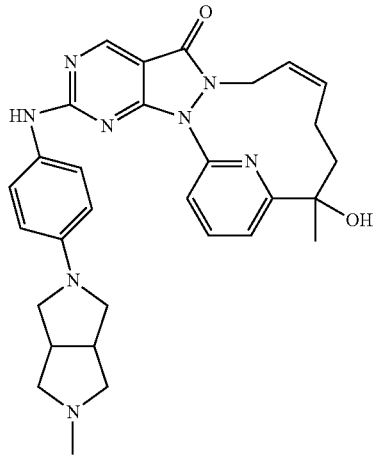
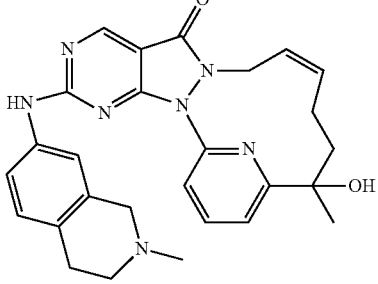

-continued
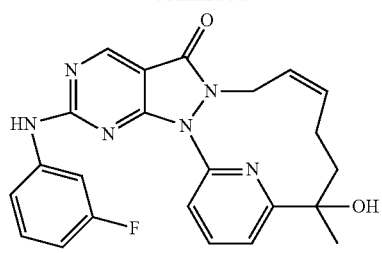
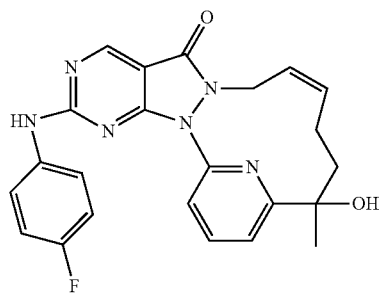
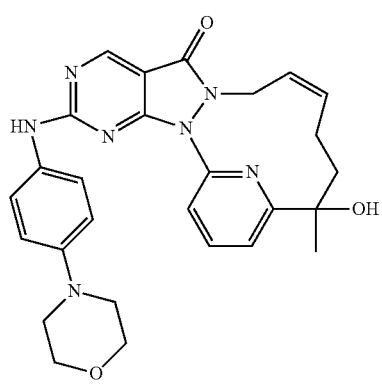
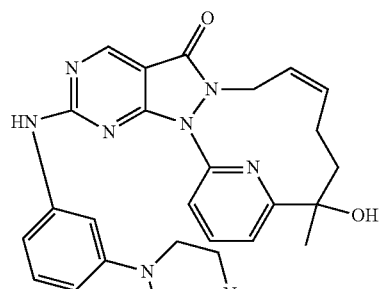
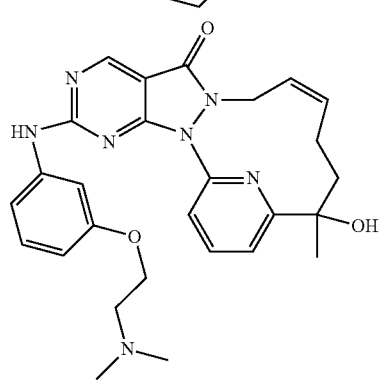
-continued
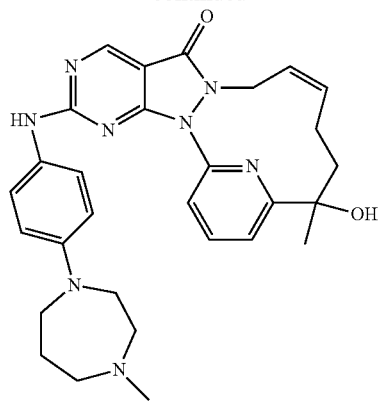
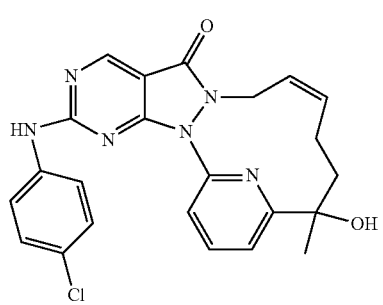
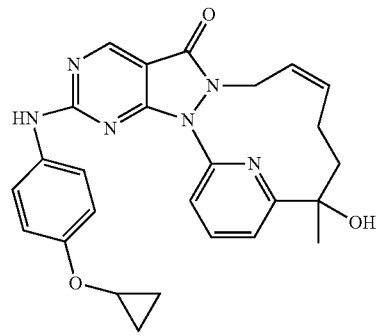
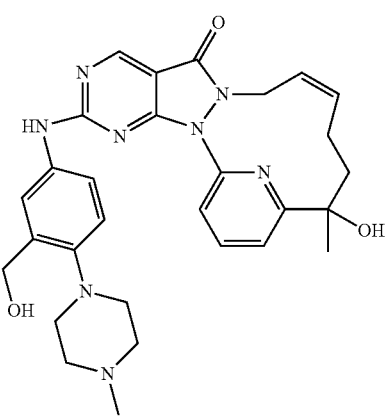

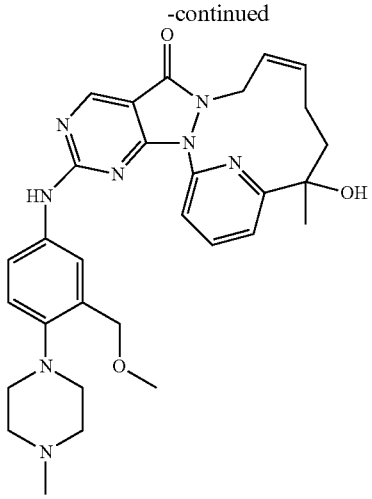
and
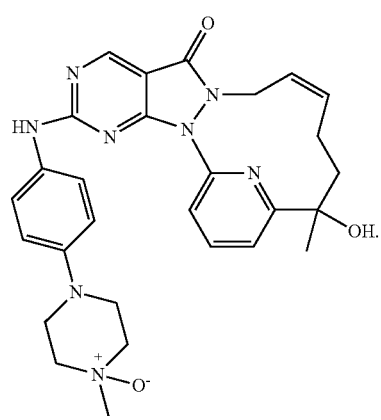
In some embodiments of the present invention, the compound, the isomer or the pharmaceutically acceptable salt thereof is selected from
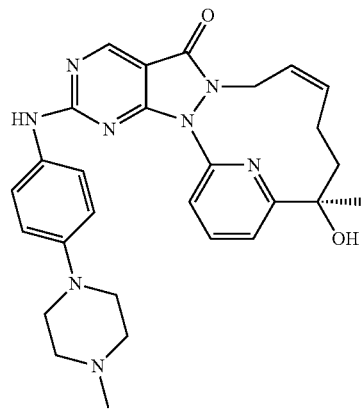
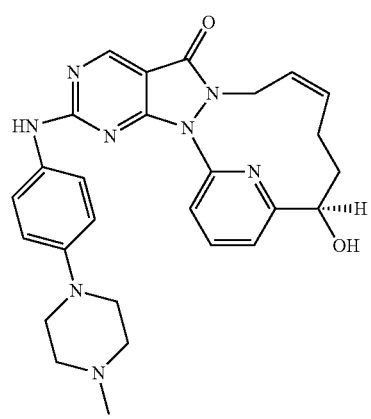
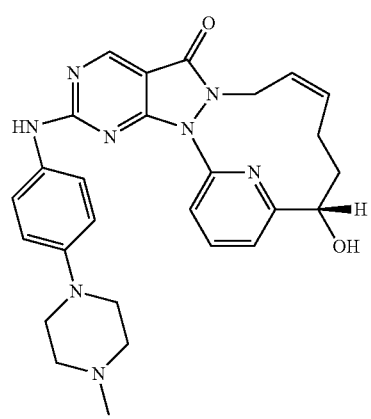
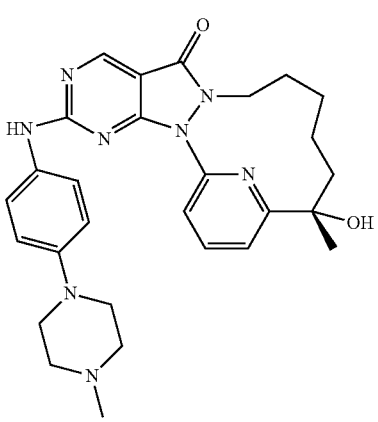

-continued
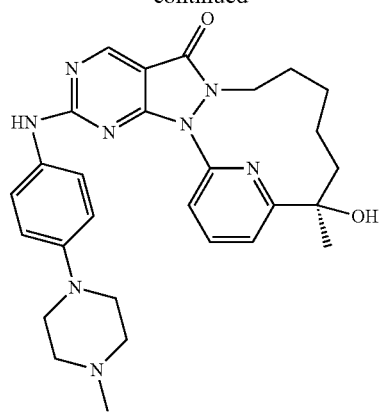
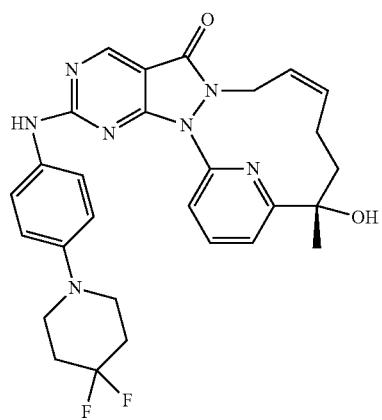
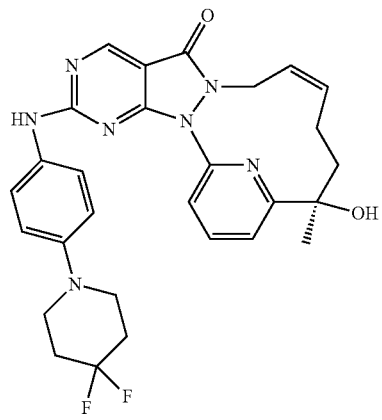
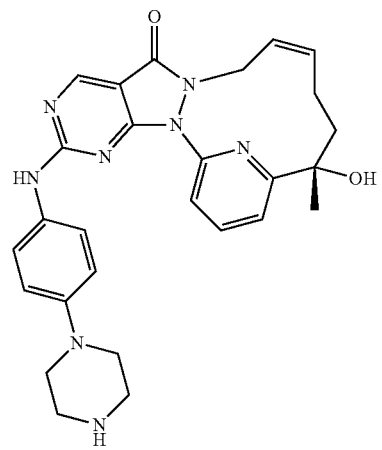
-continued
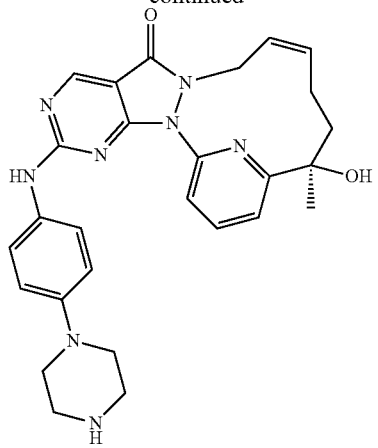
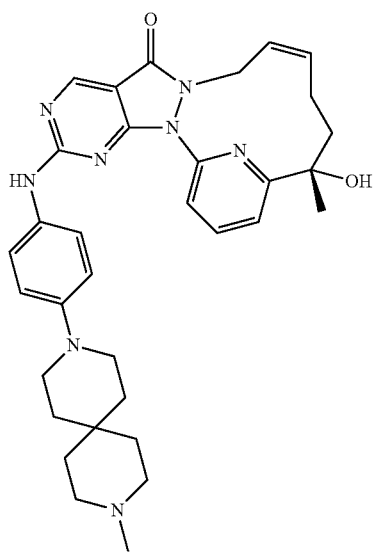
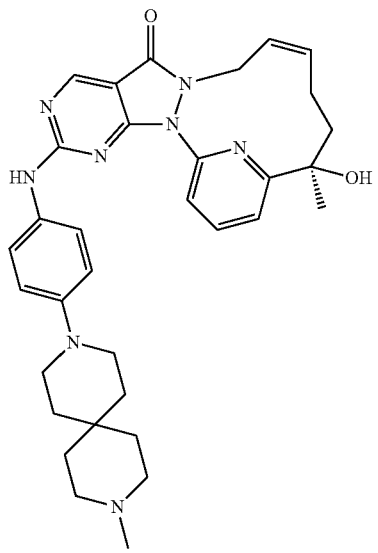

25
-continued
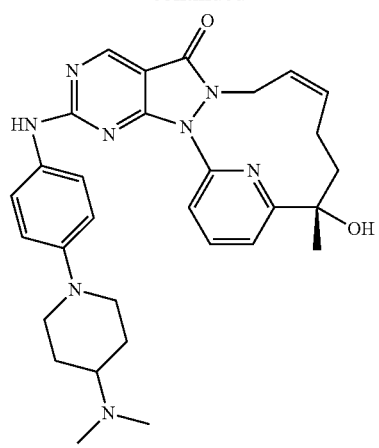
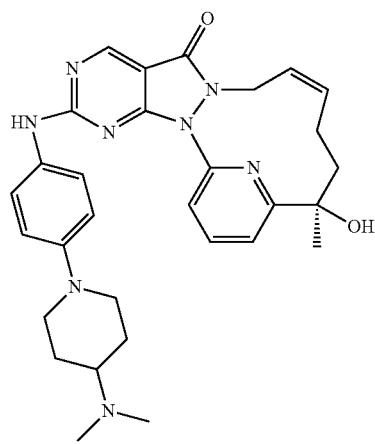
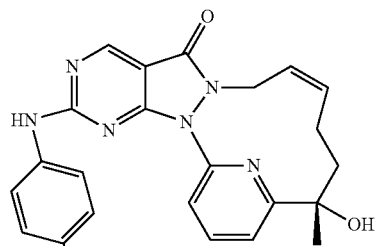
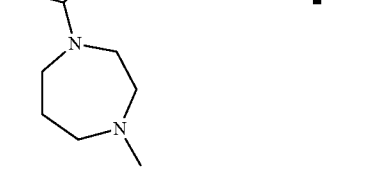
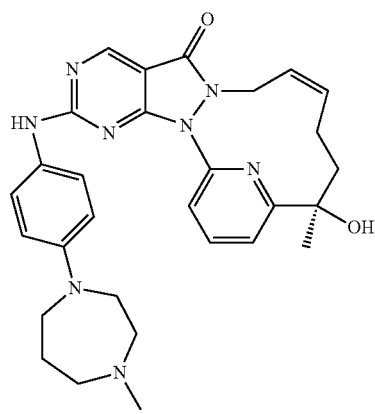
26
-continued
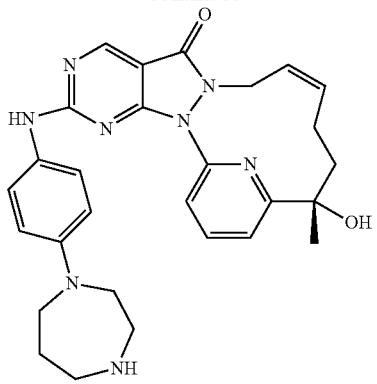
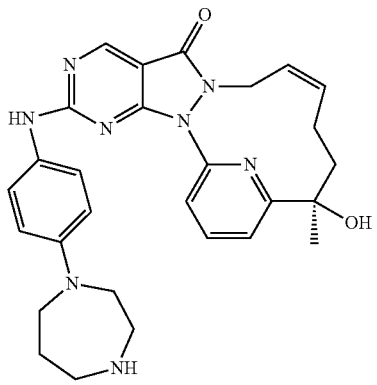
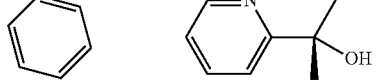
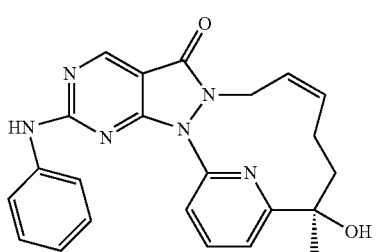
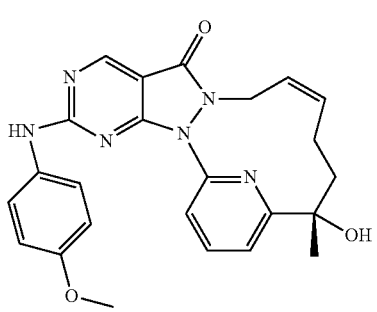

-continued
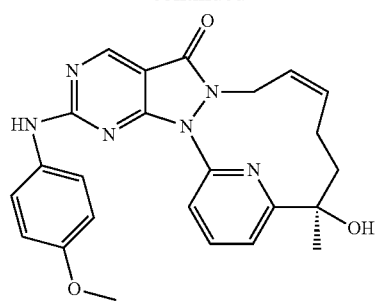
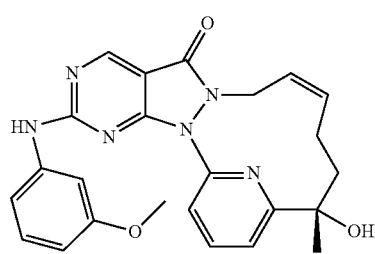
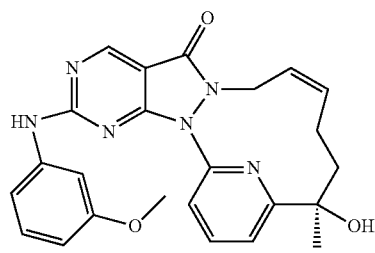
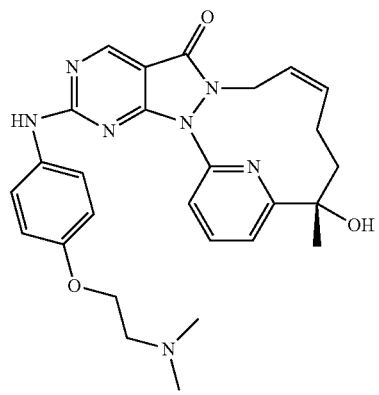
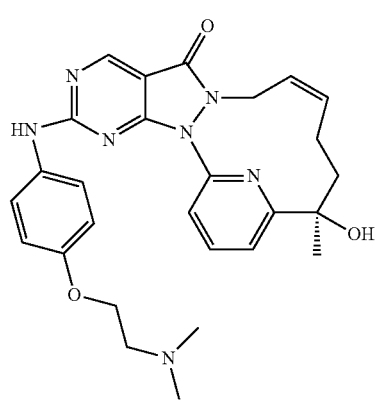
-continued
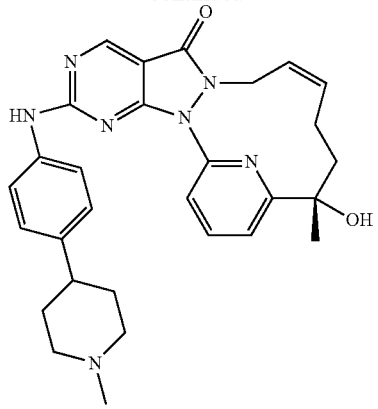
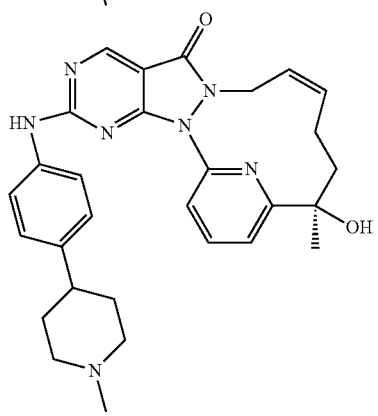
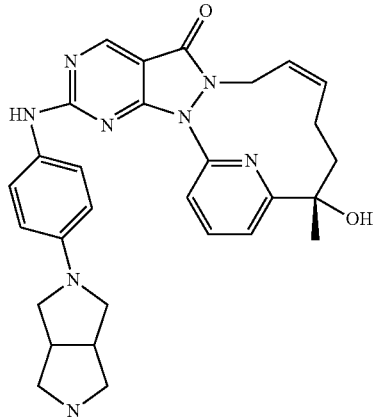
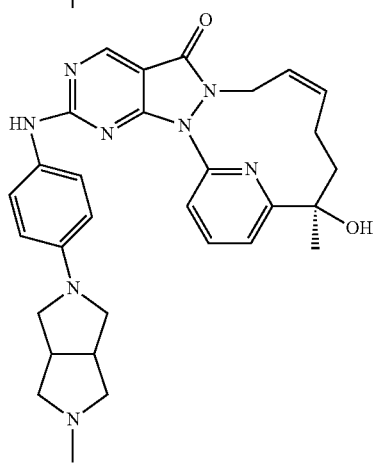

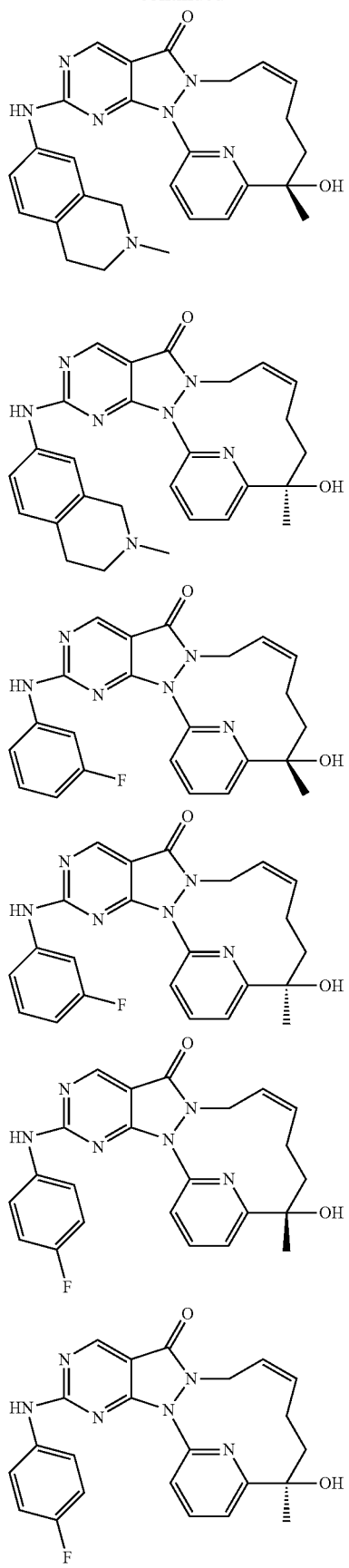
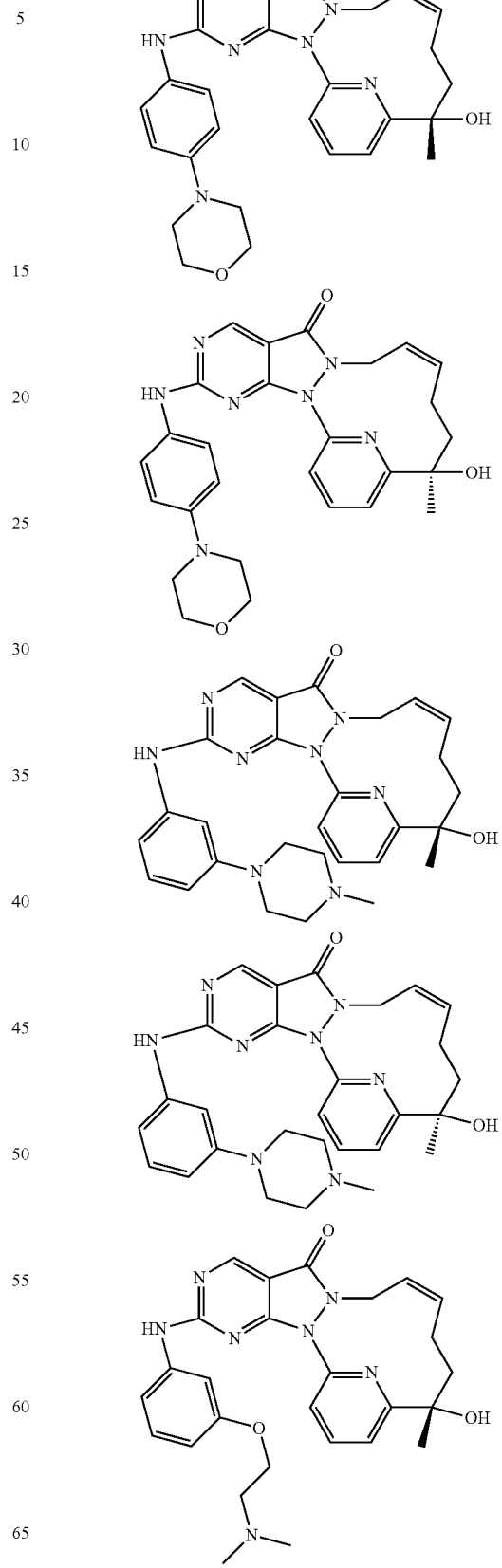

31
-continued
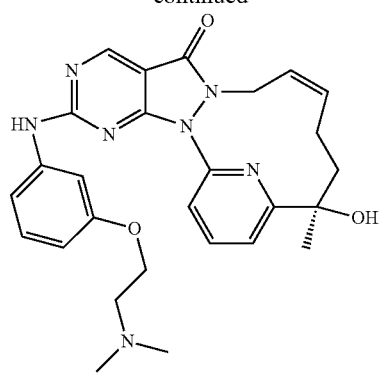
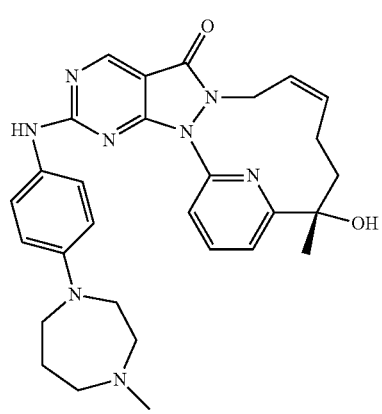
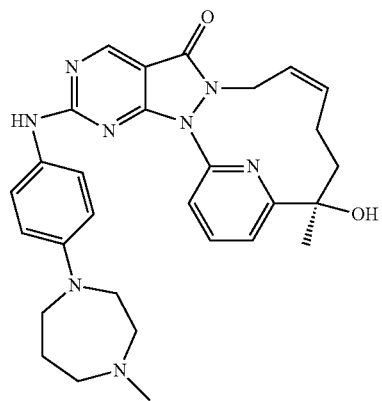
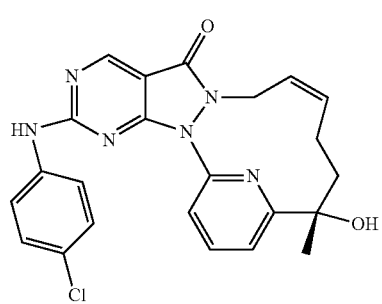
32
-continued
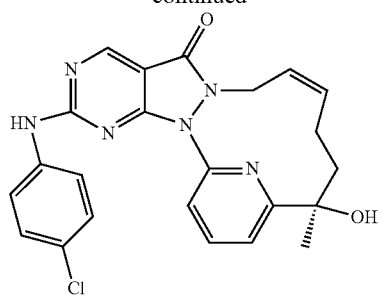
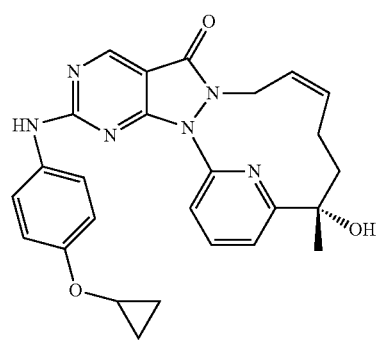
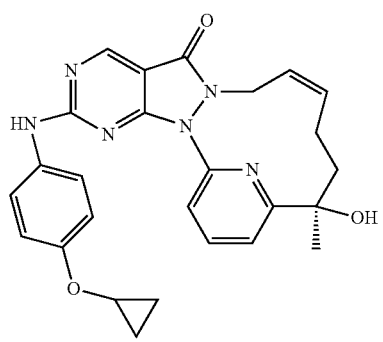
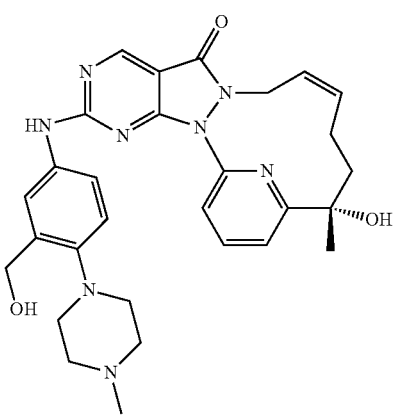

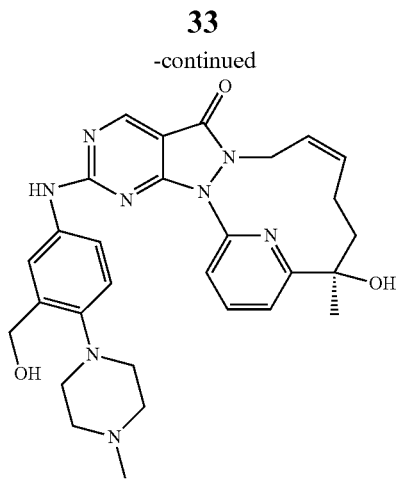

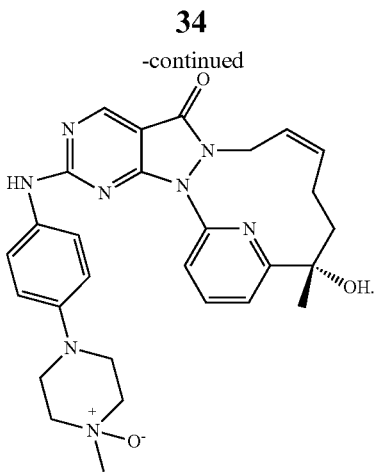

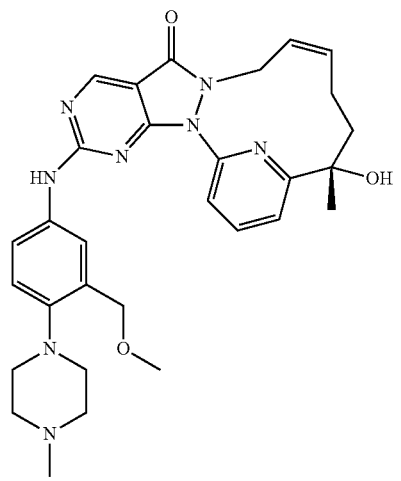

and

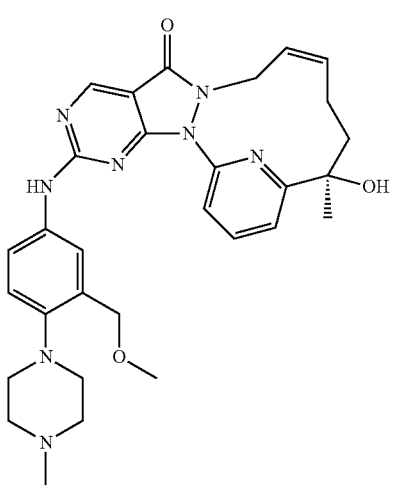

The present invention also provides a use of the compound or the pharmaceutically acceptable salt thereof in the manufacture of a medicament for treating Wee1-related diseases.

In some embodiments of the present invention, in the use above, wherein the medicament is used for the treatment of solid tumors.

Technical Effects

As a novel Wee1 inhibitor, the compound of the present invention has good inhibitory effect on Wee1 kinase and has good permeability. In terms of pharmacokinetics, it has significantly improved multiple pharmacokinetic indicators, including in vivo clearance rate, half-life, integral of concentration in vivo, and bioavailability. In terms of in vivo drug efficacy, the compound of the present invention significantly improves the tumor suppressive effect, and the chirality of the compound has unexpected effect on the in vivo efficacy of the drug.

Definition and Description

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present invention that contain both basic and acidic functional groups can be converted to any base or acid addition salt.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" stands for dextrorotation, "(L)" or "(−)" stands for levorotation, "(DL)" or "(±)" stands for racemization.

Unless otherwise specified, the absolute configuration of a stereogenic center is represented by a wedged solid bond ( ⌐ ) and a wedged dashed bond ( ⋯ ), and the relative configuration of a stereogenic center is represented by a straight solid bond ( ⌐ ) and a straight dashed bond ( ⋯ ). A wave line ( ∿ ) represents a wedged solid bond ( ⌐ ) or a wedged dashed bond ( ⋯ ), or represents a straight solid bond ( ⌐ ) or a straight dashed bond ( ⋯ ).

The compound of the present invention may be present in particular. Unless otherwise indicated, the term "tautomer" or "tautomeric form" refers to the fact that the different functional isomers are in dynamic equilibrium at room temperature and can be rapidly converted into each other. If tautomers are possible (such as in a solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise specified, the term "enriched in one isomer", "isomer enriched", "enriched in one enantiomer" or "enantiomer enriched" refers to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to obtain the pure enantiomer. In addition, the enantiomer and the diastereoisomer are generally isolated through chromatography which uses a chiral stationary phase and optionally combines with a chemical derivative method (such as carbamate generated from amine). The compound of the present invention may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, hydrogen can be replaced by heavy hydrogen to form a deuterated drug, and the bond composed of deuterium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the present invention, whether radioactive or not, are encompassed within the scope of the present invention. The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to those skilled in the cosmetic field or the topical pharmaceutical field.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When an enumerative substituent does not indicate by which atom it is attached to the substituted group, such substituent can be bonded by any of its atoms. For example, pyridyl as a substituent can be connected to the substituted group via any carbon atom on the pyridine ring. When the enumerative linking group does not indicate the direction for linking, the direction for linking is arbitrary, for example, the linking group L contained in

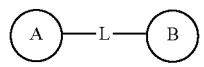

is -M-W—, then -M-W— can link ring A and ring B to form

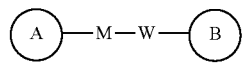

in the direction same as left-to-right reading order, and form

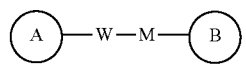

in the direction contrary to left-to-right reading order. Combinations of the linking groups, substituents and/or variants thereof are permissible only if such combinations result in stable compounds.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each "ring" independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)$_p$, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment. The total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimi dazolinyl, carbazolyl, 4aH-carbazolyl, carbolinyl, benzodihydropyranyl, chromene, cinnolinyl decahydroquinolinyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof, they can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl, the aliphatic hydrocarbyl includes chain and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched alkyl group or a combination thereof which has a specified number of carbon atoms and at least one heteroatom. In a specific embodiment, a heteroatom is selected from B, O, N and S, wherein nitrogen and sulfur atoms are optionally oxidized and the nitrogen heteroatom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclohydrocarbyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydro-thiophen-2-yl, tetrahydro-thiophen-3-yl, 1-piperazinyl and 2-piperazinyl.

Unless otherwise specified, the term "heterocycloalkyl" by itself or in combination with other terms means a cyclized "heteroalkyl". In addition, for the "heterocycloalkyl", heteroatoms may occupy the attachment position of the heterocycloalkyl to the rest of the molecule. In some embodiments, the heterocycloalkyl is 4-6 membered heterocycloalkyl; in other embodiments, the heterocycloalkyl is 5-6 membered heterocycloalkyl. Examples of heterocycloalkyl include, but are not limited to, azetidinyl, oxetanyl, thietanyl, pyrrolidinyl, pyrazolidinyl, imidazolidinyl, tetrahydrothienyl, tetrahydrofuranyl, tetrahydropyranyl, piperidinyl, piperazinyl, morpholinyl, dioxanyl, dithianyl, isoxazolidinyl, isothiazolidinyl, 1,2-oxazinyl, 1,2-thiazinyl, hexahydropyridazinyl, homopiperazinyl, homopiperidinyl or oxetanyl.

Unless otherwise specified, the term "alkyl" refers to a linear chain or branched saturated hydrocarbon group, can be mono-substituted (e.g., —$CH_2F$) or poly-substituted (e.g., —$CF_3$), can be monovalent (e.g., methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon double bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-ox azolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "arylalkyl" is meant to include the group (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxymethyl, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

The solvent used in the present invention is commercially available. The present invention employs the following abbreviations: aq stands for water; HATU stands for O-(7-azabenzotriazol-1-yl)-N,N,N',N'-tetramethyluronium hexafluoro-phosphate; EDC stands for N-(3-dimethylaminopropyl)-N-ethylcarbodiimide hydrochloride; m-CPBA stands for 3-chloroperoxybenzoic acid; eq stands for equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH for methanol; CBz stands for benzyloxycarbonyl, which is an amine protecting group; BOC stands for tert-butoxycarbonyl which is an amine protecting group; HOAc stands for acetic acid; NaCNBH$_3$ stands for sodium cyanoborohydride; r.t. stands for room temperature; O/N stands for overnight; THF stands for tetrahydrofuran; Boc$_2$O stands for di-tert-butyldicarbonate; TFA stands for trifluoroacetic acid; DIPEA stands for diisopropylethylamine; SOCl$_2$ stands for thionyl chloride; CS$_2$ stands for carbon disulfide; TsOH stands for p-toluenesulfonic acid; NFSI stands for N-fluoro-N-(phenylsulfonyl) benzenesulfonamide; NCS stands for N-chlorosuccinimide; n-Bu$_4$NF stands for tetrabutylammonium fluoride; iPrOH stands for 2-propanol; mp stands for melting point; LDA stands for diisopropylamino lithium; EA stands for ethyl acetate; NH$_3$H$_2$O stands for ammonia; DEA stands for diethanolamine; m-CPBA stands for m-chloroperoxybenzoic acid; ACN stands for acetonitrile; Tris-HCl stands for trishydroxymethylaminomethane hydrochloride; EDTA stands for ethylenediaminetetraacetic acid. IPA stands for isopropyl alcohol; NEAA stands for non-essential amino acids.

Compounds are named manually or by ChemDraw® software, the commercially available compounds use their vendor directory names.

Detailed Description of the Preferred Embodiment

The following examples further illustrate the present invention, but the present invention is not limited thereto. The present invention has been described in detail in the text, and its specific embodiments have also been disclosed, for one skilled person in the art, it is obvious to modify and improve the embodiments of the present invention within the spirit and scope of the present invention.

Intermediate 1

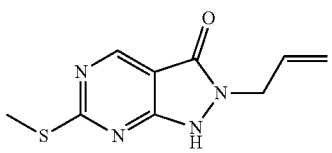

It was prepared with reference to the synthesis method in WO2007126122.

Example 1: Compound 1 and Compound 2

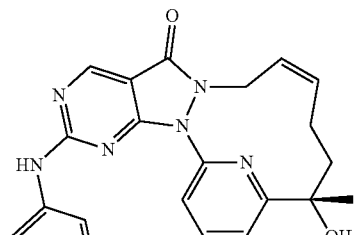

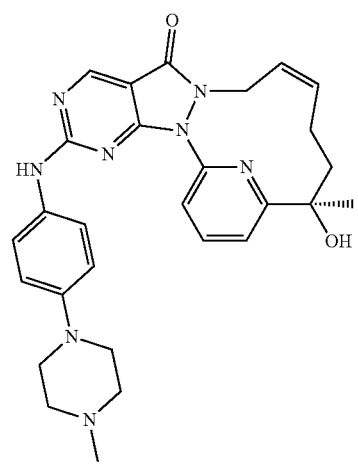

Synthetic Route

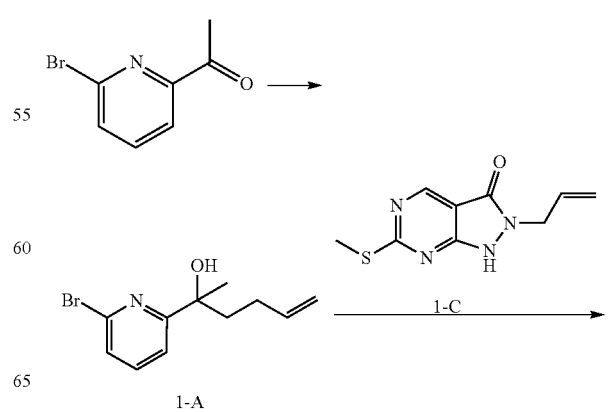

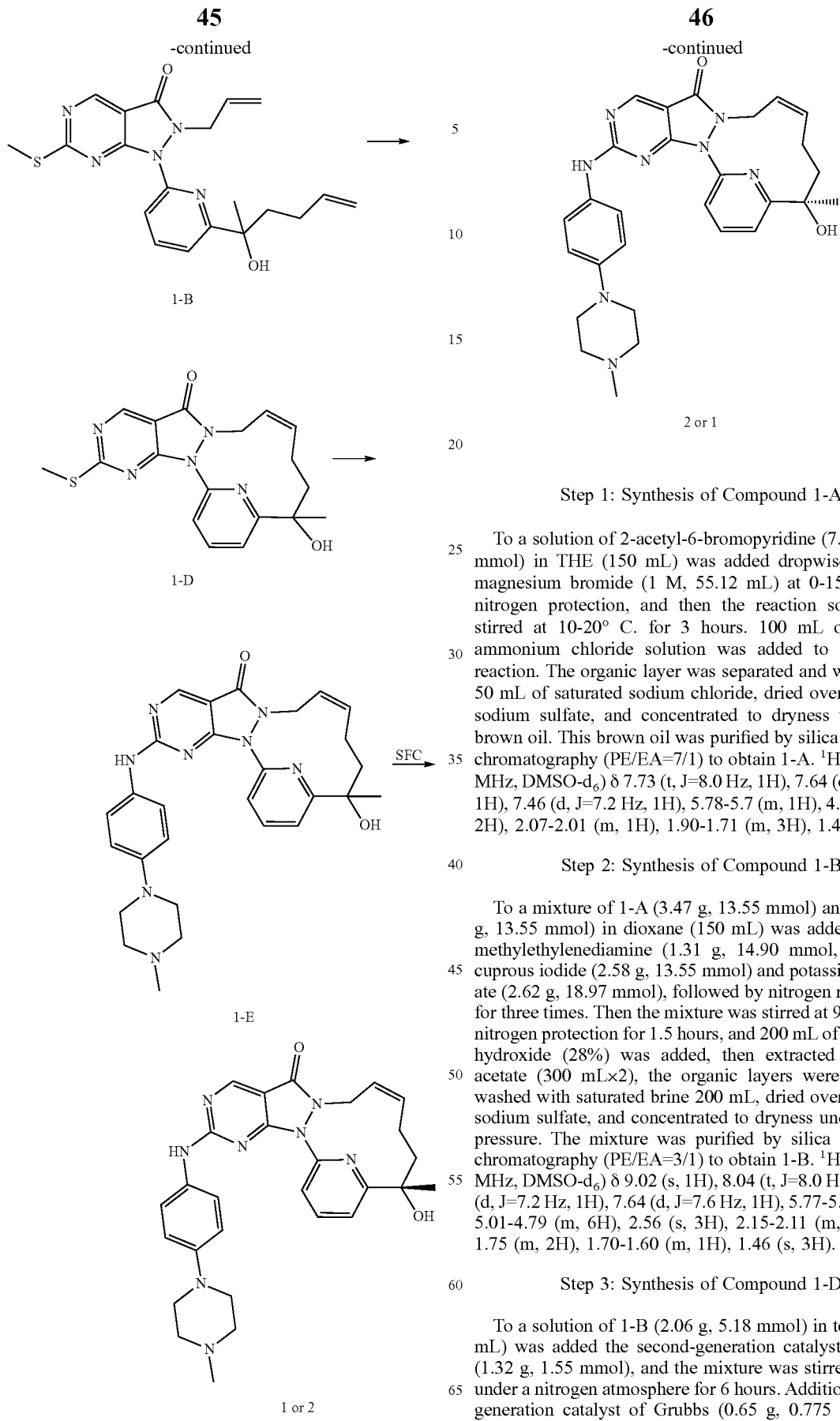

Step 1: Synthesis of Compound 1-A

To a solution of 2-acetyl-6-bromopyridine (7.35 g, 36.74 mmol) in THF (150 mL) was added dropwise 3-butenyl magnesium bromide (1 M, 55.12 mL) at 0-15° C. under nitrogen protection, and then the reaction solution was stirred at 10-20° C. for 3 hours. 100 mL of saturated ammonium chloride solution was added to quench the reaction. The organic layer was separated and washed with 50 mL of saturated sodium chloride, dried over anhydrous sodium sulfate, and concentrated to dryness to obtain a brown oil. This brown oil was purified by silica gel column chromatography (PE/EA=7/1) to obtain 1-A. $^1$H NMR (400 MHz, DMSO-$d_6$) δ 7.73 (t, J=8.0 Hz, 1H), 7.64 (d, J=7.2 Hz, 1H), 7.46 (d, J=7.2 Hz, 1H), 5.78-5.7 (m, 1H), 4.94-4.85 (m, 2H), 2.07-2.01 (m, 1H), 1.90-1.71 (m, 3H), 1.41 (s, 3H).

Step 2: Synthesis of Compound 1-B

To a mixture of 1-A (3.47 g, 13.55 mmol) and 1-C (3.01 g, 13.55 mmol) in dioxane (150 mL) was added N, N'-dimethylethylenediamine (1.31 g, 14.90 mmol, 1.60 mL), cuprous iodide (2.58 g, 13.55 mmol) and potassium carbonate (2.62 g, 18.97 mmol), followed by nitrogen replacement for three times. Then the mixture was stirred at 95° C. under nitrogen protection for 1.5 hours, and 200 mL of ammonium hydroxide (28%) was added, then extracted with ethyl acetate (300 mL×2), the organic layers were combined, washed with saturated brine 200 mL, dried over anhydrous sodium sulfate, and concentrated to dryness under reduced pressure. The mixture was purified by silica gel column chromatography (PE/EA=3/1) to obtain 1-B. $^1$H NMR (400 MHz, DMSO-$d_6$) δ 9.02 (s, 1H), 8.04 (t, J=8.0 Hz, 1H), 7.76 (d, J=7.2 Hz, 1H), 7.64 (d, J=7.6 Hz, 1H), 5.77-5.67 (m, 2H), 5.01-4.79 (m, 6H), 2.56 (s, 3H), 2.15-2.11 (m, 1H), 1.85-1.75 (m, 2H), 1.70-1.60 (m, 1H), 1.46 (s, 3H).

Step 3: Synthesis of Compound 1-D

To a solution of 1-B (2.06 g, 5.18 mmol) in toluene (700 mL) was added the second-generation catalyst of Grubbs (1.32 g, 1.55 mmol), and the mixture was stirred at 80° C. under a nitrogen atmosphere for 6 hours. Additional second-generation catalyst of Grubbs (0.65 g, 0.775 mmol) was added, and the mixture was stirred at 80° C. under a nitrogen atmosphere for 3 hours. Then the reaction mixture was cooled to room temperature, filtered, and the filtrate was concentrated to dryness to obtain a brown residue, which was purified by silica gel column chromatography (PE/EA=1/1) to obtain 1-D. $^1$H NMR (400 MHz, DMSO-$d_6$) δ 9.07 (s, 1H), 8.06 (t, J=8.0 Hz, 1H), 7.79 (d, J=8.2 Hz, 1H), 7.70 (d, J=7.6 Hz, 1H), 5.39-5.25 (m, 3H), 4.66 (d, J=5.2 Hz, 2H), 2.62 (s, 3H), 2.40-1.95 (m, 3H), 1.85-1.65 (m, 1H) 1.64 (s, 3H).

Step 4: Synthesis of Compound 1-E

To a solution of compound 1-D (360 mg, 974.45 μmol) in toluene (35 mL) was added m-chloroperoxybenzoic acid (265.09 mg, 1.31 mmol, 85% purity), and the reaction was stirred at 25° C. for 2 hours. To the reaction solution, 4-(4-methylpiperazine)aniline (242.30 mg, 1.27 mmol) and N, N-diisopropylethylamine (503.76 mg, 3.90 mmol) were added. The reaction solution was stirred at 25° C. for 12 hours. 25 mL of water was added to the reaction solution and stirred, and the aqueous phase was extracted with ethyl acetate (30 mL×3). The organic phases were combined, washed once with saturated sodium bicarbonate solution (30 mL) and saturated brine (30 mL) respectively, and dried over anhydrous sodium sulfate, filtered, and concentrated under vacuum to obtain a crude product, which is separated by preparative liquid (neutral) chromatography to obtain 1-E. $^1$H NMR (400 MHz, CDCl$_3$) δ ppm 1.70 (s, 3H) 1.78 (br d, J=13.54 Hz, 2H), 2.04 (br d, J=6.54 Hz, 1H), 2.08-2.23 (m, 2H), 2.39 (s, 3H), 2.62-2.64 (m, 4H), 3.21-3.24 (m, 4H), 4.24 (br s, 1H), 4.51 (br d, J=13.54 Hz, 1H), 5.61-5.88 (m, 2H), 6.95 (d, J=9.04 Hz, 2H), 7.49 (d, J=9.04 Hz, 3H), 7.81-7.90 (m, 2H), 8.87 (s, 1H); MS m/z: 513.1 [M+H]$^+$.

Step 5: Synthesis of Compound 1 and 2

Compound 1-E (100 mg, 195.08 μmol) was subjected to SFC chiral resolution (chromatographic column: A.D. 250×50 mm ID, 10 μm, mobile phase: A: supercritical CO$_2$, B: EtOH (0.1% NH$_3$H$_2$O), A: B=55:45 at 200 mL/min) to obtain 1, retention time: 21 min. $^1$H NMR (400 MHz, CDCl$_3$) δ ppm 1.60 (s, 3H), 1.68 (br s, 2H), 1.94 (br d, J=7.04 Hz, 1H), 2.00-2.20 (m, 2H), 2.30 (s, 3H), 2.52-2.55 (m, 4H), 3.12-3.15 (m, 4H), 4.24 (br s, 1H), 4.42 (br d, J=9.54 Hz, 1H), 5.65 (br s, 2H), 6.85 (d, J=9.04 Hz, 2H), 7.17 (s, 1H), 7.40 (d, J=9.04 Hz, 2H), 7.69-7.81 (m, 2H), 8.77 (s, 1H). MS m/z: 513.1 [M+H]$^+$. And 2, retention time: 42 min. $^1$H NMR (400 MHz, CDCl$_3$) δ ppm 1.61 (s, 3H), 1.70 (br d, J=5.02 Hz, 2H), 1.94 (br s, 1H), 2.03-2.18 (m, 2H), 2.30 (s, 3H), 2.52-2.55 (m, 4H), 3.12-3.15 (m, 4H), 4.16 (br s, 1H), 4.42 (br d, J=11.04 Hz, 1H), 5.66 (br s, 2H), 6.85 (d, J=9.04 Hz, 2H), 7.18 (s, 1H), 7.40 (d, J=9.04 Hz, 2H), 7.71-7.81 (m, 2H), 8.77 (s, 1H). MS m/z: 513.1 [M+H]$^+$.

Example 2: Compound 3

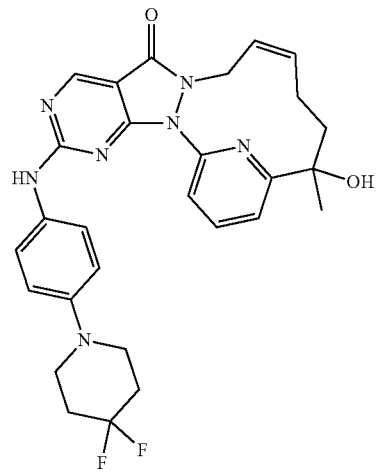 [SMILES: CC1(O)CC/C=C\Cn2c(=O)c3cnc(Nc4ccc(N5CCC(F)(F)CC5)cc4)nc3n2-c2cccc1n2]

Synthetic Route

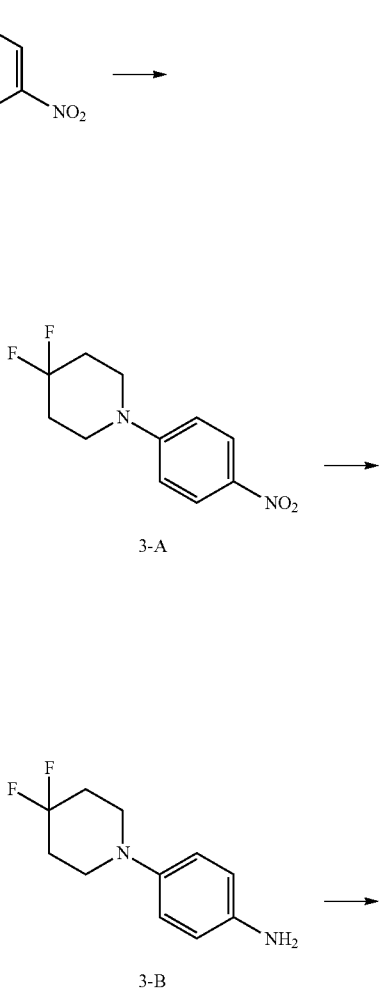

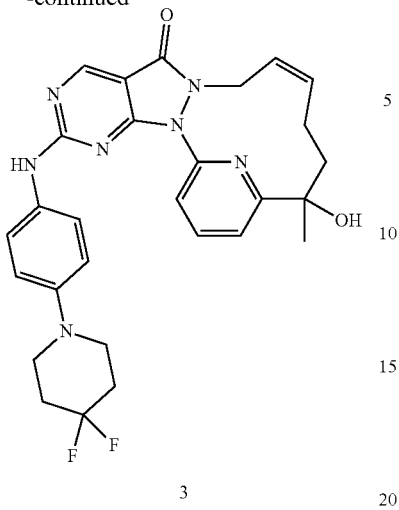

3

Step 1: Synthesis of Compound 3-A

The compound 4-fluoronitrobenzene (2.46 g, 17.45 mmol, 1.85 mL) was added to DMF (30 mL), followed by addition of $K_2CO_3$ (5.48 g, 39.66 mmol) and 4,4-difluoropiperidine hydrochloride (2.5 g, 15.86 mmol), the reaction mixture was reacted at 60° C. for 6 hours. $H_2O$ (20 mL) was added to the reaction solution for dilution, and then EtOAc (20 mL) was added for extraction, the organic phase was dried, filtered and concentrated to obtain a crude product, which was purified by column chromatography ($SiO_2$, PE/EA=100/1 to 20/1) to obtain compound 3-A. $^1H$ NMR (400 MHz, $CDCl_3$): 8.05-8.21 (m, 2H), 6.78-6.93 (m, 2H), 3.53-3.65 (m, 4H), 2.09 (ddd, J=19.46, 13.51, 5.84 Hz, 4H); MS m/z: 242.09 $[M+H]^+$.

Step 2: Synthesis of Compound 3-B

Compound 3-A (1.5 g, 6.19 mmol) was added to THE (15 mL), then Pd/C (0.2 g, 10% purity) was added, and the reaction solution was stirred at 25° C. for 2 hours under $H_2$ atmosphere (15 psi). The reaction solution was filtered to remove Pd/C, and the organic phase was dried by rotary evaporation to obtain 3-B. $^1H$ NMR (400 MHz, $CDCl_3$): 6.69-6.84 (m, 2H), 6.53-6.64 (m, 2H), 3.02-3.17 (m, 4H), 1.97-2.13 (m, 4H). MS m/z: 212.11 $[M+H]^+$.

Step 3: Synthesis of Compound 3

1-D (0.2, 541.36 μmol) was added to toluene (2 mL), then m-CPBA (153.87 mg, 757.90 μmol, 85% purity) was added, the reaction mixture was stirred at 25° C. for 1 hour, then 3-B (126.39 mg, 595.50 μmol) was added, the reaction mixture was stirred at 25° C. for 2 hours, saturated $Na_2SO_3$ solution (10 mL) was added to the reaction solution, followed by extraction with EtOAc (10 mL×3) n, the organic phase was dried, filtered and concentrated to obtain a brown oil, which was purified by preparative TLC ($SiO_2$, PE/EA=1:1) and preparative high-performance liquid chromatography to obtain 3. $^1H$ NMR (400 MHz, $CDCl_3$): 8.86 (s, 1H), 7.84-7.90 (m, 1H), 7.77-7.83 (m, 1H), 7.45-7.57 (m, 3H), 6.95 (d, J=9.04 Hz, 2H), 5.72 (br s, 2H), 4.22 (s, 1H), 3.28-3.38 (m, 4H), 2.04-2.24 (m, 6H), 1.61-1.72 (m, 7H). MS m/z: 533.24 $[M+H]^+$.

Example 3: Compound 4 and Compound 5

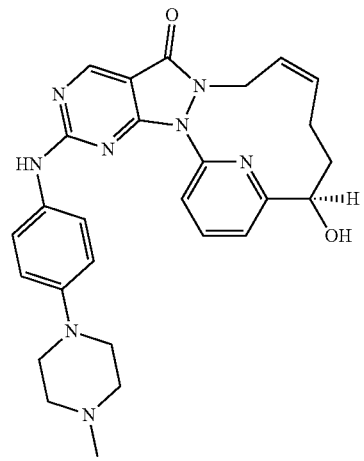

Synthetic Route

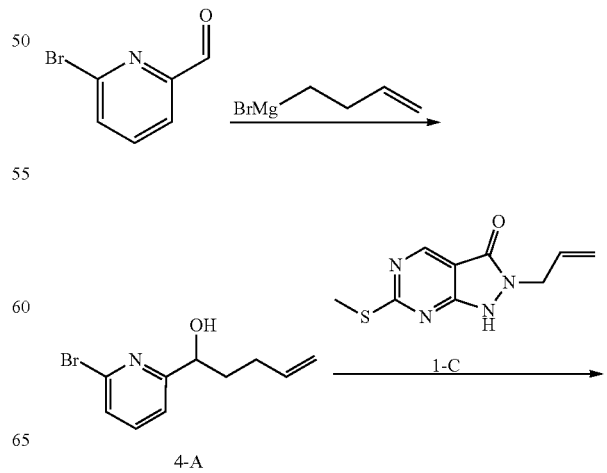

4-A

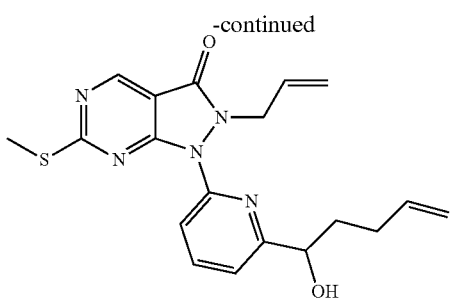

4-B

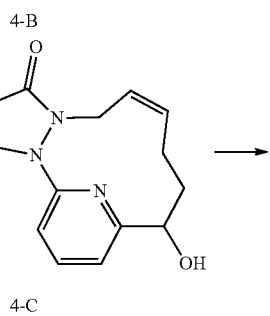

4-C

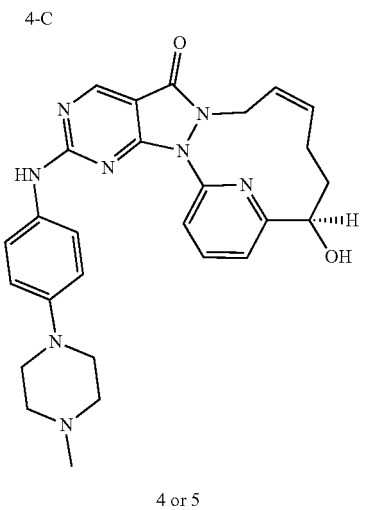

4 or 5

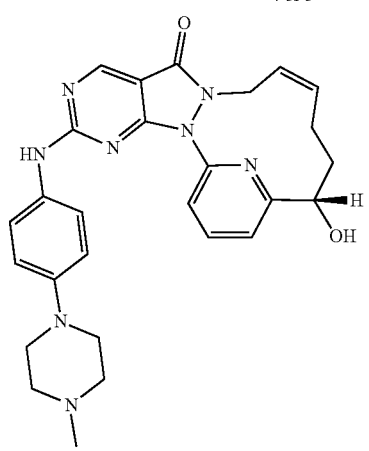

5 or 4

Step 1: Synthesis of Compound 4-A

To a solution of compound 6-bromopyridine-2-carbaldehyde (15 g, 80.64 mmol) in THF (150 mL) was added dropwise 3-butenyl magnesium bromide (0.5 M, 725.78 mL) at 0-15° C. under nitrogen protection. And then the reaction solution was stirred at 10-20° C. for 12 hours. 50 mL of saturated ammonium chloride was added. The reaction solution was extracted with 200 mL of ethyl acetate. The organic phase was washed with 100 mL of saturated brine, dried over anhydrous sodium sulfate, filtered and dried by rotary evaporation to obtain a dark brown oil, which is purified by silica gel column chromatography (PE/EA=5/1) to obtain 4-A. MS m/z: 242.0 [M+H]$^+$.

Step 2: Synthesis of Compound 4-B

In a reaction flask was added compound 4-A (1.29 g, 5.34 mmol), intermediate 1-C (1.13 g, 5.08 mmol), CuI (1.02 g, 5.34 mmol), K$_2$CO$_3$ (1.03 g, 7.43 mmol), N, N-dimethylethylenediamine (518.25 mg, 5.88 mmol, 632.78 μL), 1,4-dioxane (20 mL), followed by nitrogen replacement for three times. Then the reaction solution was stirred at 95° C. for 13 hours under nitrogen atmosphere. 50 mL of ammonium hydroxide was added. The reaction solution was extracted with 100 mL of ethyl acetate, and the organic phase was washed with 50 mL of saturated brine, dried over anhydrous sodium sulfate, filtered, and dried by rotary evaporation to obtain 4-B. MS m/z: 384.2 [M+H]$^+$.

Step 3: Synthesis of Compound 4-C

Compound 4-B (1.3 g, 3.39 mmol), second-generation catalyst of Grubbs (863.44 mg, 1.02 mmol) and toluene (455 mL) were added to a reaction flask, followed by nitrogen replacement for three times. Then this reaction solution was stirred at 80° C. for 6 hours under nitrogen atmosphere. The reaction solution was filtered, and the filtrate was dried by rotary evaporation and purified by column chromatography (silica, petroleum ether:ethyl acetate=10: 1-1:1) to obtain crude 4-C. MS m/z: 355.9 [M+H]$^+$.

Step 4: Synthesis of Compound 4 and Compound 5

Compound 4-C (0.159 g, 447.37 μmol), m-CPBA (124.43 mg, 612.89 μmol), and toluene (2 mL) were added to a reaction flask, and the reaction solution was stirred at 25° C. for 1 hour. To the reaction solution was added 4-(4-methylpiperazine)aniline (119.80 mg, 626.32 μmol), diisopropylethylenediamine (289.09 mg, 2.24 mmol, 389.61 μL), and the reaction solution was stirred at 25° C. for 12 hours. 5 mL of saturated aqueous sodium sulfite solution was added to the reaction solution, and 10 mL of DCM was added for extraction. The organic phase was dried over anhydrous sodium sulfate, filtered and dried by rotary evaporation to obtain a crude product. The crude product was dissolved in 2 mL of methanol and separated with a preparative liquid chromatography (chromatographic column: Luna C18 100*30 mm 5 μm; mobile phase: [water (0.1% TFA)-ACN]; B (acetonitrile) %: 15%-35%, 10 min) and freed with Albert-21 basic resin (the pH was adjusted to 7), filtered, and concentrated to obtain a residue. The above operation was repeated to obtain another batch of residues, and the two batches of residues were separated by SFC (chromatographic column: Chiralpak AD-H 250*30 mm i.d. 5 μm, mobile phase: A: CO$_2$, B: IPA (0.1% NH$_3$H$_2$O), gradient: B %=45%, flow rate: 75 g/min) to obtain 4, retention time: 10.5 min. $^1$H NMR (400 MHz, CDCl$_3$) δ ppm 8.85 (s, 1H), 7.82-7.89 (m, 2H), 7.45-7.54 (m, 2H), 7.18-7.24 (m, 1H), 6.91-6.96 (m, 2H), 5.71-5.73 (m, 2H), 4.92-4.97 (m, 1H), 4.41-4.47 (m, 1H), 3.19-3.27 (m, 4H), 2.60-2.72 (m, 4H), 2.41 (s, 3H), 1.5-2.2 (m, 6H); MS m/z: 499.2 [M+H]$^+$.

And 5, retention time: 16 min.

Example 4: Compound 6

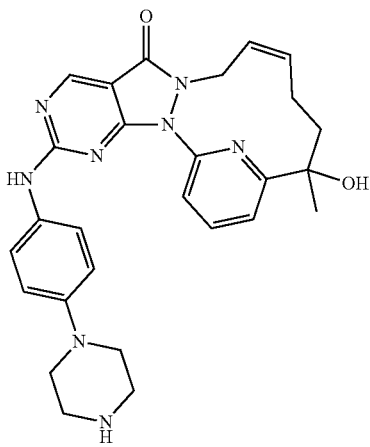 [SMILES: CC1(O)CC/C=C\Cn2c(=O)c3cnc(Nc4ccc(N5CCNCC5)cc4)nc3n2-c2cccc1n2]

Synthetic Route

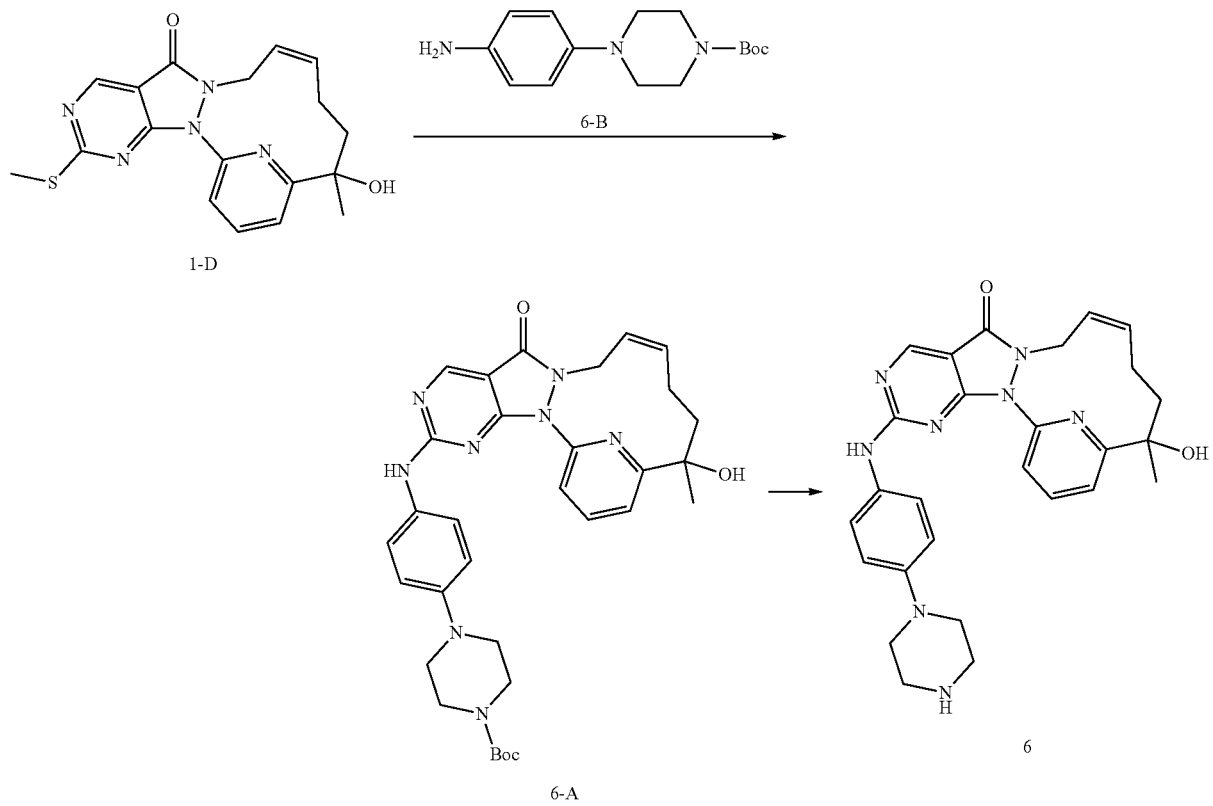

Step 1: Synthesis of Compound 6-A

To a solution of compound 1-D (128 mg, 346.47 μmol) in toluene (30 mL) was added m-chloroperoxybenzoic acid (92.85 mg, 457.34 μmol, 85% purity), and the reaction was stirred at 25° C. for 2 hours. 6-B (134.54 mg, 485.06 μmol) and N, N-diisopropylethylamine (223.89 mg, 1.73 mmol) were added to the reaction solution. The reaction solution was stirred at 25° C. for 12 hours. 10 mL of water was added to the reaction solution and stirred, and the aqueous phase was extracted with ethyl acetate (10 mL×3). The organic phases were combined, washed once with saturated sodium bicarbonate solution (20 mL) and saturated brine (20 mL) respectively, and dried over anhydrous sodium sulfate, filtered, and concentrated under vacuum to obtain a crude product of 6-A. MS m/z: 599.1 [M+H]$^+$.

Step 2: Synthesis of Compound 6

To a solution of compound 6-A (265 mg, 442.63 μmol) in dichloromethane (15 mL) was added trifluoroacetic acid (7.70 g, 67.53 mmol), and the reaction was stirred at 20° C. for 30 minutes. The reaction solution was rotary-evaporated to obtain a crude product, to which was added saturated sodium bicarbonate solution to adjust pH to 7-8, and the aqueous phase was extracted with ethyl acetate (20 mL×3). The organic phases were combined, washed once with saturated brine (20 mL), and dried over anhydrous sodium sulfate, filtered and concentrated under vacuum to obtain a crude product, which is separated by preparative liquid (neutral) chromatography to obtain 6. $^1$H NMR (400 MHz, CDCl$_3$) δ ppm 1.61 (s, 3H), 1.70 (br d, J=5.02 Hz, 2H), 1.86-1.97 (m, 1H), 2.00-2.14 (m, 2H), 2.97-3.01 (m, 4H), 3.05-3.09 (m, 4H), 4.23 (br s, 1H), 4.42 (br d, J=13.04 Hz, 1H), 5.65 (br s, 2H), 6.86 (d, J=9.04 Hz, 2H), 7.40 (br d, J=9.04 Hz, 3H), 7.71-7.82 (m, 2H), 8.78 (s, 1H). MS m/z: 499.0 [M+H]$^+$.

Example 5: Compound 7

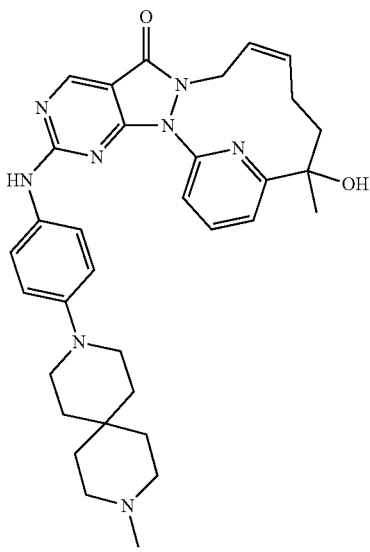

Synthetic Route

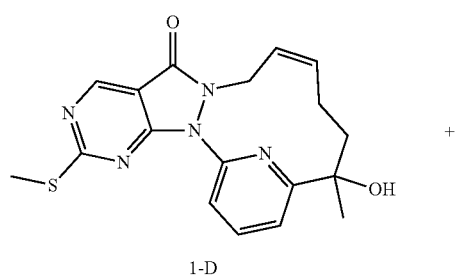

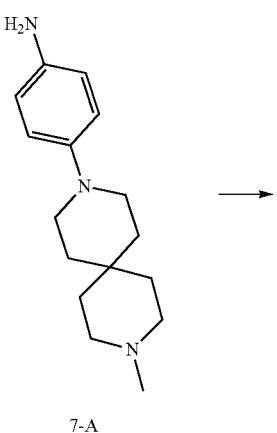

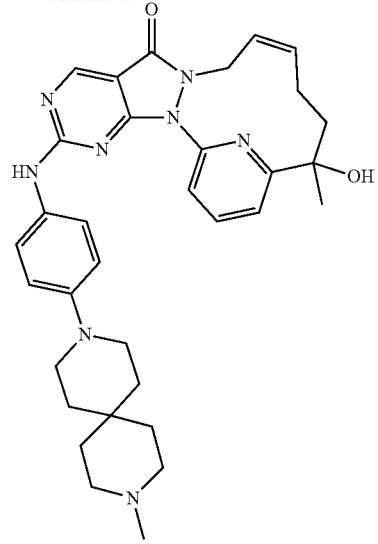 [SMILES: CN1CCC2(CC1)CCN(c1ccc(Nc3ncc4c(=O)n5n(c4n3)-c3cccc(n3)C(C)(O)CC/C=C\C5)cc1)CC2]

7

Step 1: Synthesis of Compound 7

To a solution of compound 1-D (0.35 g, 947.38 μmol) in toluene (30 mL) was added m-chloroperoxybenzoic acid (257.73 mg, 1.27 mmol, 85% purity), and the reaction was stirred at 25° C. for 2.5 hours. 7-A (319.46 mg, 1.23 mmol) and N, N-diisopropylethylamine (612.21 mg, 4.74 mmol) were added to the reaction solution. The reaction solution was stirred at 25° C. for 12 hours. 10 mL of water was added to the reaction solution and stirred, and the aqueous phase was extracted with ethyl acetate (15 mL×3). The organic phases were combined, washed once with saturated sodium bicarbonate solution (20 mL) and saturated brine (20 mL) respectively, and dried over anhydrous sodium sulfate, filtered and concentrated under vacuum to obtain a crude product, which was separated by preparative liquid (neutral) chromatography and preparative TLC (dichloromethane/methanol=15/1) to obtain 7.

$^1$H NMR (400 MHz, CDCl$_3$) δ ppm 1.60 (br s, 11H), 1.69 (br d, J=14.82 Hz, 2H), 1.94 (br s, 1H), 2.06 (br s, 2H), 2.33 (s, 3H), 2.48 (br s, 4H), 3.05-3.10 (m, 4H), 4.24 (br s, 1H), 4.41 (br d, J=11.80 Hz, 1H), 5.65 (br s, 2H), 6.86 (br d, J=8.54 Hz, 2H), 7.18 (br s, 1H), 7.39 (br d, J=8.78 Hz, 2H), 7.71-7.82 (m, 2H), 8.77 (s, 1H). MS m/z: 581.1 [M+H]$^+$.

Example 6: Compound 8

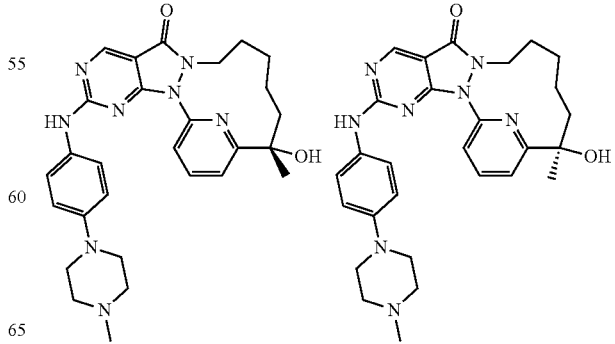

Synthetic Route

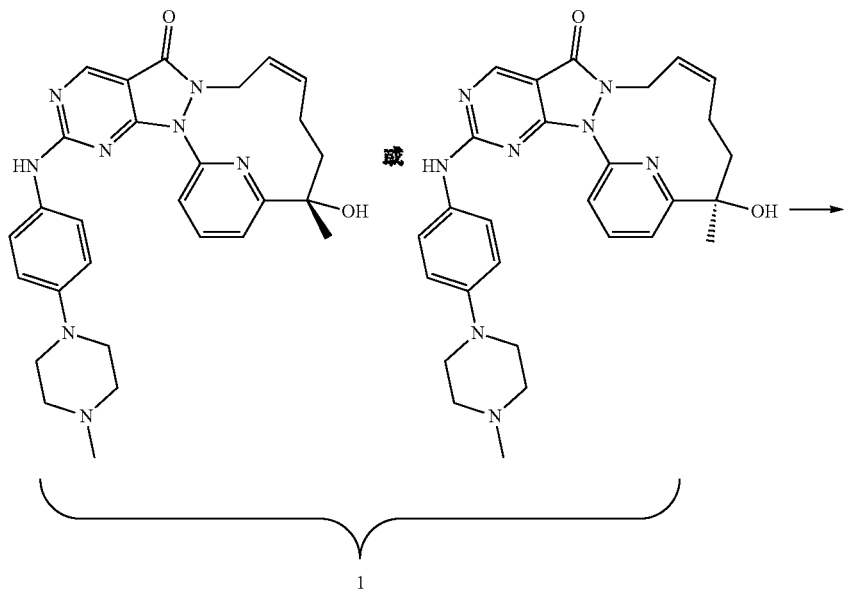

1

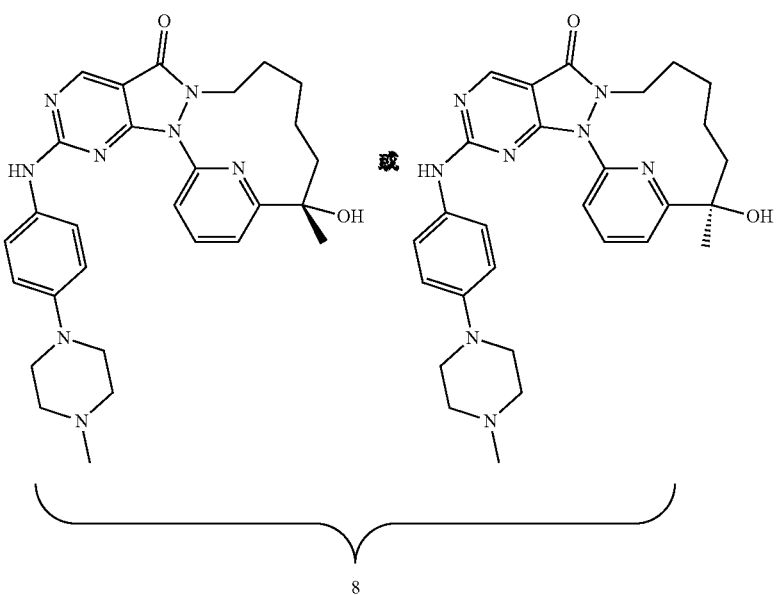

8

Step 1: Synthesis of Compound 8

Palladium on carbon (0.04 g, 10% purity) was added to anhydrous methanol (20 mL), then compound 1 (80 mg, 156.07 μmol) was added, followed by hydrogen replacement for three times and pressurized to 15 psi. The reaction solution was reacted at 25° C. for 10 hours. The reaction solution was filtered through a five-hole funnel covered with diatomite. The filter cake was washed with methanol (2×20 mL). The filtrate was dried by rotary evaporation under pressure to obtain a residue. The residue was dissolved in 2 mL of methanol and separated by HPLC (chromatographic column: Waters Xbridge 150*25 mm 5 μm; mobile phase: [water (0.05% HCl)-ACN]; B %: 15%-35%, 12 min) to obtain 8. $^1$H NMR (400 MHz, CD$_3$OD) δ=8.71 (s, 1H), 7.99-7.93 (m, 1H), 7.99-7.93 (m, 1H), 7.85 (br d, J=8.2 Hz, 1H), 7.62 (d, J=7.5 Hz, 1H), 7.52 (br d, J=8.8 Hz, 2H), 6.92 (d, J=9.0 Hz, 2H), 3.83-3.74 (m, 2H), 3.65-3.61 (m, 1H), 3.48-3.39 (m, 1H), 3.31-3.29 (m, 2H), 3.25-3.20 (m, 3H), 2.85-2.79 (m, 3H), 2.68 (s, 2H), 2.50 (s, 3H), 2.38-2.21 (m, 3H), 1.90 (br dd, J=7.3, 13.7 Hz, 1H), 1.48 (s, 3H); MS m/z: 514.62 [M+H]$^+$.

Example 7: Compound 9
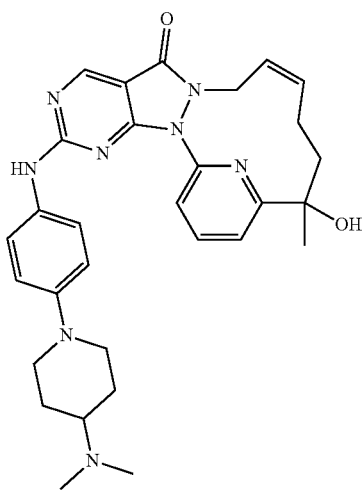 [SMILES: CN(C)C1CCN(c2ccc(Nc3ncc4c(=O)n5n(c4n3)-c3cccc(n3)C(C)(O)CC/C=C\C5)cc2)CC1]
Synthetic Route
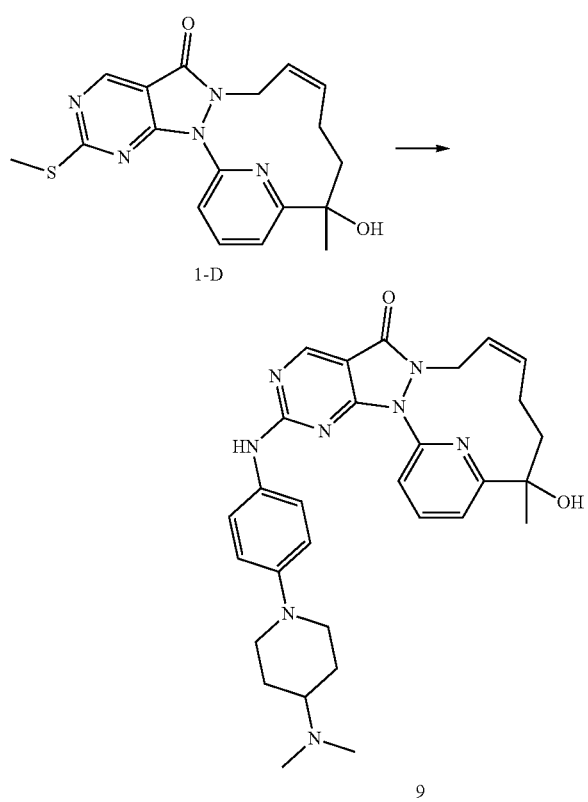
Step 1: Synthesis of Compound 9
Except that the corresponding raw materials were used, 9 was obtained in the same method as the synthesis of compound 1-E in Example 1.
$^1$H NMR (400 MHz, CDCl$_3$) δ ppm 1.69 (s, 3H) 1.80 (br s, 4H), 1.95-2.05 (m, 3H), 2.11-2.25 (m, 2H), 2.35 (s, 6H), 2.74 (br t, J=12.18 Hz, 2H), 3.72 (br d, J=11.54 Hz, 2H), 4.26 (br s, 1H), 4.50 (br d, J=13.30 Hz, 1H), 5.74 (br s, 2H), 6.95 (d, J=9.04 Hz, 2H), 7.26 (s, 1H), 7.47 (d, J=9.04 Hz, 2H), 7.80-7.91 (m, 2H), 8.86 (s, 1H); MS m/z: 541.1 [M+H]$^+$.
Example 8: Compound 10
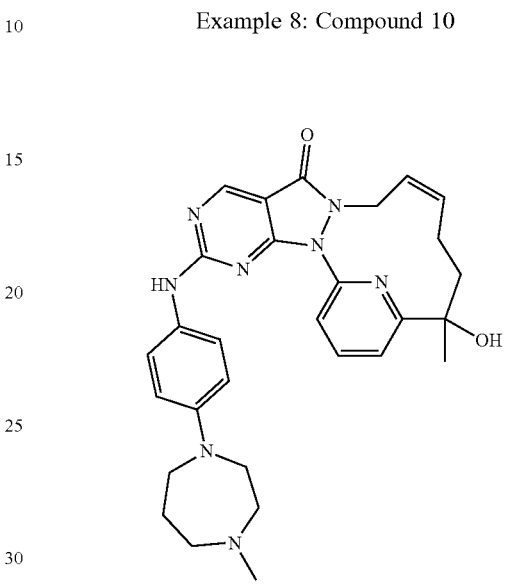
Synthetic Route
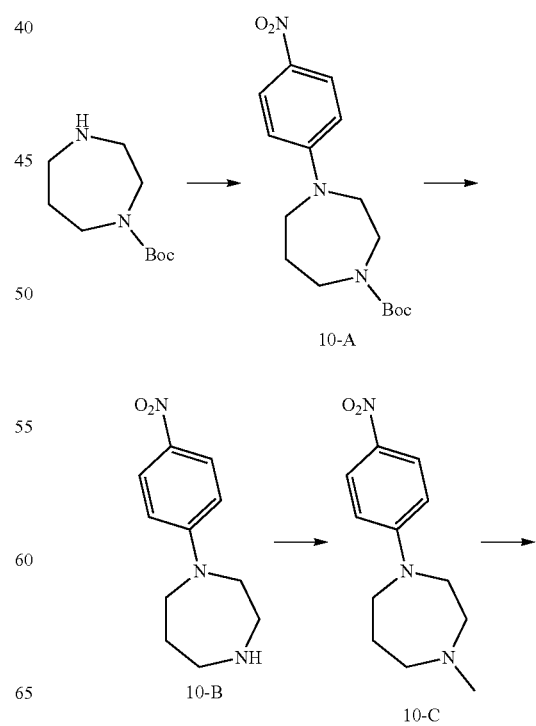

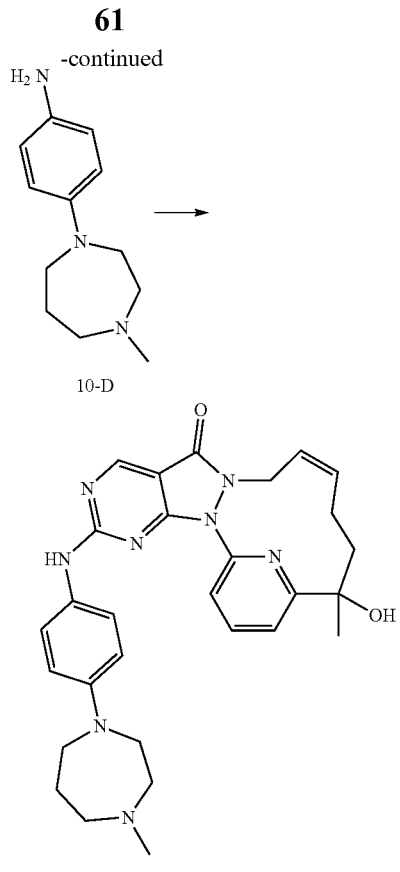

Step 1: Synthesis of Compound 10-A

To a solution of compound 1-Boc-homopiperazine (3 g, 14.98 mmol) in dimethyl sulfoxide (40 mL), p-nitrofluorobenzene (2.52 g, 14.98 mmol) and potassium carbonate (3.00 g, 21.72 mmol) were added. The reaction solution was stirred at 100° C. for 12 hours. 120 mL of water was added to the reaction solution and stirred, filtered, and the filter cake was washed with 20 mL of water, and then dried by rotary evaporation to obtain a crude product of 10-A.

$^1$H NMR (400 MHz, CDCl$_3$) δ ppm 1.36-1.46 (m, 9H), 2.00 (br d, J=5.78 Hz, 2H), 3.24-3.42 (m, 2H), 3.61-3.73 (m, 6H), 6.68 (br d, J=9.28 Hz, 2H), 8.14 (d, J=9.28 Hz, 2H).

Step 2: Synthesis of Compound 10-B

To a solution of compound 10-A (3 g, 9.34 mmol) in dichloromethane (18 mL) was added trifluoroacetic acid (9.24 g, 81.04 mmol), and the reaction solution was stirred at 30° C. for 1 hour. The reaction solution was concentrated to dryness, diluted with 20 mL of water, the aqueous phase was extracted with 30 mL of dichloromethane, the organic phase was discarded, the pH of the aqueous phase was adjusted to 11-12 with 10% sodium hydroxide solution, and the aqueous phase was extracted with dichloromethane 40 mL×3, the organic phase was washed with 40 mL of saturated brine, dried over anhydrous sodium sulfate, and filtered and the reaction solution was concentrated to dryness to obtain a crude compound 10-B. MS m/z: 220.0 [M+H]$^+$.

Step 3: Synthesis of Compound 10-C

To a solution of compound 10-B (1.87 g, 8.45 mmol) in methanol (18.00 mL) was added formaldehyde (6.72 g, 82.83 mmol), sodium borohydride acetate (3.58 g, 16.90 mmol) and acetic acid (507.54 mg, 8.45 mmol), and stirred at 30° C. for 1 hour. The pH of the reaction solution was adjusted to 5 with 2N hydrochloric acid. The reaction solution was concentrated and then the pH was adjusted to 11 with 10% sodium hydroxide, extracted with dichloromethane 50 mL×3, the organic phase was washed with saturated brine 30 mL, and dried over anhydrous sodium sulfate, filtered and concentrated to obtain a crude compound 10-C. $^1$H NMR (400 MHz, CDCl$_3$) δ ppm 1.96 (quin, J=5.90 Hz, 2H), 2.29-2.36 (m, 3H), 2.46-2.53 (m, 2H), 2.63-2.68 (m, 2H), 3.52 (t, J=6.26 Hz, 2H), 3.57-3.61 (m, 2H), 6.56 (d, J=9.54 Hz, 2H), 8.03 (d, J=9.54 Hz, 2H). MS m/z: 235.9 [M+H]$^+$.

Step 4: Synthesis of Compound 10-D

To a solution of compound 10-C (1.5 g, 6.38 mmol) in tetrahydrofuran (20 mL), palladium on carbon (760 mg, 644.07 μmol, 10% purity) was added, and the mixture was stirred at 30° C. and hydrogen pressure (15 psi) for 12 hours. After the completion of the reaction, the reaction solution was filtered through diatomite and concentrated to obtain a crude product of 10-D.

$^1$H NMR (400 MHz, CDCl$_3$) δ ppm 1.91 (dt, J=11.42, 6.08 Hz, 2H), 2.27-2.37 (m, 3H), 2.45-2.54 (m, 2H), 2.58-2.64 (m, 2H), 3.34 (t, J=6.54 Hz, 2H), 3.38-3.46 (m, 2H), 6.48-6.53 (m, 2H), 6.55-6.61 (m, 2H). MS m/z: 206.1 [M+H]$^+$.

Step 5: Synthesis of Compound 10

Except that the corresponding raw materials were used, 10 was obtained in the same method as the synthesis of compound 1-E in Example 1.

$^1$H NMR (400 MHz, CDCl$_3$) δ ppm 1.60 (s, 3H) 1.68 (br d, J=3.76 Hz, 2H), 1.94-1.99 (m, 2H), 2.00-2.17 (m, 2H), 2.33 (s, 3H), 2.47-2.59 (m, 2H), 2.63-2.70 (m, 2H), 3.43 (t, J=6.26 Hz, 2H), 3.50-3.54 (m, 2H), 4.17 (br s, 1H), 4.41 (br d, J=11.04 Hz, 1H), 5.65 (br s, 2H), 6.60 (d, J=8.78 Hz, 2H), 7.17 (br d, J=7.54 Hz, 1H), 7.31 (br d, J=8.54 Hz, 2H), 7.70-7.80 (m, 2H), 8.75 (s, 1H). MS m/z: 527.1 [M+H]$^+$.

Example 9: Compound 11

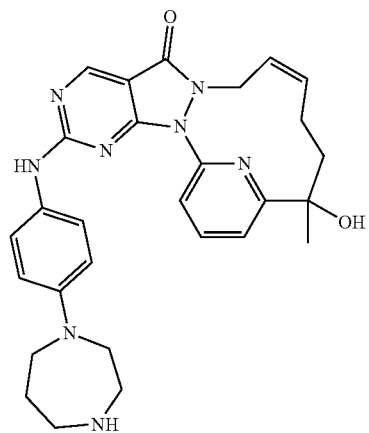 [SMILES: CC1(O)CC/C=C\Cn2c(=O)c3cnc(Nc4ccc(N5CCCNCC5)cc4)nc3n2-c2cccc1n2]

Synthetic Route

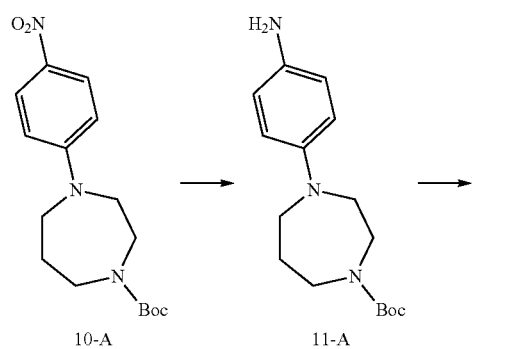

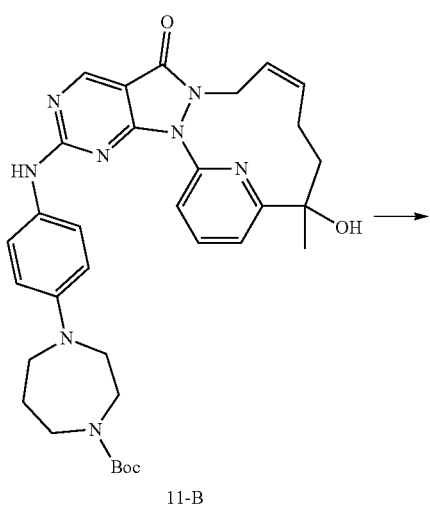

Step 1: Synthesis of Compound 11-A

Except that the corresponding raw materials were used, a crude product of 11-A was obtained in the same method as the synthesis of compound 10-D in Example 8. MS m/z: 292.1 [M+H]$^+$.

Step 2: Synthesis of Compound 11-B

Except that the corresponding raw materials were used, a crude product of 11-B was obtained in the same method as the synthesis of compound 1-E in Example 1. MS m/z: 613.3 [M+H]$^+$.

Step 3: Synthesis of Compound 11

Except that the corresponding raw materials were used, 11 was obtained in the same method as the synthesis of compound 6 in Example 4.

$^1$H NMR (400 MHz, CDCl$_3$) δ ppm 1.60 (s, 3H), 1.91-1.95 (m, 2H), 2.05-2.20 (m, 4H), 2.83-2.89 (m, 2H), 3.02-3.07 (m, 2H), 3.51-3.56 (m, 4H), 4.23 (br s, 1H) 4.41 (br d, J=13.56 Hz, 1H), 5.66 (br s, 2H), 6.61 (d, J=9.04 Hz, 2H), 7.18 (br d, J=7.54 Hz, 1H), 7.32 (br d, J=8.54 Hz, 2H), 7.71-7.79 (m, 2H), 8.75 (s, 1H). MS m/z: 613.3 [M+H]$^+$.

Example 10: Compound 12-A and Compound 12-B

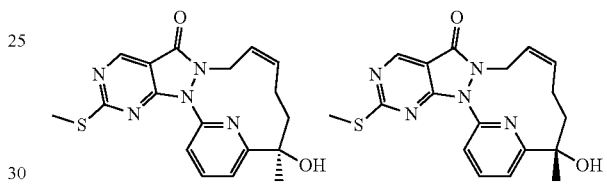

Synthetic Route

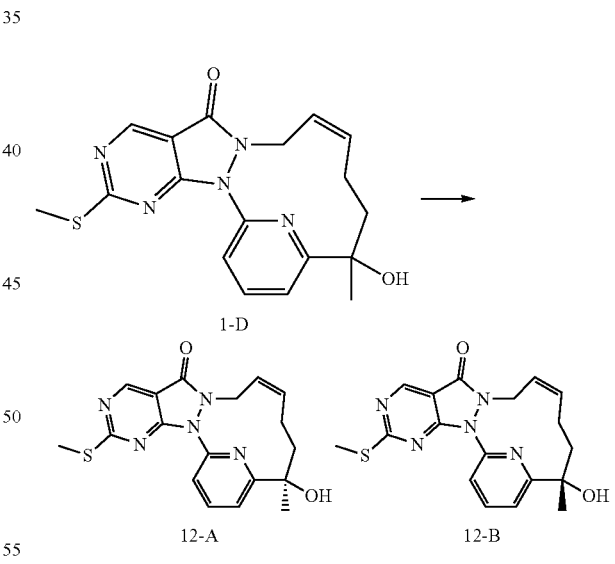

Step 1: Synthesis of Compound 12-A and Compound 12-B

Compound 1-D (3.9 g, 10.56 μmol) was subjected to SFC chiral resolution (Chromatographic column: DAICEL CHIRALPAK AS 250 mm*50 mm, I.D., 10 μm; Mobile phase: A: Supercritical CO$_2$, B: MeOH (0.1% NH$_3$H$_2$O), A: B=75: 25 at 200 mL/min) to obtain 12-A, retention time: 13.1 min.

$^1$H NMR (400 MHz, CDCl$_3$) δ=8.97 (s, 1H), 7.94-7.89 (t, 1H), 7.81 (d, 1H), 7.32 (d, J=7.3 Hz, 1H), 5.93-5.46 (br s,

2H), 4.55 (m, 1H), 4.50-4.34 (br s, 1H), 4.17 (s, 1H), 2.60 (s, 3H), 2.15 (m, J=14.1 Hz, 2H), 2.00 (m, 1H), 1.81-1.72 (m, 1H), 1.69 (s, 3H). MS m/z: 370.2 [M+H]+.

And 12-B, retention time: 16.7 min.

¹H NMR (400 MHz, CDCl₃) δ=8.97 (s, 1H), 7.95-7.88 (t, 1H), 7.81 (d, 1H), 7.32 (d, J=7.8 Hz, 1H), 6.04-5.43 (br s, 2H), 4.61-4.52 (m, 1H), 4.49-4.31 (br s, 1H), 4.17 (s, 1H), 2.60 (s, 3H), 2.15 (m, J=14.1 Hz, 2H), 2.05-1.95 (m, 1H), 1.81-1.72 (m, 1H), 1.69 (s, 3H). MS m/z: 370.1 [M+H]+.

Example 11: Compound 12

Synthetic Route

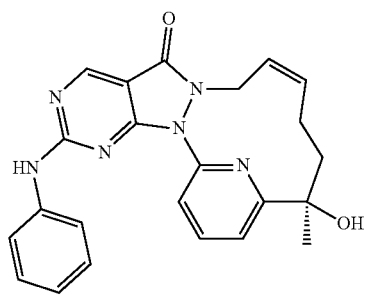 [SMILES: C[C@@]1(O)CC/C=C\Cn2c(=O)c3cnc(Nc4ccccc4)nc3n2-c2cccc1n2]

12-A

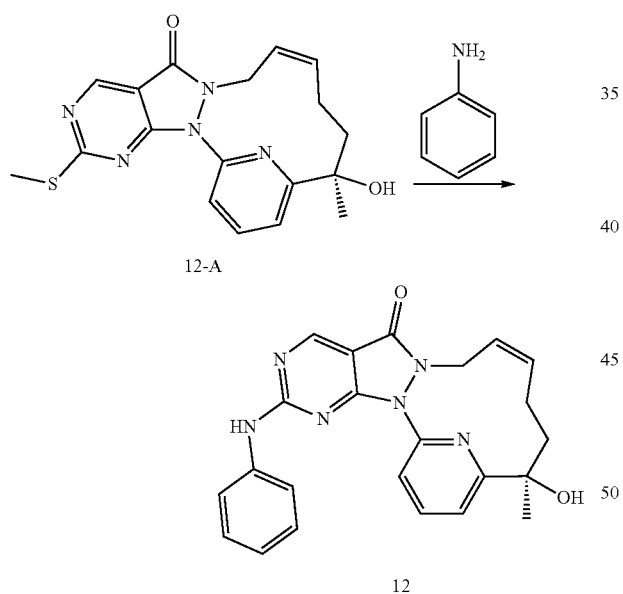

12

Step 1: Synthesis of Compound 12

Compound 12-A (0.1 g, 270.68 μcool) was dissolved in toluene (7 mL), m-chloroperoxybenzoic acid (70.07 mg, 324.82 μcool, 80% purity) was added, and the reaction was stirred at 30° C. for 1 hour. Aniline (27.73 mg, 297.75 μcool, 27.18 μL), N, N-diisopropylethylenediamine (87.46 mg, 676.70 μcool, 117.87 μL) were added to the reaction solution, and the reaction solution was stirred at 30° C. for 12 hours. 5 mL of saturated aqueous sodium sulfite solution was added to the reaction solution, and 10 mL of DCM was added for extraction. The organic phase was dried over anhydrous sodium sulfate, filtered, and dried by rotary evaporation to obtain a crude product. The crude product was separated by preparative liquid chromatography (Chromatographic column: Waters Xbridge 150*25 mm 5 μm; mobile phase: [H₂O (10 mM NH₄HCO₃)-ACN]; B %: 33%-63%, 7 min) to obtain 12.

¹H NMR (400 MHz, CDCl₃) δ=8.90 (s, 1H), 7.92-7.86 (t, 1H), 7.85-7.80 (d, 1H), 7.62 (d, J=7.9 Hz, 2H), 7.57-7.50 (br s, 1H), 7.37 (t, J=7.9 Hz, 2H), 7.30 (d, 1H), 7.13 (t, J=7.2 Hz, 1H), 5.73 (br s, 2H), 4.52 (m, J=12.6 Hz, 1H), 4.43-4.27 (br s, 1H), 4.25-4.21 (s, 1H), 2.24-2.07 (m, 2H), 2.05-1.93 (m, 1H), 1.82-1.72 (m, 1H), 1.69 (s, 3H). MS m/z: 415.2 [M+H]+.

Example 12: Compound 13

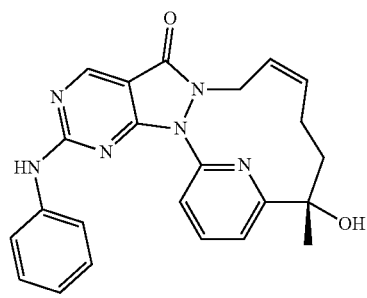 [SMILES: C[C@]1(O)CC/C=C\Cn2c(=O)c3cnc(Nc4ccccc4)nc3n2-c2cccc1n2]

Synthetic Route

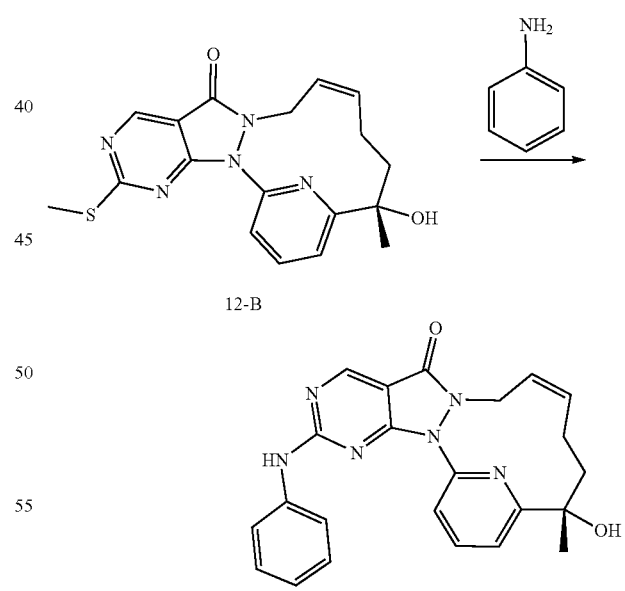

12-B

13

Step 1: Synthesis of Compound 13

Except that the corresponding raw materials were used, 13 was obtained in the same method as the synthesis of compound 12 in Example 11.

¹H NMR (400 MHz, CDCl₃) δ=8.88 (s, 1H), 7.98 (br s, 1H), 7.92-7.84 (t, 1H), 7.84-7.77 (d, 1H), 7.66-7.56 (d, 2H), 7.35 (t, J=7.3 Hz, 2H), 7.29 (d, 1H), 7.17-7.08 (t, 1H), 5.72 (br s, 2H), 4.61-4.45 (m, 1H), 4.43-4.31 (br s, 1H), 4.31-4.21 (s, 1H), 2.14 (m, J=12.3 Hz, 2H), 2.05-1.95 (m, 1H), 1.81-1.73 (m, 1H), 1.68 (s, 3H). MS m/z: 415.2 [M+H]⁺.

Example 13: Compound 14

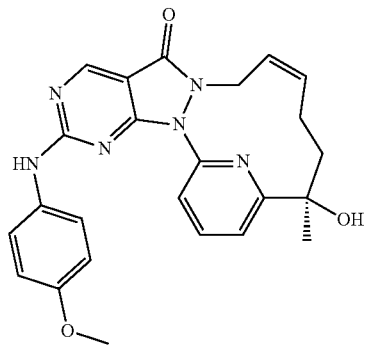 [SMILES: COc1ccc(Nc2ncc3c(=O)n4n(c3n2)-c2cccc(n2)[C@](C)(O)CC/C=C\C4)cc1]

Synthetic Route 2.23-2.07 (m, 2H), 2.05-1.93 (m, 1H), 1.81-1.72 (m, 1H), 1.68 (s, 3H). MS m/z: 445.2 [M+H]⁺.

Example 14: Compound 15

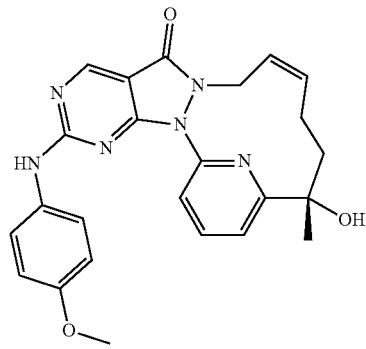 [SMILES: COc1ccc(Nc2ncc3c(=O)n4n(c3n2)-c2cccc(n2)[C@@](C)(O)CC/C=C\C4)cc1]

Synthetic Route

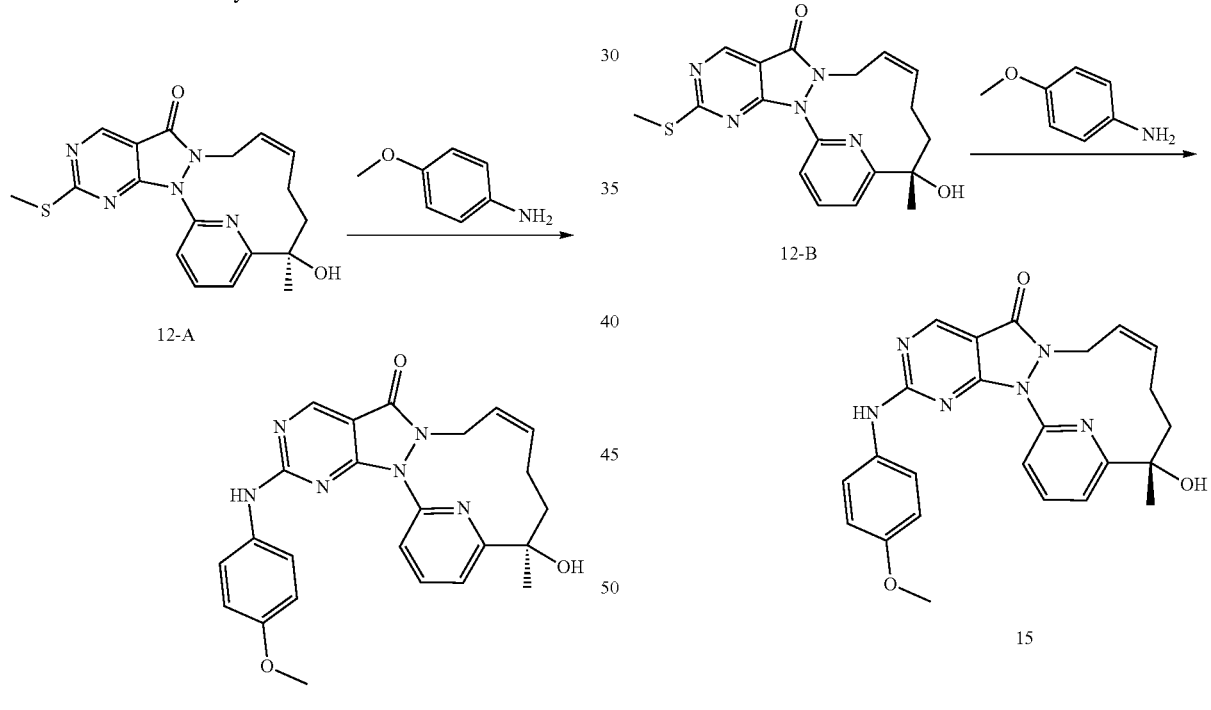

Step 1: Synthesis of Compound 14

Except that the corresponding raw materials were used, 14 was obtained in the same method as the synthesis of compound 12 in Example 11.

¹H NMR (400 MHz, CDCl₃) δ=8.86 (s, 1H), 7.89-7.83 (t, 1H), 7.82-7.76 (d, 1H), 7.49 (d, J=9.0 Hz, 2H), 7.26-7.24 (d, 1H), 6.91 (d, J=9.0 Hz, 2H), 5.74 (br s, 2H), 4.49 (m, J=12.8 Hz, 1H), 4.41-4.28 (br s, 1H), 4.23 (s, 1H), 3.83 (s, 3H),

Step 1: Synthesis of Compound 15

Except that the corresponding raw materials were used, 15 was obtained in the same method as the synthesis of compound 12 in Example 11.

¹H NMR (400 MHz, CDCl₃) δ=8.86 (s, 1H), 7.89-7.83 (t, 1H), 7.82-7.77 (d, 1H), 7.49 (d, J=8.8 Hz, 2H), 7.36 (br s, 1H), 7.26 (d, 1H), 6.91 (d, J=9.0 Hz, 2H), 5.75 (br s, 2H), 4.48 (m, 1H), 4.30 (br s, 1H), 4.23 (s, 1H), 3.84 (s, 3H), 2.15 (m, J=14.1 Hz, 2H), 2.05-1.94 (m, 1H), 1.77 (m, J=13.8 Hz, 1H), 1.68 (s, 3H). MS m/z: 445.2 [M+H]⁺.

Example 15: Compound 16

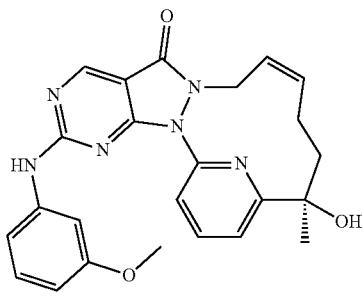 [SMILES: COc1cccc(Nc2ncc3c(=O)n4n(c3n2)-c2cccc(n2)[C@](C)(O)CC/C=C\C4)c1]

Synthetic Route

Example 16: Compound 17

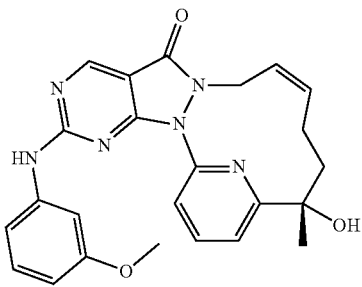 [SMILES: COc1cccc(Nc2ncc3c(=O)n4n(c3n2)-c2cccc(n2)[C@@](C)(O)CC/C=C\C4)c1]

Synthetic Route

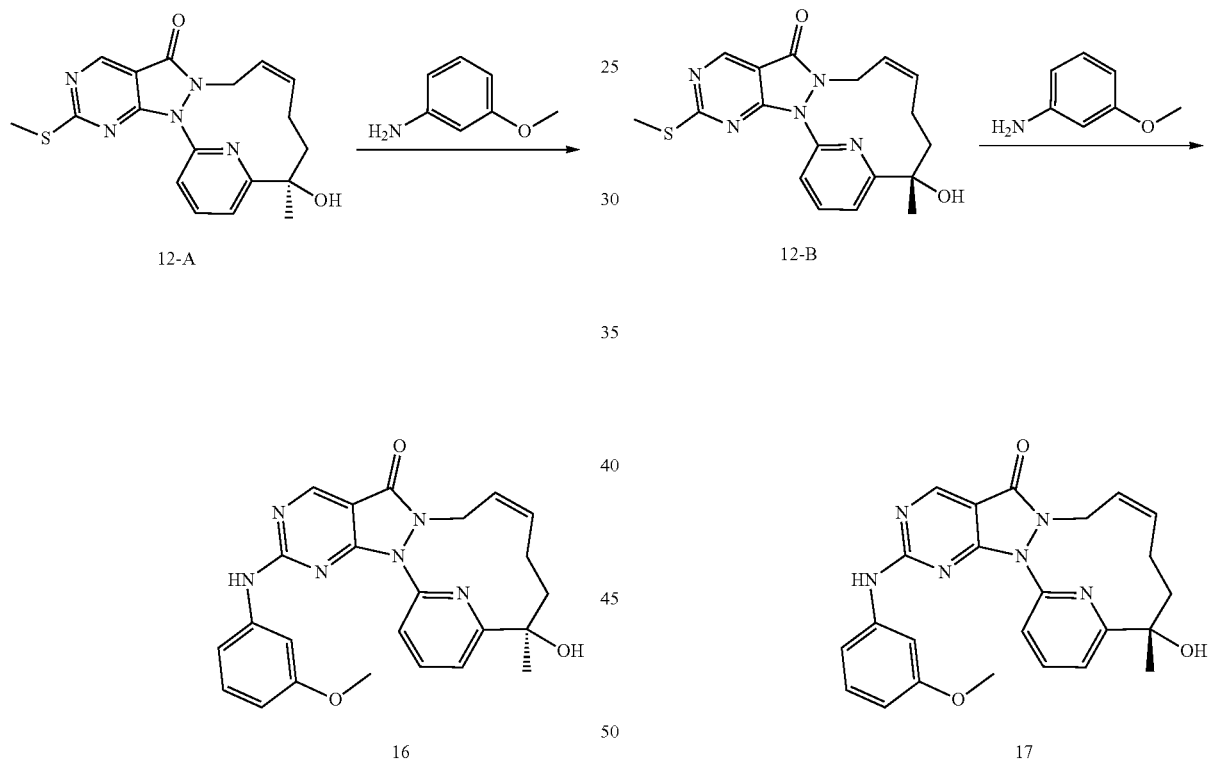

Step 1: Synthesis of Compound 15

Except that the corresponding raw materials were used, 16 was obtained in the same method as the synthesis of compound 12 in Example 11.

$^1$H NMR (400 MHz, CDCl$_3$) δ=8.90 (s, 1H), 7.92-7.87 (t, 1H), 7.87-7.83 (d, 1H), 7.50 (br s, 1H), 7.41 (t, J=2.1 Hz, 1H), 7.31-7.28 (d, 1H), 7.26-7.23 (d, 1H), 7.08 (dd, J=7.6 Hz, 1H), 6.68 (dd, J=2.0, 8.3 Hz, 1H), 5.74 (br s, 2H), 4.52 (m, J=9.0 Hz, 1H), 4.35 (br s, 1H), 4.23 (s, 1H), 3.81 (s, 3H), 2.21-2.09 (m, 2H), 2.06-1.95 (m, 1H), 1.77 (m, J=13.3 Hz, 1H), 1.69 (s, 3H). MS m/z: 445.2 [M+H]$^+$.

Step 1: Synthesis of Compound 17

Except that the corresponding raw materials are used, 17 was obtained in the same method as the synthesis of compound 12 in Example 11.

$^1$H NMR (400 MHz, CDCl$_3$) δ=8.90 (s, 1H), 7.92-7.87 (t, 1H), 7.87-7.82 (d, 1H), 7.49 (br s, 1H), 7.41 (t, J=2.1 Hz, 1H), 7.30-7.28 (d, 1H), 7.26-7.23 (d, 1H), 7.07 (dd, J=7.5 Hz, 1H), 6.68 (dd, J=1.8, 8.3 Hz, 1H), 5.74 (br s, 2H), 4.52 (m, J=14.6 Hz, 1H), 4.35 (br s, 1H), 4.22 (s, 1H), 3.81 (s, 3H), 2.22-2.08 (m, 2H), 2.06-1.93 (m, 1H), 1.82-1.73 (m, 1H), 1.69 (s, 3H). MS m/z: 445.2 [M+H]$^+$.

Example 17: Compound 18

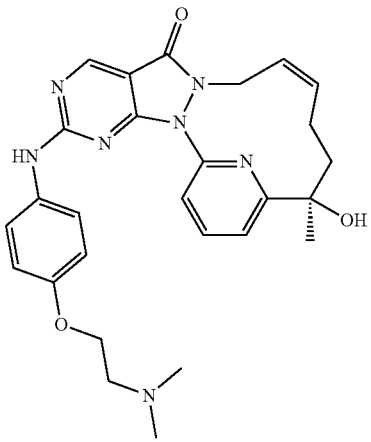 [SMILES: CN(C)CCOc1ccc(Nc2ncc3c(=O)n4n(c3n2)-c2cccc(n2)[C@](C)(O)CC/C=C\C4)cc1]

Synthetic Route

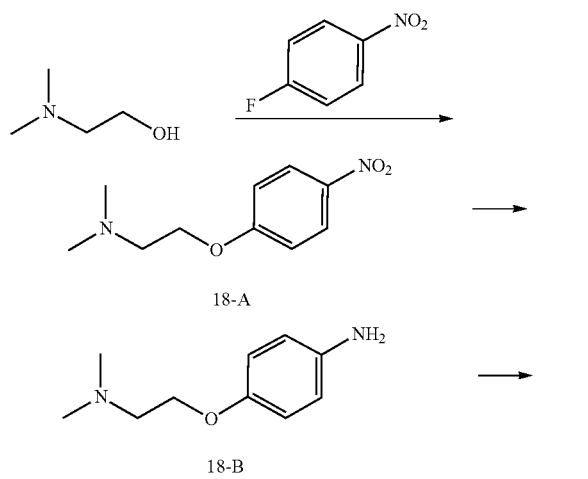

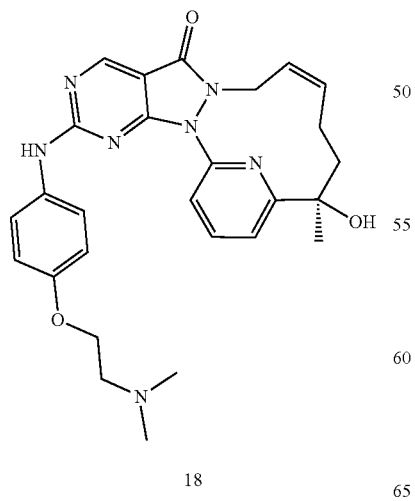

18

Step 1: Synthesis of Compound 18-A

The compound sodium hydride (1.68 g, 42.07 mmol, purity 60%) was dissolved in DMF (20 mL), and N, N-dimethylethanolamine (1.5 g, 16.83 mmol, 1.69 mL) was slowly added at 0° C. under a nitrogen atmosphere. After stirring for 1 hour, a mixture of p-fluoronitrobenzene (2.37 g, 16.83 mmol) in DMF (2 mL) was added to the reaction solution, and stirred at 15° C. under a nitrogen atmosphere for 16 hours. Saturated ammonium chloride solution (20 mL) was added to quench the reaction, extracted with ethyl acetate (20 mL×3), the organic phases were combined, washed once with saturated brine (30 mL), dried over anhydrous sodium sulfate, filtered, and dried by rotary evaporation to obtain a crude product. The crude product was separated by column chromatography (dichloromethane/methanol=10/1, TLC (dichloromethane/methanol=10/1, Rf=0.6)) to obtain 18-A. $^1$H NMR (400 MHz, DMSO-$d_6$) δ=8.22-8.17 (d, 2H), 7.15 (d, J=8.1 Hz, 2H), 4.19 (t, J=5.8 Hz, 2H), 2.64 (t, J=5.6 Hz, 2H), 2.21 (s, 6H). MS m/z: 211.0 [M+H]$^+$.

Step 2: Synthesis of Compound 18-B

Compound 18-A (1 g, 4.76 mmol) was dissolved in THF (20 mL), Pd/C (650 mg, 548.85 μmol, purity 10%) was added, followed by hydrogen replacement for three times and pressurized to 15 psi. The reaction solution was reacted at 20° C. for 16 hours. The reaction solution was filtered through a five-hole funnel covered with diatomite, the filter cake was washed with methanol (2×20 mL), and the filtrate was dried by rotary evaporation to obtain 18-B.
$^1$H NMR (400 MHz, CDCl$_3$) δ=6.79-6.74 (d, 2H), 6.65-6.60 (d, 2H), 3.99 (t, J=5.8 Hz, 2H), 2.69 (t, J=5.8 Hz, 2H), 2.32 (s, 6H). MS m/z: 181.1 [M+H]$^+$.

Step 3: Synthesis of Compound 18

Except that the corresponding raw materials were used, 18 was obtained in the same method as the synthesis of compound 12 in Example 11.
$^1$H NMR (400 MHz, CDCl$_3$) δ=8.86 (s, 1H), 7.90-7.83 (t, 1H), 7.82-7.76 (d, 1H), 7.48 (d, J=9.0 Hz, 2H), 7.37 (br s, 1H), 7.25 (d, 1H), 6.93 (d, J=8.9 Hz, 2H), 5.75 (br s, 2H), 4.49 m, J=13.3 Hz, 1H), 4.32 (br s, 1H), 4.26-4.19 (s, 1H), 4.09 (t, J=5.7 Hz, 2H), 2.76 (t, J=5.7 Hz, 2H), 2.37 (s, 6H), 2.25-2.08 (m, 2H), 2.06-1.93 (m, 1H), 1.81-1.73 (m, 1H), 1.68 (s, 3H). MS m/z: 502.3 [M+H]$^+$.

Example 18: Compound 19

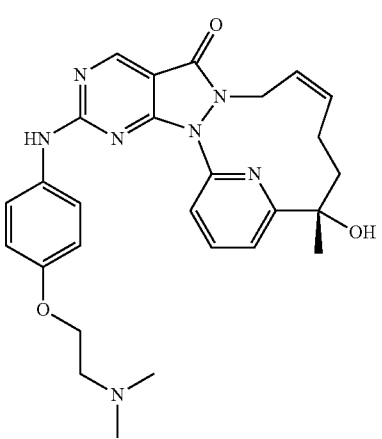 [SMILES: CN(C)CCOc1ccc(Nc2ncc3c(=O)n4n(c3n2)-c2cccc(n2)[C@@](C)(O)CC/C=C\C4)cc1]

73
Synthetic Route

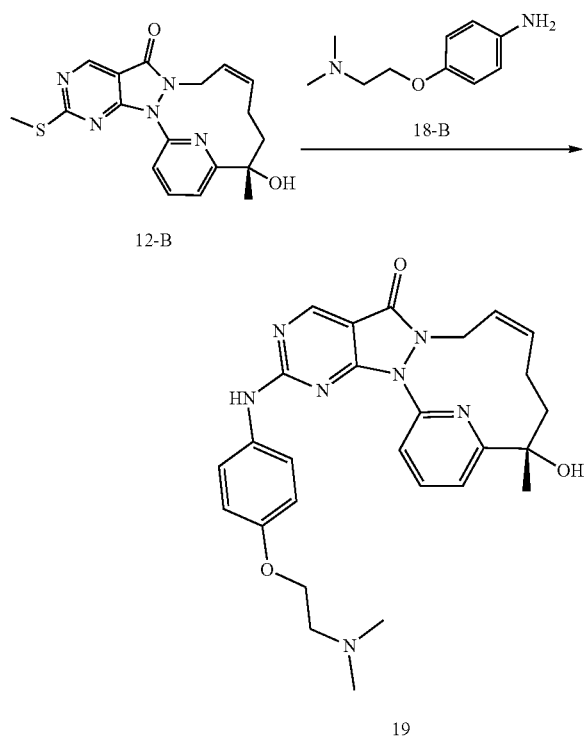

Step 1: Synthesis of Compound 19

Except that the corresponding raw materials were used, 19 was obtained in the same method as the synthesis of compound 12 in Example 11.

$^1$H NMR (400 MHz, CDCl$_3$) δ=8.85 (s, 1H), 7.89-7.83 (t, 1H), 7.82-7.75 (d, 1H), 7.65-7.52 (br s, 1H), 7.51-7.45 (d, 2H), 7.25 (d, 1H), 6.92 (d, J=9.0 Hz, 2H), 5.74 (br s, 2H), 4.49 (m, J=12.8 Hz, 1H), 4.39-4.29 (br s, 1H), 4.28-4.16 (s, 1H), 4.08 (t, J=5.7 Hz, 2H), 2.75 (t, J=5.7 Hz, 2H), 2.36 (s, 6H), 2.22-2.08 (m, 2H), 2.05-1.93 (m, 1H), 1.77 (m, J=4.6 Hz, 1H), 1.68 (s, 3H). MS m/z: 502.3 [M+H]$^+$.

Example 19: Compound 20

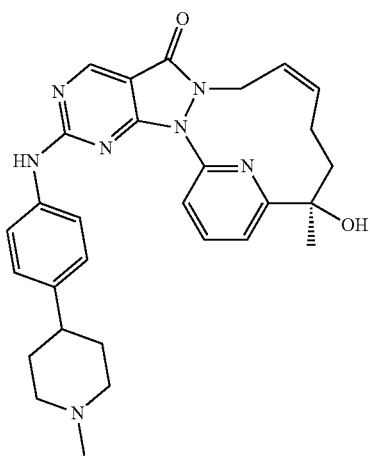 [SMILES: CN1CCC(c2ccc(Nc3ncc4c(=O)n5n(c4n3)-c3cccc(n3)[C@](C)(O)CC/C=C\C5)cc2)CC1]

74
Synthetic Route

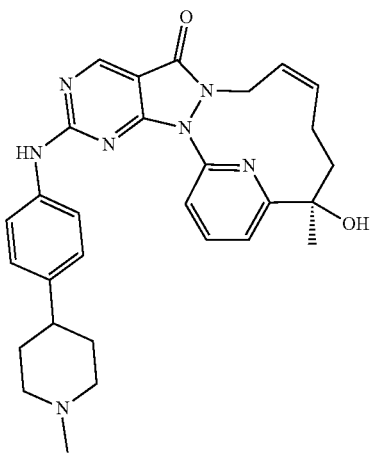

Step 1: Synthesis of Compound 20

Except that the corresponding raw materials were used, 20 was obtained in the same method as the synthesis of compound 12 in Example 11.

$^1$H NMR (400 MHz, CDCl$_3$) δ=8.88 (s, 1H), 7.90-7.85 (t, 1H), 7.84-7.79 (d, 1H), 7.54 (d, J=8.5 Hz, 2H), 7.52-7.45 (br s, 1H), 7.31-7.27 (d, 1H), 7.22 (d, J=8.5 Hz, 2H), 5.75 (br s, 2H), 4.51 (m, J=13.8 Hz, 1H), 4.41-4.28 (br s, 1H), 4.27-4.20 (s, 1H), 3.00 (d, J=11.5 Hz, 2H), 2.48 (m, J=5.6, 10.6 Hz, 1H), 2.34 (s, 3H), 2.23-2.12 (m, 2H), 2.11-2.03 (m, 3H), 1.99 (m, J=10.5 Hz, 1H), 1.84 (m, J=3.5, 9.8 Hz, 3H), 1.78-1.72 (m, 1H), 1.69 (s, 3H). MS m/z: 512.5 [M+H]$^+$.

Example 20: Compound 21
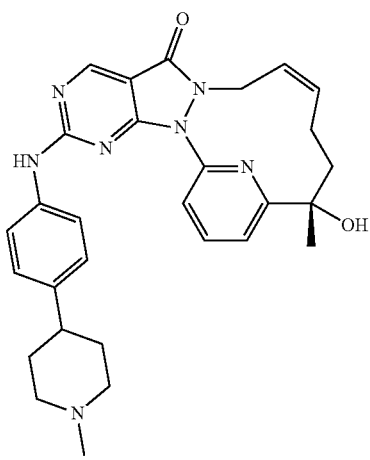 [SMILES: CN1CCC(c2ccc(Nc3ncc4c(=O)n5n(c4n3)-c3cccc(n3)[C@@](C)(O)CC/C=C\C5)cc2)CC1]
Synthetic Route
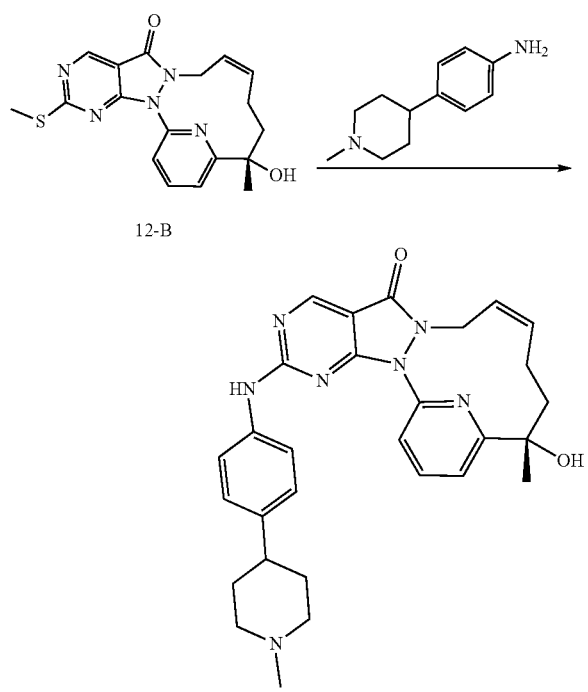
Step 1: Synthesis of Compound 21
Except that the corresponding raw materials were used, 21 was obtained in the same method as the synthesis of compound 12 in Example 11.
$^1$H NMR (400 MHz, CDCl$_3$) δ=8.88 (s, 1H), 7.90-7.85 (t, 1H), 7.84-7.77 (d, 1H), 7.61 (br s, 1H), 7.57-7.51 (d, 2H), 7.29 (d, 1H), 7.24-7.19 (d, 2H), 5.73 (br s, 2H), 4.51 (m, J=12.9 Hz, 1H), 4.43-4.29 (br s, 1H), 4.28-4.18 (m, 1H), 3.00 (d, J=11.4 Hz, 2H), 2.49 (m, J=5.2, 10.7 Hz, 1H), 2.34 (s, 3H), 2.23-2.12 (m, 2H), 2.12-2.03 (m, 3H), 2.02-1.93 (m, 1H), 1.84 (m, J=3.5, 9.6 Hz, 3H), 1.76-1.73 (m, 1H), 1.69 (s, 3H). MS m/z: 512.4 [M+H]$^+$.
Example 21: Compound 22
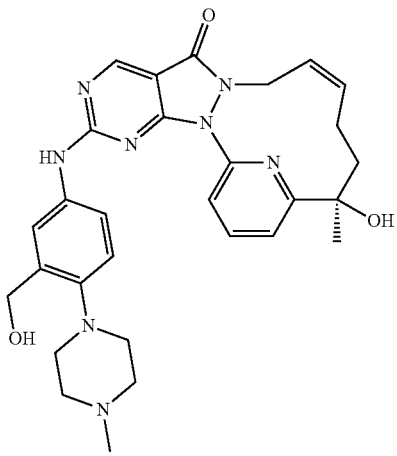 [SMILES: CN1CCN(c2ccc(Nc3ncc4c(=O)n5n(c4n3)-c3cccc(n3)[C@](C)(O)CC/C=C\C5)cc2CO)CC1]
Synthetic Route
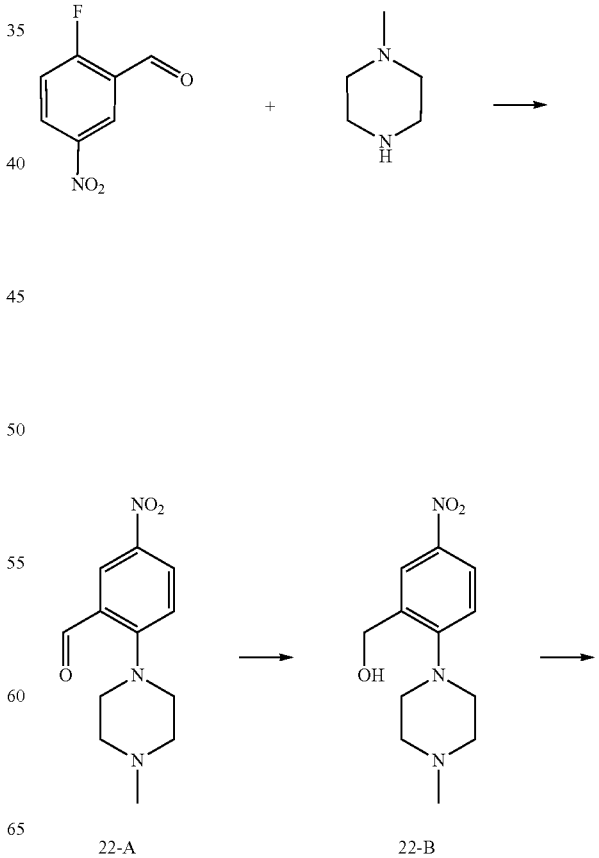

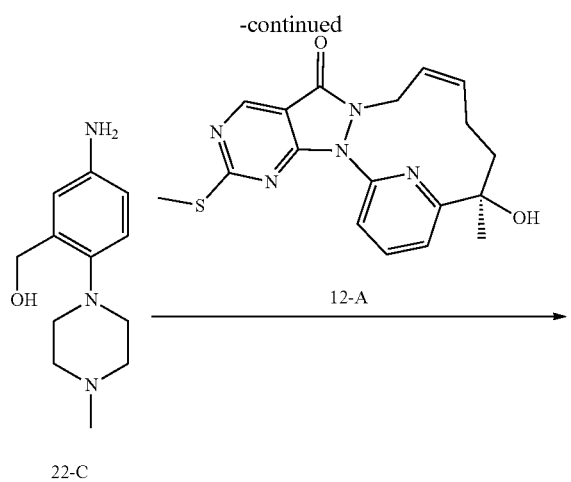

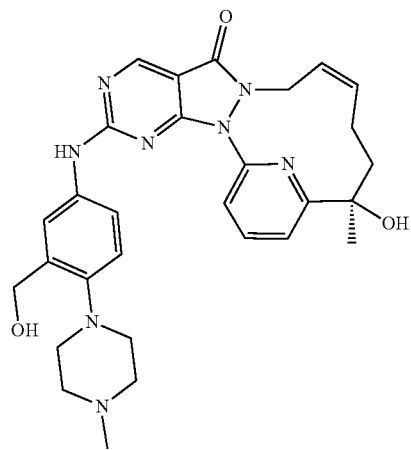

Step 1: Synthesis of Compound 22-A

2-Fluoro-5-nitro-benzaldehyde (8 g, 47.31 mmol), 1-methylpiperazine (9.48 g, 94.61 mmol, 10.49 mL), potassium carbonate (13.08 g, 94.61 mmol) and N, N-dimethylformamide (20 mL) were added to a reaction flask. Then the mixture was reacted at 90° C. for 2 hours. The reaction system was cooled to room temperature, water (40 mL) was added, extracted with ethyl acetate (40 mL), washed with water (3×30 mL) and saturated brine (30 mL), dried over anhydrous sodium sulfate, filtered, and concentrated under reduced pressure to obtain a crude product. The crude product was separated by flash column chromatography (silica gel mesh number: 200 mesh; petroleum ether:ethyl acetate=1:1 to 0:1), and purified to obtain compound 22-A.
$^1$H NMR (400 MHz, CDCl$_3$) δ=10.11 (s, 1H), 8.64 (d, J=2.9 Hz, 1H), 8.31 (dd, J=2.9, 9.0 Hz, 1H), 7.10 (d, J=9.0 Hz, 1H), 3.40-3.31 (m, 4H), 2.70-2.62 (m, 4H), 2.40 (s, 3H).

Step 2: Synthesis of Compound 22-B

22-A (2.4 g, 9.63 mmol) and THF (20 mL) were added to a reaction flask, then the system was cooled to 0° C. in an ice bath, followed by addition of sodium borohydride (910.59 mg, 24.07 mmol) and methanol (6 mL), the reaction system was stirred and reacted at 25° C. for 2 hours. The reaction system was cooled to 0° C. in an ice-water bath, and water (50 mL) was slowly added and stirred for 10 min to quench the reaction, and the reaction solution was extracted with dichloromethane (3×50 mL). The organic phases were combined, washed with saturated brine (2×50 mL), dried over anhydrous sodium sulfate, filtered, and concentrated under reduced pressure to obtain a crude product, which was separated by flash column chromatography (silica gel mesh number: 200 mesh; petroleum ether:ethyl acetate=1:1 to 0:1), purified to obtain compound 22-B. LCMS (ESI) (5-95AB): m/z: 251.28 [M+1]; $^1$H NMR (400 MHz, CDCl$_3$) δ=8.28 (d, J=2.8 Hz, 1H), 8.15 (dd, J=2.8, 8.8 Hz, 1H), 7.16 (d, J=8.8 Hz, 1H), 4.81 (s, 2H), 3.09 (t, J=4.8 Hz, 4H), 2.63 (br s, 4H), 2.39 (s, 3H).

Step 3: Synthesis of Compound 22-C

Compound 22-B (0.5 g, 1.99 mmol) and methanol (20 mL) were added to a pre-dried single-necked bottle, saturated with nitrogen and then palladium on carbon (0.08 g, purity 10%) was added, followed by nitrogen replacement for three times, then hydrogen replacement for three times and pressurization to 15 psi. The reaction solution was stirred at 25° C. for 2 hours. 10 mL of tetrahydrofuran was added to the reaction system for dilution, the reaction solution was passed through a five-hole funnel covered with diatomite, and the filter cake was washed with tetrahydrofuran (5×10 mL). The filtrates were combined and concentrated under reduced pressure to obtain compound 22-C. LCMS (ESI) m/z: 221.30 [M+1]; $^1$H NMR (400 MHz, CDCl$_3$) δ=7.07 (d, J=8.4 Hz, 1H), 6.58 (dd, J=2.6, 8.4 Hz, 1H), 6.46 (d, J=2.6 Hz, 1H), 4.71 (s, 2H), 3.58-3.57 (m, 1H), 3.59 (br s, 1H), 2.96 (t, J=4.8 Hz, 4H), 2.72-2.48 (m, 4H), 2.36 (s, 3H), 1.30-1.22 (m, 1H).

Step 4: Synthesis of Compound 22

Intermediate 12-A (150 mg, 406.02 μmol), toluene (8 mL), m-chloroperoxybenzoic acid (203.61 mg, 1.00 mmol, purity 85%) were added to a reaction flask, and the reaction solution was stirred and reacted at 25° C. for 1.5 hours, then compound 22-C (89.9 mg, 406.02 μmol) and N, N-diisopropylethylamine (131.19 mg, 1.02 mmol, 176.80 μL) were added, the reaction solution was stirred and reacted for 10 hours. The reaction system was added with 10 mL of saturated sodium sulfite solution, and extracted with 10 mL of ethyl acetate, the organic phase was washed with 10 mL of saturated brine, dried over anhydrous sodium sulfate, concentrated under pressure and dried by rotary evaporation to obtain a crude product, which was separated by HPLC (chromatographic column: Waters Xbridge 150 mm*25 mm 5 μm; mobile phase: [water (0.05% HCl)-acetonitrile]; B %: 10%-30%, 12 min), then saturated sodium bicarbonate solution was added to adjust the pH to 7, and followed by concentration under reduced pressure to remove acetonitrile. The solution was extracted with dichloromethane (3×10 mL), the organic phase was dried over anhydrous sodium sulfate, and concentrated by rotary evaporation under reduced pressure to give a product, which was purified by silica gel plate of thin-layer chromatography (dichloromethane:methanol=10:1) to obtain compound 22. LCMS (ESI): m/z: 542.63 [M+1]; $^1$H NMR (400 MHz, CDCl$_3$) δ=8.87 (s, 1H), 7.98-7.89 (m, 1H), 7.83 (br d, J=7.9 Hz, 1H), 7.71-7.57 (m, 2H), 7.39 (br d, J=8.6 Hz, 1H), 7.30 (br d, J=7.7 Hz, 1H), 7.22 (d, J=8.6 Hz, 1H), 5.74 (br s, 2H), 4.78 (d, J=5.1 Hz, 2H), 4.51 (br d, J=12.8 Hz, 1H), 4.35 (br s, 1H), 3.07 (br s, 4H), 2.73 (br s, 4H), 2.45 (s, 3H), 2.22-2.10 (m, 2H), 2.06-1.93 (m, 1H), 1.77 (br d, J=13.5 Hz, 1H), 1.69 (s, 3H), 1.26 (s, 1H).

Example 22: Compound 23

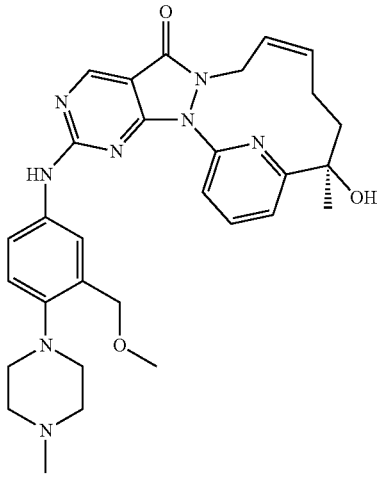 [SMILES: COCc1cc(Nc2ncc3c(=O)n4n(c3n2)-c2cccc(n2)[C@](C)(O)CC/C=C\C4)ccc1N1CCN(C)CC1]

Synthetic Route

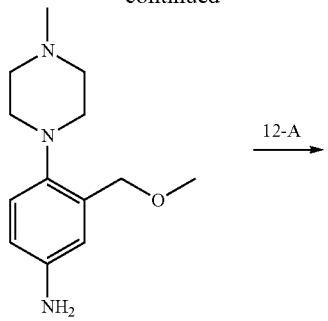

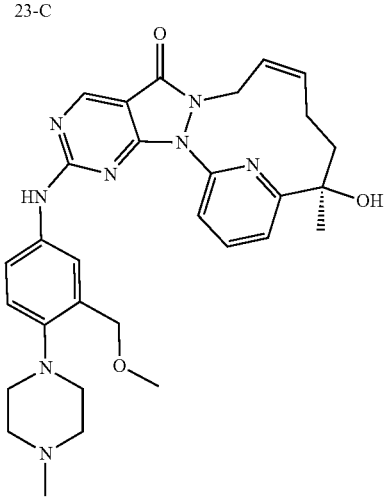

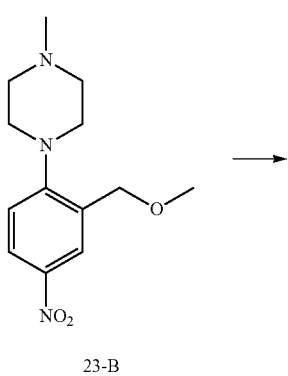

Step 1. Synthesis of Compound 23-A

Compound 22-B (450 mg, 1.79 mmol) and sulfoxide chloride (426.11 mg, 3.58 mmol, 259.82 μL) were dissolved in chloroform (10 mL), and the reaction solution was stirred and reacted at 25° C. for 0.5 hour. The reaction system was placed in an ice water bath, and a saturated aqueous solution of sodium carbonate was slowly added dropwise to adjust the pH to 7-8. The reaction system was extracted with ethyl acetate (20 mL), washed with water (3×10 mL), dried over anhydrous sodium sulfate, filtered, and concentrated under reduced pressure to obtain compound 23-A. LCMS (ESI): m/z: 269.73 [M+1].

Step 2: Synthesis of Compound 23-B

Compound 23-A (0.465 g, 1.72 mmol) was dissolved in anhydrous MeOH (5 mL), after dissolution, sodium methoxide (372.51 mg, 6.90 mmol) was added, and then the reaction system was placed in an oil bath and heated to 60° C., stirred and reacted for 2 hours. The reaction system was cooled to room temperature, water (10 mL) was added, methanol was removed by rotary evaporation under reduced pressure, and then the reaction system was extracted with ethyl acetate (3×10 mL), the organic phases were combined and washed with saturated brine (2×10 mL), dried over anhydrous sodium sulfate, filtered, and concentrated under reduced pressure to obtain a residue. The residue was purified by silica gel plate of thin layer chromatography to obtain compound 23-B. LCMS (ESI): m/z: 265.31[M+1].

Step 3: Synthesis of Compound 23-C

Compound 23-B (0.107 g, 403.31 μcool) was dissolved in anhydrous tetrahydrofuran (4 mL), saturated with nitrogen and palladium on carbon (0.05 g, purity 10%) was added, followed by nitrogen replacement for three times, then hydrogen replacement for three times and pressurization to 15 psi. The reaction solution was stirred and reacted at 25° C. for 0.5 hour. 10 mL of anhydrous tetrahydrofuran was added to the reaction system for dilution, the reaction solution was passed through a five-hole funnel covered with diatomite, and the filter cake was washed with anhydrous tetrahydrofuran (3×10 mL). The filtrates were combined and concentrated under reduced pressure to obtain compound 23-C. LCMS (ESI): m/z: 235.32[M+1].

Step 4: Synthesis of Compound 23

Toluene (5 mL) and m-chloroperoxybenzoic acid (124.23 mg, 611.92 μcool, purity 85%) were added to intermediate 12-A (113.03 mg, 305.96 μmol). After stirring and reacting at 25° C. for 2 hours, compound 23-C (72 mg, 305.96 μmol), N, N-diisopropylethylamine (98.86 mg, 764.90 μmol, 133.23 μL) were added, and then the reaction solution was stirred and reacted for 10 hours. The reaction system was added with 10 mL of saturated sodium sulfite solution, extracted with 10 mL of ethyl acetate, and the organic phase was washed with 10 mL of saturated saline, dried over anhydrous sodium sulfate, concentrated under pressure and dried by rotary evaporation to obtain a crude product. The crude product was dissolved in 1 mL of methanol and separated by HPLC (chromatographic column: Waters Xbridge 150*25 5 μm; mobile phase: [water (0.05% HCl)-acetonitrile]; B %: 15%-30%, 12 min), saturated sodium bicarbonate solution was added to adjust the pH to 7, acetonitrile was removed by rotary evaporation under reduced pressure, the solution was extracted with dichloromethane (3×10 ml), the organic phase was dried over anhydrous sodium sulfate, and concentrated by rotary evaporation under reduced pressure to obtain compound 23. LCMS (ESI): m/z: 556.66[M+1]. $^1$H NMR (400 MHz, CDCl$_3$) δ=8.79 (s, 1H), 7.87-7.65 (m, 3H), 7.38 (br d, J=6.8 Hz, 1H), 7.19 (br d, J=2.6 Hz, 1H), 7.01 (d, J=8.5 Hz, 1H), 5.65 (br s, 2H), 4.46 (s, 2H), 3.41-3.41 (m, 1H), 3.38 (d, J=17.8 Hz, 3H), 3.40-3.32 (m, 1H), 2.89 (br t, J=4.6 Hz, 4H), 2.56 (br s, 4H), 2.33 (s, 3H), 2.11-2.02 (m, 2H), 1.99-1.85 (m, 2H), 1.60 (s, 3H).

Example 23: Compound 24

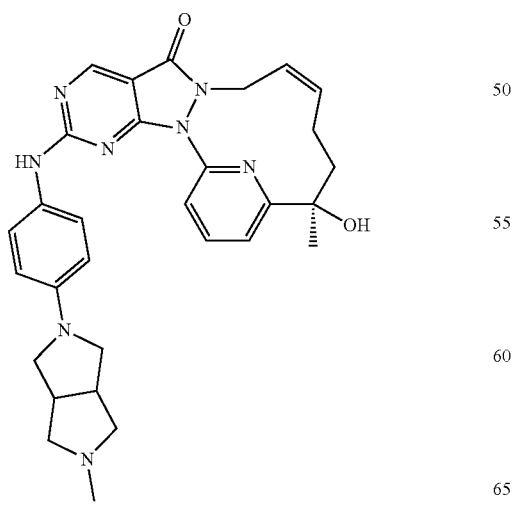

Synthetic Route

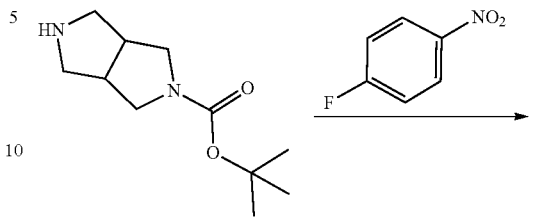

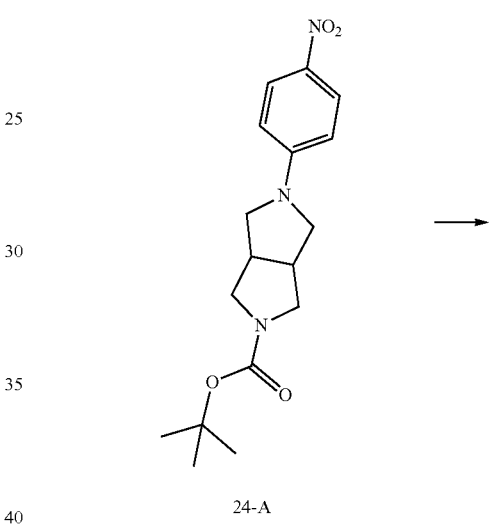

24-A

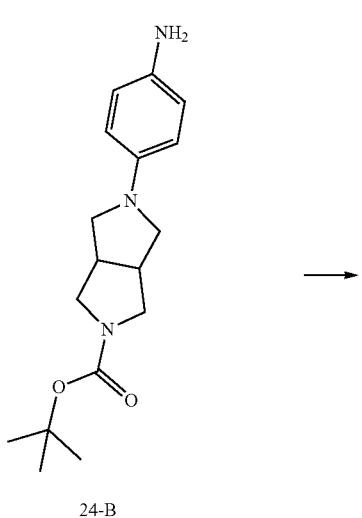

24-B

-continued

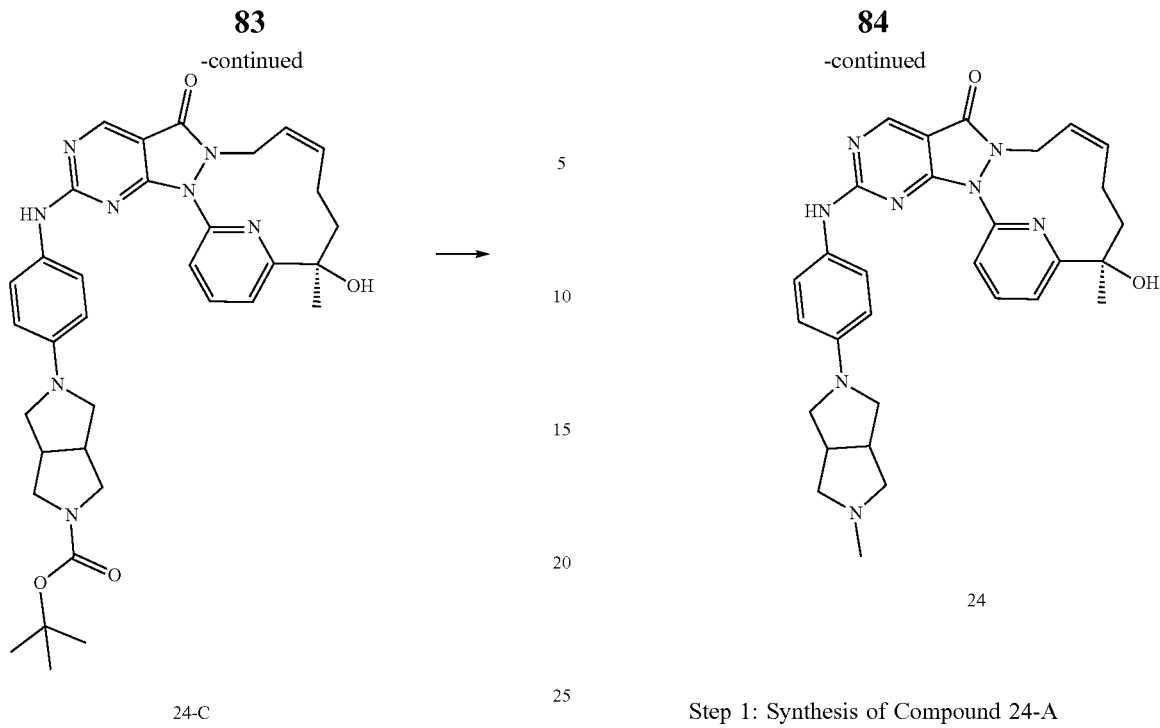

24

Step 1: Synthesis of Compound 24-A

Compound 2-BOC-hexahydro-pyrrolo [3,4-c] pyrrole (650 mg, 3.06 mmol) and p-fluoronitrobenzene (475.23 mg, 3.37 mmol) were dissolved in DMSO (15 mL) and $K_2CO_3$ (846.34 mg, 6.12 mmol) was added. Then the mixture was stirred at 60° C. for 12 hours. 50 mL of water was added slowly and stirred for 10 minutes, filtered, and the filter cake was dried by rotary evaporation to obtain 24-A.

$^1$H NMR (400 MHz, DMSO-$d_6$) δ=8.06 (d, J=9.0 Hz, 2H), 6.62 (d, J=9.3 Hz, 2H), 3.62 (m, 2H), 3.58-3.48 (m, 2H), 3.32-3.26 (m, 2H), 3.17 (m, 2H), 3.09-2.96 (m, 2H), 1.39 (s, 9H). MS m/z: 278.1 [M+H−56]$^+$.

Step 2: Synthesis of Compound 24-B

Except that the corresponding raw materials were used, 24-B was obtained in the same method as the synthesis of compound 18-B in Example 17.

$^1$H NMR (400 MHz, DMSO-$d_6$) δ=6.48 (d, J=8.8 Hz, 2H), 6.37 (d, J=8.8 Hz, 2H), 4.32 (s, 2H), 3.51 (m, 2H), 3.20 (m, J=7.5 Hz, 2H), 3.18-3.10 (m, 2H), 3.01 (m, J=10.5 Hz, 2H), 2.96-2.86 (m, 2H), 1.38 (s, 9H). MS m/z: 304.2 [M+H]$^+$.

Step 3: Synthesis of Compound 24-C

Except that the corresponding raw materials were used, 24-C was obtained in the same method as the synthesis of compound 12 in Example 11.

$^1$H NMR (400 MHz, CDCl$_3$) δ=8.83 (s, 1H), 7.89-7.84 (t, 1H), 7.83-7.79 (d, 1H), 7.41 (d, J=8.0 Hz, 2H), 7.24 (d, 1H), 6.55 (d, J=8.8 Hz, 2H), 5.74 (br s, 2H), 4.47 (m, 1H), 4.40-4.27 (br s, 1H), 4.26-4.21 (s, 1H), 3.67 (m, 2H), 3.55 (m, 2H), 3.42 (m, 1H), 3.24 (m, J=9.8 Hz, 3H), 3.03 (m, 2H), 2.15 (m, J=14.0 Hz, 2H), 2.06-1.97 (m, 1H), 1.77 (m, J=14.1 Hz, 1H), 1.68 (s, 3H), 1.47 (s, 9H). MS m/z: 625.4 [M+H]$^+$.

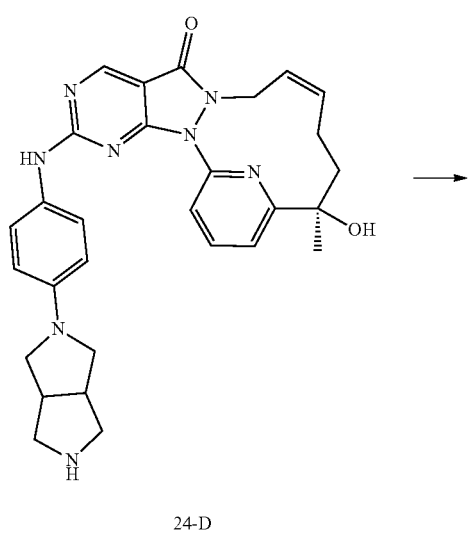

24-D

Step 4: Synthesis of Compound 24-D

Except that the corresponding raw materials were used, 24-D was obtained in the same method as the synthesis of compound 22-D in Example 21. MS m/z: 525.2 [M+H]$^+$.

Step 5: Synthesis of Compound 24

Except that the corresponding raw materials were used, 24 was obtained in the same method as the synthesis of compound 22 in Example 21.

$^1$H NMR (400 MHz, CDCl$_3$) δ=8.82 (s, 1H), 7.88-7.83 (t, 1H), 7.83-7.76 (d, 1H), 7.65 (br s, 1H), 7.40 (d, J=8.6 Hz, 2H), 7.24 (d, J=7.4 Hz, 1H), 6.65 (d, J=8.9 Hz, 2H), 5.73 (br s, 2H), 4.48 (m, J=10.9 Hz, 1H), 4.40-4.09 (m, 2H), 3.35 (m, J=5.5 Hz, 2H), 3.27-3.20 (m, 2H), 3.05-2.96 (m, 2H), 2.88-2.75 (m, 2H), 2.46 (m, J=7.8 Hz, 2H), 2.37 (s, 3H), 2.14 (m, J=14.0 Hz, 2H), 2.00 (m, J=9.1 Hz, 1H), 1.80-1.72 (m, 1H), 1.67 (s, 3H). MS m/z: 539.5 [M+H]$^+$.

Example 24: Compound 25

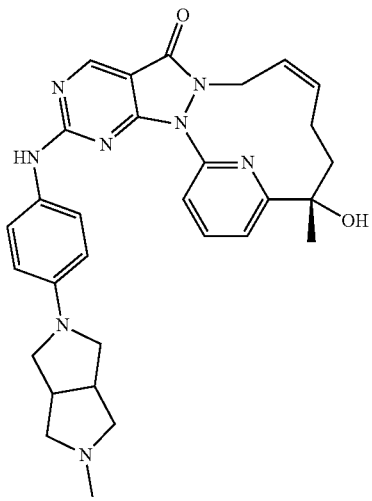 [SMILES: CN1CC2CN(c3ccc(Nc4ncc5c(=O)n6n(c5n4)-c4cccc(n4)[C@@](C)(O)CC/C=C\C6)cc3)CC2C1]

Synthetic Route

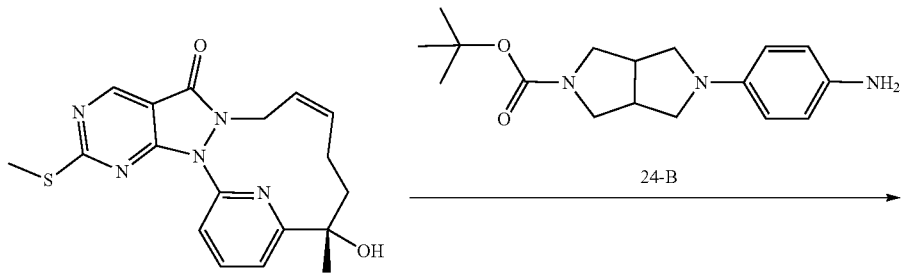

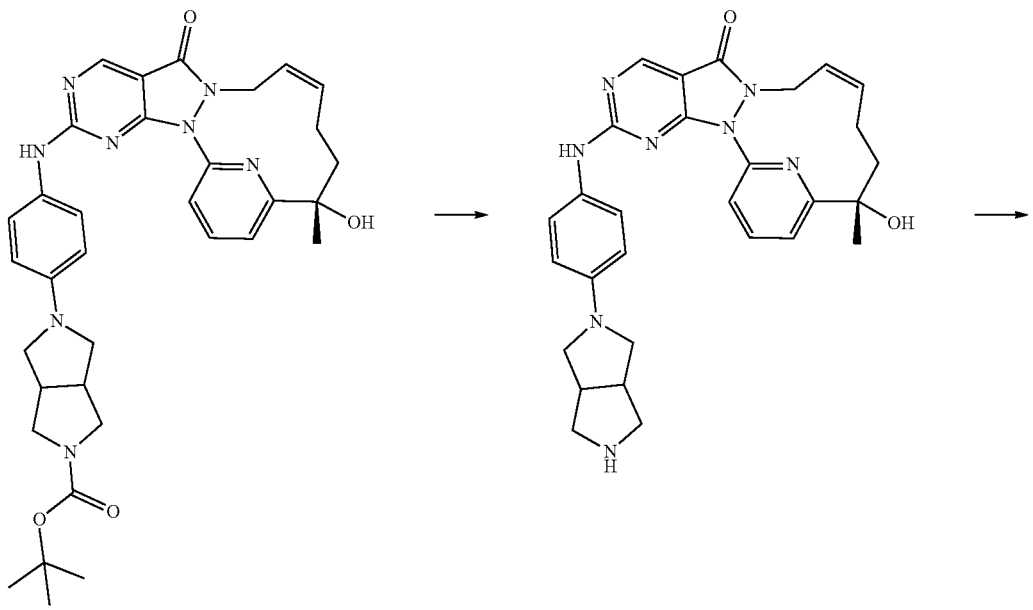

Step 1: Synthesis of Compound 25-A

Except that the corresponding raw materials were used, 25-A was obtained in the same method as the synthesis of compound 12 in Example 11.

$^{1}$H NMR (400 MHz, CDCl$_3$) δ=8.83 (s, 1H), 7.89-7.84 (t, 1H), 7.84-7.79 (d, 1H), 7.41 (d, J=8.1 Hz, 2H), 7.24 (d, 1H), 6.55 (d, J=8.9 Hz, 2H), 5.91-5.50 (br s, 2H), 4.46 (m, 1H), 4.39-4.27 (m, 1H), 4.26-4.22 (s, 1H), 3.67 (m, 2H), 3.54 (m, 2H), 3.42 (m, 1H), 3.24 (m, J=9.4 Hz, 3H), 3.02 (m, 2H), 2.22-2.09 (m, 2H), 2.07-1.96 (m, 1H), 1.77 (m, J=13.4 Hz, 1H), 1.68 (s, 3H), 1.47 (s, 9H). MS m/z: 625.4 [M+H]$^+$.

Step 2: Synthesis of Compound 25-B

Except that the corresponding raw materials were used, 25-B was obtained in the same method as the synthesis of compound 22-D in Example 21. MS m/z: 525.3 [M+H]$^+$.

Step 3: Synthesis of Compound 25

Except that the corresponding raw materials were used, 25 was obtained in the same method as the synthesis of compound 22 in Example 21.

$^{1}$H NMR (400 MHz, CDCl$_3$) δ=8.82 (s, 1H), 7.88-7.83 (t, 1H), 7.82-7.76 (d, 1H), 7.40 (d, J=8.6 Hz, 2H), 7.24 (d, J=7.3 Hz, 1H), 6.65 (d, J=8.8 Hz, 2H), 5.73 (br s, 2H), 4.47 (m, J=12.9 Hz, 1H), 4.38-4.08 (m, 2H), 3.41-3.30 (m, 2H), 3.26-3.18 (m, 2H), 2.99 (m, 2H), 2.85-2.76 (m, 2H), 2.45 (m, J=7.9 Hz, 2H), 2.36 (s, 3H), 2.20-2.11 (m, 2H), 2.05-2.00 (m, 1H), 1.79-1.73 (m, 1H), 1.67 (s, 3H). MS m/z: 539.5 [M+H]$^+$.

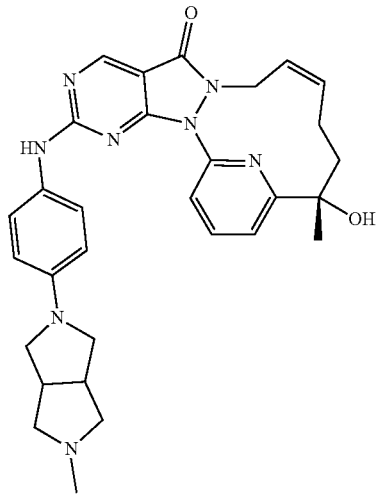

25

Example 25: Compound 26

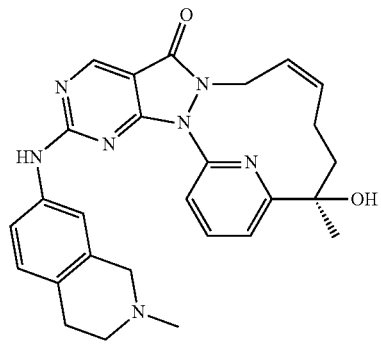 [SMILES: CN1CCc2ccc(Nc3ncc4c(=O)n5n(c4n3)-c3cccc(n3)[C@](C)(O)CC/C=C\C5)cc2C1]

Synthetic Route

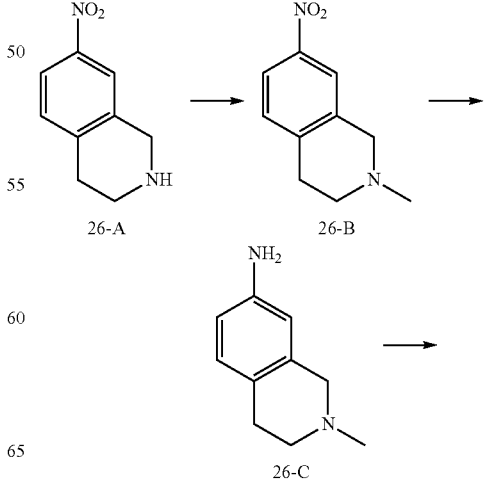

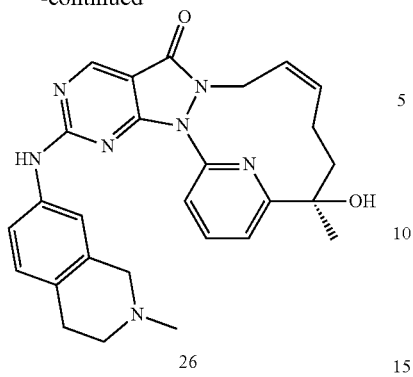

26

Step 1: Synthesis of Compound 26-B

Except that the corresponding raw materials were used, a crude product of 26-B was obtained in the same method as the synthesis of compound 10-C in Example 8. $^1$H NMR (400 MHz, CDCl$_3$) δ ppm 7.92 (dd, J=8.4, 2.4 Hz, 1H) 7.85 (d, J=2.6 Hz, 1H) 7.19 (s, 1H) 3.58 (s, 2H) 2.94 (t, J=5.6 Hz, 2H) 2.66 (t, J=6.0 Hz, 2H) 2.40-2.45 (m, 3H). MS m/z: 193.0 [M+H]$^+$.

Step 2: Synthesis of Compound 26-C

Except that the corresponding raw materials were used, 26-C was obtained in the same method as the synthesis of compound 10-D in Example 8. MS m/z: 163.3 [M+H]$^+$.

Step 3: Synthesis of Compound 26

To a solution of compound 12-A (100 mg, 270.68 μmol) in toluene (7 mL) and dichloromethane (1 mL) was added m-chloroperoxybenzoic acid (70.07 mg, 324.82 μmol, 80% purity). The reaction solution was stirred at 20° C. for 1 hour. N, N-diisopropylethylamine (104.95 mg, 812.04 μmol) and 26-B (52.70 mg, 324.82 μmol) were added to the reaction solution, and the reaction solution was stirred at 20° C. for 12 hours. Water (10 mL) was added to the reaction solution, the aqueous phase was extracted with ethyl acetate (15 mL×3), the organic phases were combined and washed with saturated sodium bicarbonate solution (20 mL), partitioned, and the organic phase was washed with saturated brine (20 mL) and partitioned. The organic phase was dried over anhydrous sodium sulfate, filtered, and the solvent was removed by rotary evaporation to obtain a crude product. The crude product was separated by preparative liquid chromatography to obtain 26. $^1$H NMR (400 MHz, CDCl$_3$) δ ppm 8.79 (s, 1H), 7.73-7.83 (m, 2H), 7.45 (s, 1H), 7.34 (s, 1H), 7.21 (s, 1H), 7.02 (d, J=8.0 Hz, 1H), 5.67 (br s, 2H), 4.41-4.44 (d, J=12.8 Hz, 1H), 4.16 (s, 1H), 3.50-3.51 (m, 2H), 2.82-2.87 (m, 2H), 2.53-2.72 (m, 2H), 2.42 (s, 3H), 2.00-2.16 (m, 2H), 1.88-1.98 (m, 1H), 1.69-1.72 (m, 1H), 1.61 (s, 3H); MS m/z: 484.3 [M+H]$^+$.

Example 26: Compound 27

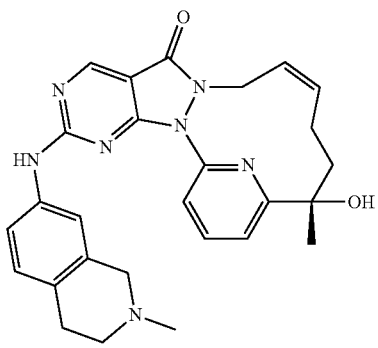 [SMILES: CN1CCc2ccc(Nc3ncc4c(=O)n5n(c4n3)-c3cccc(n3)[C@@](C)(O)CC/C=C\C5)cc2C1]

27

Synthetic Route

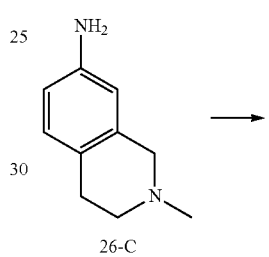

26-C

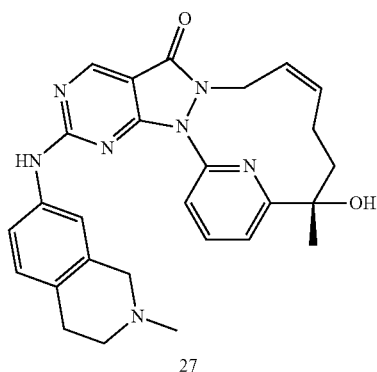

27

Step 1: Synthesis of Compound 27

Except that the corresponding raw materials were used, 27 was obtained in the same method as the synthesis of compound 26 in Example 25. $^1$H NMR (400 MHz, CDCl$_3$) δ ppm 8.88 (s, 1H), 7.82-7.92 (m, 2H), 7.54 (s, 1H), 7.43 (s, 1H), 7.30 (s, 1H), 7.10 (d, J=8.2 Hz, 1H), 5.77 (br s, 2H), 4.49-4.53 (d, J=13.6 Hz, 1H), 4.26 (s, 1H), 3.53-3.66 (m, 2H), 2.91-2.94 (m, 2H), 2.72-2.74 (m, 2H), 2.50 (s, 3H), 2.15-2.21 (m, 2H), 1.99-2.04 (m, 1H), 1.79-1.81 (m, 1H), 1.70 (s, 3H). MS m/z: 484.3 [M+H]$^+$.

Example 27: Compound 28

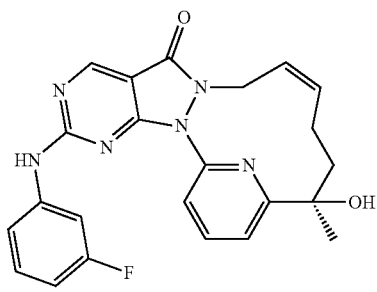 [SMILES: C[C@@]1(O)CC/C=C\Cn2c(=O)c3cnc(Nc4cccc(F)c4)nc3n2-c2cccc1n2]

Synthetic Route

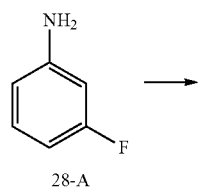

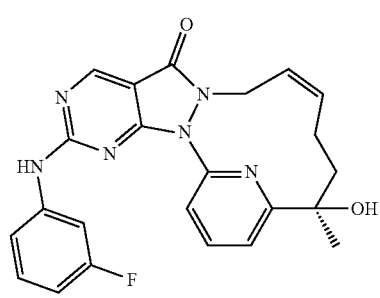

Step 1: Synthesis of Compound 28

Except that the corresponding raw materials were used, 28 was obtained in the same method as the synthesis of compound 26 in Example 25. $^1$H NMR (400 MHz, CDCl$_3$) δ ppm 8.84 (m, 1H), 7.83-7.90 (m, 1H), 7.72-7.79 (m, 2H), 7.20-7.25 (m, 2H), 7.03 (d, J=7.6 Hz, 1H), 6.74 (t, J=8.2 Hz 1H), 5.67 (br s, 2H), 4.46 (d, J=13.2 Hz, 1H), 4.15 (s, 1H), 1.98-2.17 (m, 2H), 1.85-1.97 (m, 1H), 1.70 (d, J=14.4 Hz, 1H), 1.62 (s, 3H); MS m/z: 433.0 [M+H]$^+$.

Example 28: Compound 29

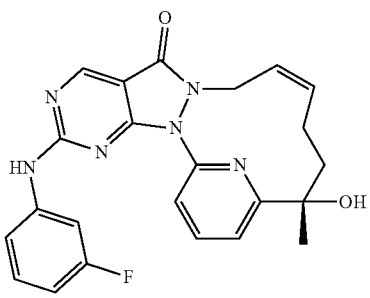

Synthetic Route

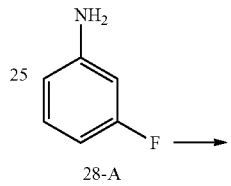

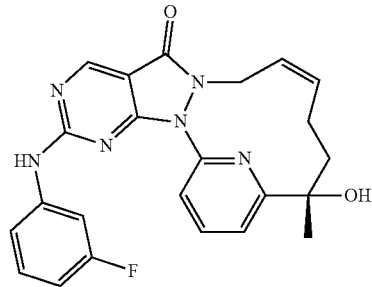 [SMILES: C[C@]1(O)CC/C=C\Cn2c(=O)c3cnc(Nc4cccc(F)c4)nc3n2-c2cccc1n2]

Step 1: Synthesis of Compound 29

Except that the corresponding raw materials were used, 29 was obtained in the same method as the synthesis of compound 26 in Example 25. $^1$H NMR (400 MHz, CDCl$_3$) δ ppm 8.83 (s, 1H), 7.82-7.90 (m, 1H), 7.67-7.79 (m, 2H), 7.22-7.24 (m, 2H), 7.03 (d, J=7.6 Hz, 1H), 6.73 (t, J=7.2 Hz, 1H), 5.67 (br s, 2H), 4.46 (d, J=10.8 Hz, 1H), 4.15 (s, 1H), 2.00-2.17 (m, 2H), 1.85-1.97 (m, 1H), 1.70 (d, J=14.4 Hz, 1H), 1.62 (s, 3H); MS m/z: 433.0 [M+H]$^+$.

Example 29: Compound 30

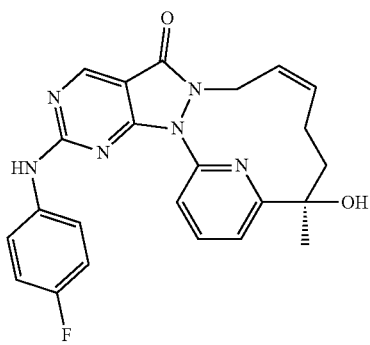

Synthetic Route

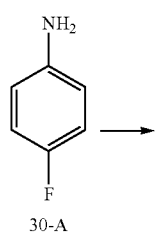

30-A

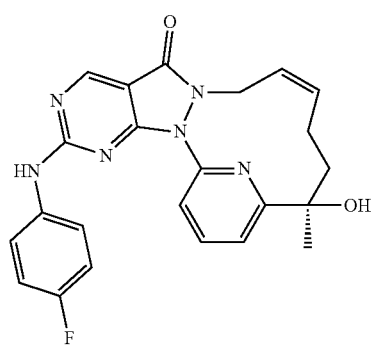 [SMILES: C[C@@]1(O)CC/C=C\Cn2c(=O)c3cnc(Nc4ccc(F)cc4)nc3n2-c2cccc1n2]

30

Step 1: Synthesis of Compound 30

Except that the corresponding raw materials were used, 30 was obtained in the same method as the synthesis of compound 26 in Example 25. $^1$H NMR (400 MHz, CDCl$_3$) δ ppm 8.80 (s, 1H), 7.76-7.82 (m, 1H), 7.65-7.70 (d, J=8.0 Hz, 1H), 7.45-7.51 (m, 2H), 7.18-7.22 (d, 1H), 6.93-7.01 (t, J=8.4 Hz, 2H), 5.64 (br s, 2H), 4.38-4.46 (m, 1H), 2.01-2.17 (m, 2H), 4.18 (s, 1H), 1.86-1.98 (m, 1H), 1.65-1.74 (m, 1H), 1.61 (m, 3H). MS m/z: 433.0 [M+H]$^+$.

Example 30: Compound 31

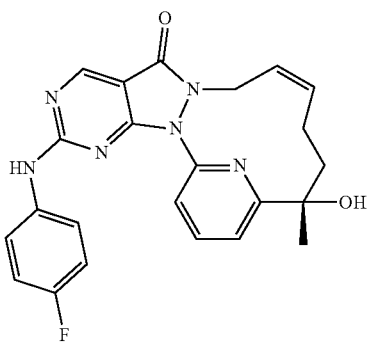

Synthetic Route

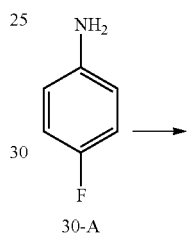

30-A

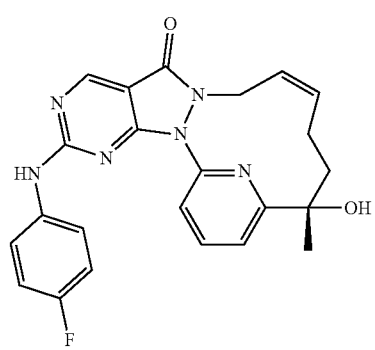 [SMILES: C[C@]1(O)CC/C=C\Cn2c(=O)c3cnc(Nc4ccc(F)cc4)nc3n2-c2cccc1n2]

31

Step 1: Synthesis of Compound 31

Except that the corresponding raw materials were used, 31 was obtained in the same method as the synthesis of compound 26 in Example 25. $^1$H NMR (400 MHz, CDCl$_3$) δ ppm 8.80 (s, 1H), 7.75-7.84 (m, 1H), 7.65-7.71 (d, J=8.0 Hz, 1H), 7.44-7.53 (m, 2H), 7.20-7.22 (d, 1H), 6.94-7.01 (t, J=8.8 Hz, 2H), 5.64 (br s, 2H), 4.38-4.48 (m, 1H), 4.17 (s, 1H), 2.00-2.18 (m, 2H), 1.88-1.95 (m, 1H), 1.65-1.74 (m, 1H), 1.61 (s, 3H). MS m/z: 433.0 [M+H]$^+$.

Example 31: Compound 32

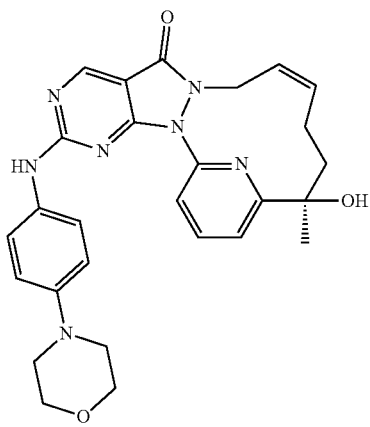 [SMILES: C[C@@]1(O)CC/C=C\Cn2c(=O)c3cnc(Nc4ccc(N5CCOCC5)cc4)nc3n2-c2cccc1n2]

Synthetic Route

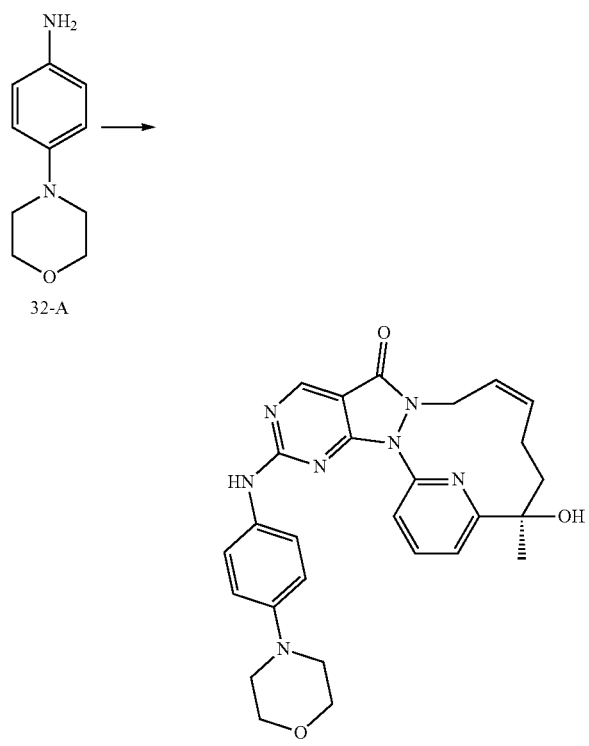

Step 1: Synthesis of Compound 32

Except that the corresponding raw materials were used, 32 was obtained in the same method as the synthesis of compound 26 in Example 25. $^1$H NMR (400 MHz, CDCl$_3$) δ ppm 8.77 (s, 1H), 7.69-7.82 (m, 2H), 7.36-7.45 (d, J=8.8 Hz, 2H), 7.16-7.20 (d, 1H), 6.80-6.86 (d, J=8.78 Hz, 2H), 5.64 (br s, 2H), 4.39-4.44 (d, J=10.28 Hz, 1H), 4.20 (s, 1H), 3.75-3.87 (m, 4H), 3.01-3.15 (m, 4H), 1.99-2.18 (m, 2H), 1.88-1.99 (m, 1H), 1.65-1.71 (m, 1H), 1.61 (m, 3H); MS m/z: 500.3 [M+H]$^+$.

Example 32: Compound 33

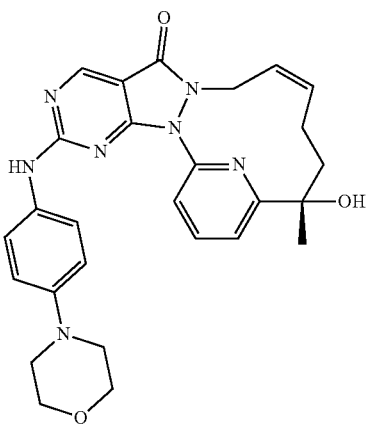 [SMILES: C[C@]1(O)CC/C=C\Cn2c(=O)c3cnc(Nc4ccc(N5CCOCC5)cc4)nc3n2-c2cccc1n2]

Synthetic Route

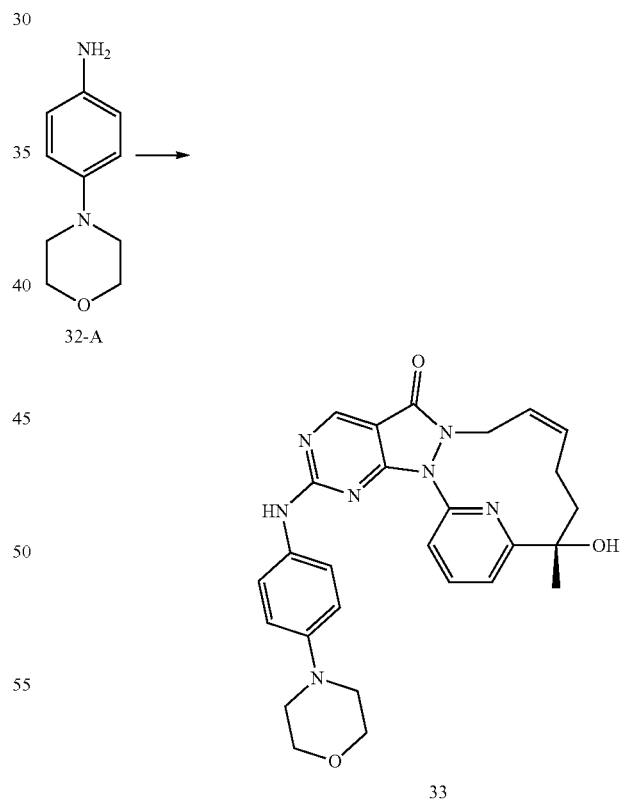

Step 1: Synthesis of Compound 33 222

Except that the corresponding raw materials were used, 33 was obtained in the same method as the synthesis of compound 26 in Example 25.

¹H NMR (400 MHz, CDCl₃) δ ppm 8.84 (s, 1H) 7.77-7.89 (m, 2H) 7.46-7.51 (d, J=9.2 Hz, 2H), 7.26 (s, 1H), 6.86-6.92 (d, J=8.8 Hz, 2H), 5.71 (br s, 2H), 4.44-4.49 (d, J=13.0 Hz, 1H), 4.25 (s, 1H), 3.81-3.94 (m, 4H), 3.08-3.21 (m, 4H), 2.09-2.24 (m, 2H), 1.94-2.04 (m, 1H), 1.74-1.79 (m, 1H), 1.67 (s, 3H); MS m/z: 500.0 [M+H]⁺.

Example 33: Compound 34

Synthetic Route

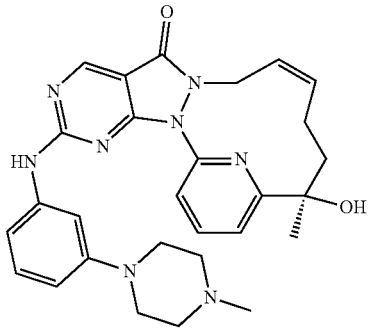 [SMILES: CN1CCN(c2cccc(Nc3ncc4c(=O)n5n(c4n3)-c3cccc(n3)[C@](C)(O)CC/C=C\C5)c2)CC1]

.34-A

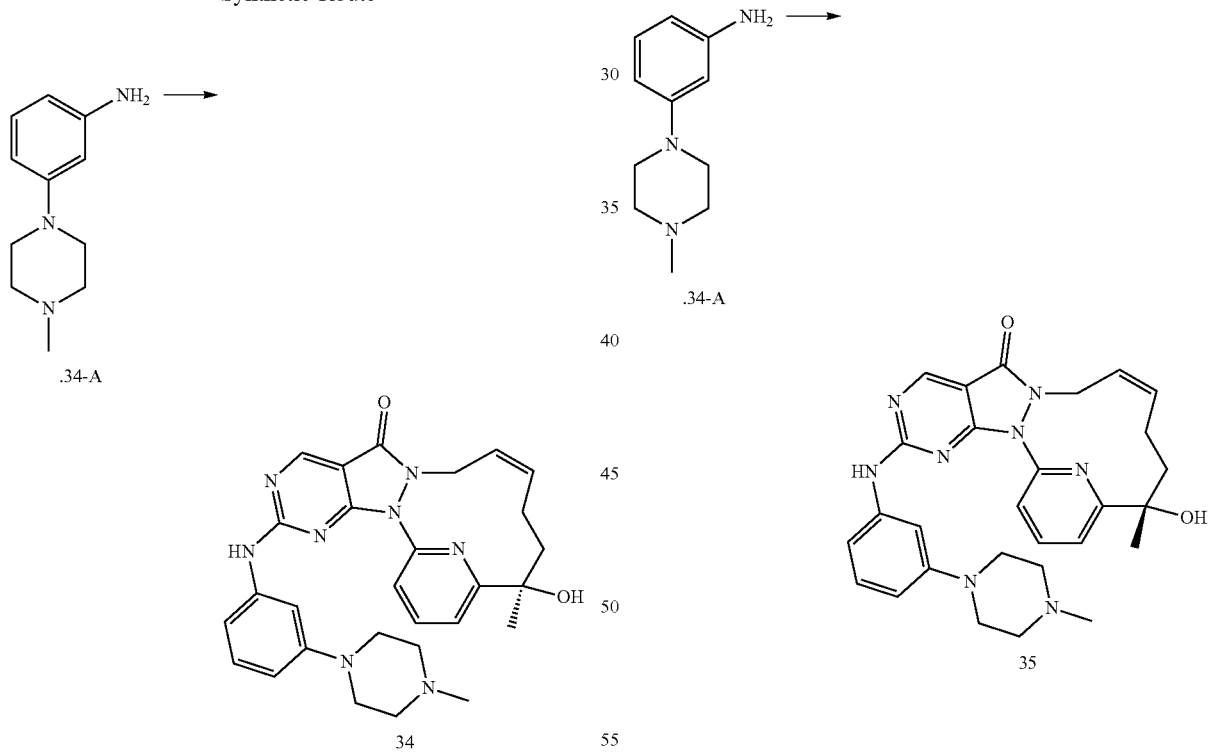

34

Step 1: Synthesis of Compound 34

Except that the corresponding raw materials were used, 34 was obtained in the same method as the synthesis of compound 26 in Example 25. ¹H NMR (400 MHz, CDCl₃) δ ppm 8.79 (s, 1H), 7.73-7.87 (m, 2H), 7.69 (br s, 1H), 7.10-7.19 (m, 2H), 6.90-6.97 (d, J=7.2 Hz, 1H), 6.56-6.63 (d, J=7.6 Hz, 1H), 5.55 (br s, 2H), 4.45 (br s, 1H), 4.32 (br s, 1H), 3.07 (br s, 4H), 2.44 (br s, 4H), 2.27 (s, 3H), 2.02-2.13 (m, 2H), 1.85-1.95 (d, J=8.2 Hz, 1H), 1.65-1.72 (d, J=6.2 Hz, 1H), 1.62 (s, 3H); MS m/z: 513.3 [M+H]⁺.

Example 34: Compound 35

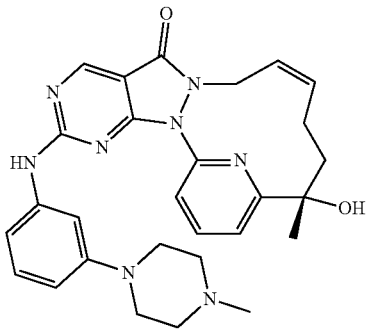 [SMILES: CN1CCN(c2cccc(Nc3ncc4c(=O)n5n(c4n3)-c3cccc(n3)[C@@](C)(O)CC/C=C\C5)c2)CC1]

Synthetic Route

.34-A

35

Step 1: Synthesis of Compound 35

Except that the corresponding raw materials were used, 35 was obtained in the same method as the synthesis of compound 26 in Example 25. ¹H NMR (400 MHz, CDCl₃) δ ppm 8.79 (s, 1H), 7.73-7.95 (m, 2H), 7.69 (br s, 1H), 7.09-7.19 (m, 2H), 6.89-6.95 (d, J=7.0 Hz, 1H), 6.52-6.63 (d, J=7.6 Hz, 1H), 5.54 (br s, 2H), 4.45 (br s, 1H), 4.33 (br s, 1H), 3.07 (br s, 4H), 2.44 (br s, 4H), 2.27 (s, 3H), 2.04-2.12 (m, 2H), 1.85-1.95 (d, J=8.4 Hz, 1H), 1.64-1.72 (d, J=7.2 Hz, 1H), 1.62 (s, 3H); MS m/z: 513.3 [M+H]⁺.

Example 35: Compound 36

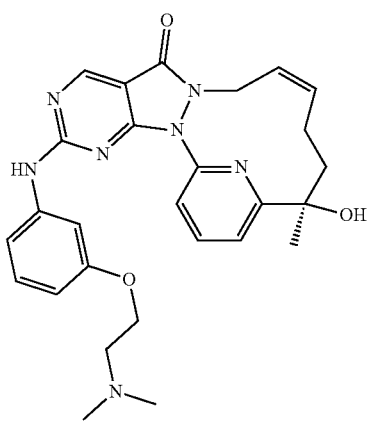 [SMILES: CN(C)CCOc1cccc(Nc2ncc3c(=O)n4n(c3n2)-c2cccc(n2)[C@](C)(O)CC/C=C\C4)c1]

Synthetic Route

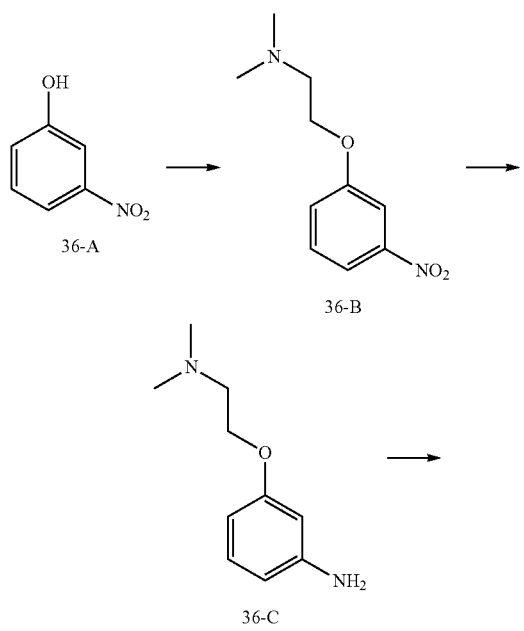

Step 1: Synthesis of Compound 36-B

To a solution of compound 36-A (1.5 g, 10.78 mmol) in N,N-dimethylformamide (25 mL) was added potassium carbonate (4.47 g, 32.35 mmol) and 2-chloroethyldimethylamine hydrochloride (2.33 g, 16.17 mmol). The reaction solution was stirred at 85° C. for 2 hours. Water (10 mL) was added to the reaction solution, and the aqueous phase was extracted with ethyl acetate (15 mL*3). The organic phases were combined and washed with saturated brine (15 mL), dried over anhydrous sodium sulfate, filtered, and the filtrate was dried by rotary evaporation to obtain a crude product. The crude product was separated by column chromatography (dichloromethane/methanol=10/1) to obtain 36-B. MS m/z: 211.3 [M+H]$^+$.

Step 2: Synthesis of Compound 36-C

To a solution of compound 36-B (717 mg, 3.41 mmol) in ethanol (20 mL) was added wet palladium on carbon (300 mg, 253.31 μmol), and the reaction solution was stirred at 25° C. for 12 hours under hydrogen atmosphere (15 Psi). The reaction solution was filtered and the filtrate was dried by rotary evaporation to obtain 36-C.

$^1$H NMR (400 MHz, CDCl$_3$) δ ppm 7.07 (t, J=7.9 Hz, 1H), 6.26-6.38 (m, 3H), 4.05 (t, J=5.8 Hz, 2H), 2.72 (t, J=5.8 Hz, 2H), 2.29-2.41 (m, 6H); MS m/z: 181.2 [M+H]$^+$.

Step 3: Synthesis of Compound 36

Except that the corresponding raw materials were used, 36 was obtained in the same method as the synthesis of compound 26 in Example 25. $^1$H NMR (400 MHz, CDCl$_3$) δ ppm 8.81 (s, 1H), 7.82-7.88 (m, 1H), 7.70-7.81 (m, 1H), 7.60 (s, 1H), 7.34 (s, 1H), 7.12-7.19 (m, 1H), 6.98-7.02 (d, J=7.4 Hz, 1H), 6.58-6.62 (d, J=8.2 Hz, 1H), 5.64 (br s, 2H), 4.40-4.52 (d, J=10.2 Hz, 1H), 4.21 (br s, 1H), 3.93-4.01 (t, J=5.4 Hz, 2H), 2.61-2.68 (t, J=5.4 Hz, 2H), 2.27 (s, 6H), 2.04-2.14 (m, 2H), 1.88-1.94 (d, J=11.0 Hz, 1H), 1.65-1.70 (m, 1H), 1.61 (s, 3H); MS m/z: 502.2 [M+H]$^+$.

Example 36: Compound 37

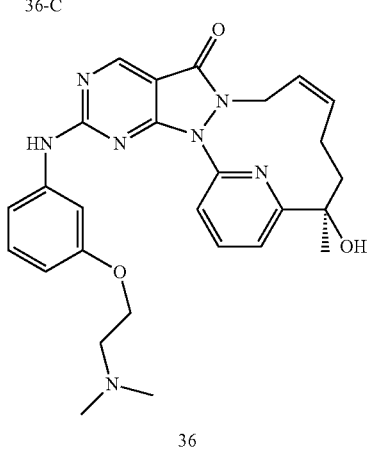

36

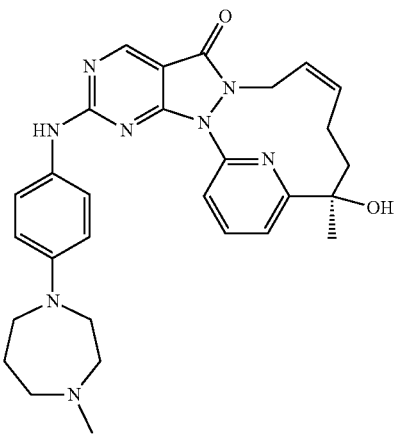 [SMILES: CN1CCCN(c2ccc(Nc3ncc4c(=O)n5n(c4n3)-c3cccc(n3)[C@](C)(O)CC/C=C\C5)cc2)CC1]

Synthetic Route

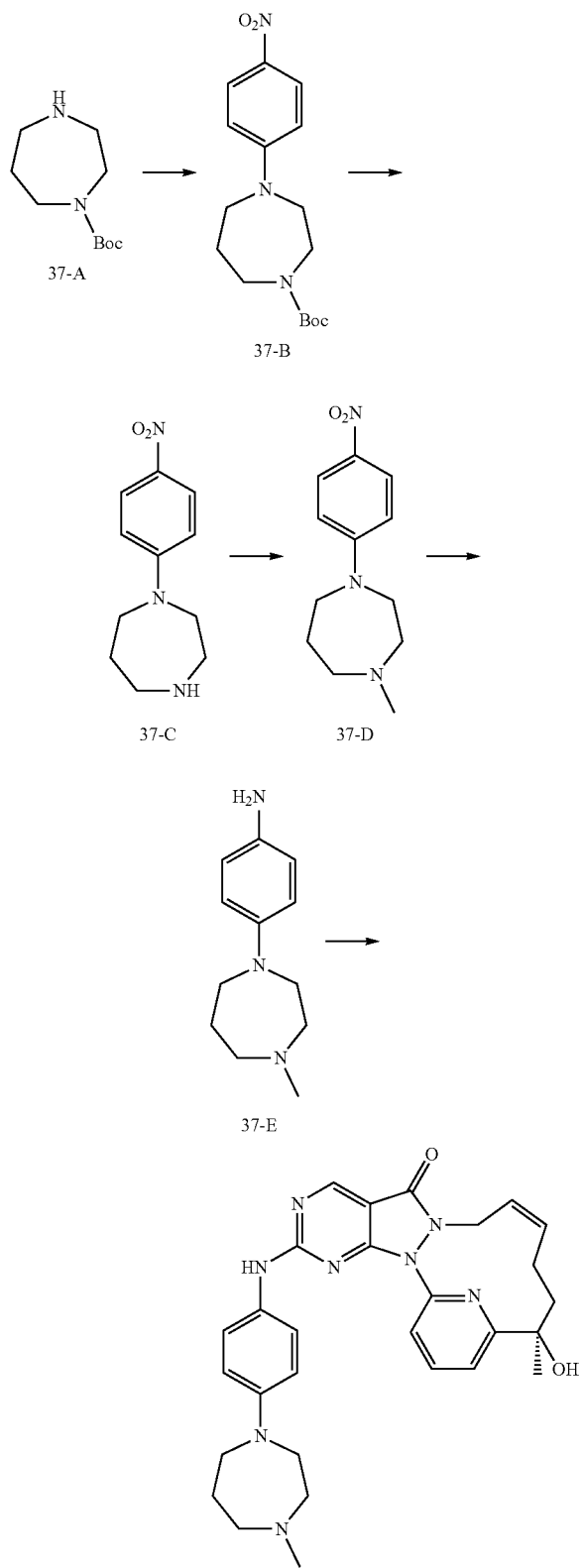

37

Step 1: Synthesis of Compound 37-B

To a solution of 4-fluoronitrobenzene (2.52 g, 14.98 mmol) in dimethyl sulfoxide (40 mL) was added potassium carbonate (3.00 g, 21.72 mmol) and 37-A (3 g, 14.98 mmol), the reaction solution was stirred at 100° C. for 12 hours. 120 mL of water was added to the reaction solution and stirred, the suspension was filtered, and the filter cake was washed once with 20 mL of water to obtain 37-B. $^1$H NMR (400 MHz, CDCl$_3$) δ ppm 8.14 (d, J=9.2 Hz, 2H), 6.68 (d, J=9.2 Hz, 2H), 3.61-3.73 (m, 6H), 3.24-3.42 (m, 2H), 2.00 (d, J=5.8 Hz, 2H), 1.36-1.46 (m, 9H).

Step 2: Synthesis of Compound 37-C

To a solution of 37-B (3 g, 9.34 mmol) in dichloromethane (18 mL) was added trifluoroacetic acid (9.24 g, 81.04 mmol), and the reaction was stirred at 30° C. for 1 hour. The reaction solution was concentrated to dryness, 20 mL of water was added to the crude product, the aqueous phase was extracted with dichloromethane (30 mL), and the organic phase was discarded. The pH of the aqueous phase was adjusted to 11-12 with 10% aqueous sodium hydroxide solution, the aqueous phase was extracted with dichloromethane (40 mL×3), the organic phases were combined and was washed with saturated brine (40 mL), dried over anhydrous sodium sulfate, and filtered. The filtrate was dried by rotary evaporation to obtain 37-C. MS m/z: 222.0 [M+H]$^+$.

Step 3: Synthesis of Compound 37-D

To a solution of 37-C (1.87 g, 8.45 mmol) in methanol (18 mL) was added formaldehyde (6.72 g, 82.83 mmol), sodium borohydride acetate (3.58 g, 16.90 mmol) and acetic acid (507.54 mg, 8.45 mmol), the reaction solution was stirred at 30° C. for 1 hour. The pH of the reaction solution was adjusted to 5 by the addition of 2 mol/L dilute hydrochloric acid, then the organic phase was distilled off, the pH of the aqueous phase was adjusted to 11 with 10% aqueous sodium hydroxide solution, the aqueous phase was extracted with dichloromethane (50 mL×3), the organic phases were combined and washed with saturated brine (30 mL), dried over anhydrous sodium sulfate, filtered, and the filtrate was dried by rotary evaporation to obtain 37-D. $^1$H NMR (400 MHz, CDCl$_3$) δ ppm 8.03 (d, J=9.6 Hz, 2H), 6.56 (d, J=9.6 Hz, 2H), 3.57-3.61 (m, 2H), 3.52 (t, J=6.2 Hz, 2H), 2.63-2.68 (m, 2H), 2.46-2.53 (m, 2H), 2.29-2.36 (m, 3H), 1.96 (d, J=5.8 Hz, 2H); MS m/z: 235.9 [M+H]$^+$.

Step 4: Synthesis of Compound 37-E

To a solution of 37-D (1.5 g, 6.38 mmol) in tetrahydrofuran (20 mL) was added palladium on carbon (760 mg, 644.07 μmol), and the reaction solution was stirred at 30° C. for 12 hours under hydrogen atmosphere (15 PSI). The reaction solution was filtered and the filtrate was dried by rotary evaporation to obtain 37-E. $^1$H NMR (400 MHz, CDCl$_3$) δ ppm 6.55-6.61 (m, 2H), 6.48-6.53 (m, 2H), 3.38-3.46 (m, 2H), 3.34 (t, J=6.6 Hz, 2H), 2.58-2.64 (m, 2H), 2.45-2.54 (m, 2H), 2.27-2.37 (m, 3H), 1.91 (d, J=11.4, 2H); MS m/z: 206.1 [M+H]$^+$.

Step 5: Synthesis of Compound 37

To a solution of 12-A (200 mg, 541.36 μmol) in toluene (10 mL) was added m-chloroperoxybenzoic acid (140.13 mg, 649.63 µmol), and the reaction solution was stirred at 15° C. for 4 hours, 37-E (133.37 mg, 649.63 µmol) and N,N-diisopropylethylamine (209.90 mg, 1.62 mmol) were added to the reaction solution, and the reaction solution was stirred at 15° C. for 12 hours. 15 mL of water was added to the reaction solution, the aqueous phase was extracted with ethyl acetate (15 mL*3), the organic phases were combined and washed with sodium sulfite (20 mL), and then further washed with sodium bicarbonate (20 mL) and saturated brine (20 mL), dried over anhydrous sodium sulfate, filtered, and the filtrate was dried by rotary evaporation to obtain a crude product. The crude product was separated by column chromatography (dichloromethane/methanol=10/1, 0.5% NH$_3$.H$_2$O) and preparative liquid (neutral) chromatography to obtain 37. $^1$H NMR (400 MHz, CDCl$_3$) δ ppm 8.75 (s, 1H), 7.72-7.79 (m, 2H), 7.31 (d, J=8.0 Hz, 2H), 7.17 (d, J=7.6 Hz, 1H), 6.60 (d, J=8.8 Hz, 2H), 5.65 (s, 2H), 4.41 (d, J=9.4 Hz, 1H), 4.18 (s, 1H), 3.48-3.54 (m, 2H), 3.43 (t, J=6.2 Hz, 2H), 2.62-2.69 (m, 2H), 2.49-2.55 (m, 2H), 2.32 (s, 3H), 2.01-2.15 (m, 2H), 1.94-1.98 (m, 2H), 1.69 (d, J=13.8 Hz, 2H), 1.60 (s, 3H); MS m/z: 527.1 [M+H]$^+$.

Example 37: Compound 38

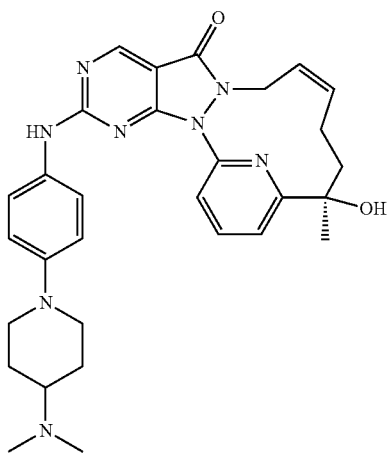 [SMILES: CN(C)C1CCN(c2ccc(Nc3ncc4c(=O)n5n(c4n3)-c3cccc(n3)[C@](C)(O)CC/C=C\C5)cc2)CC1]

Synthetic Route

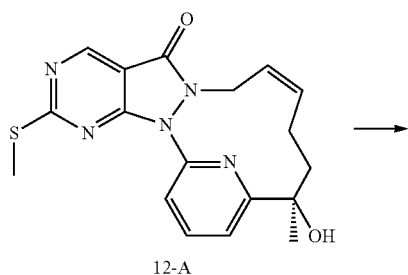

12-A

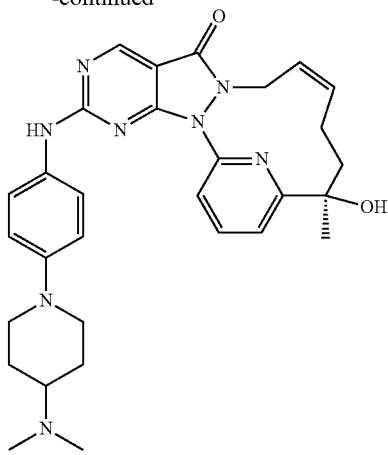

38

Step 1: Synthesis of Compound 38

Except that the corresponding raw materials were used, 38 was obtained in the same method as the synthesis of compound 37 in Example 36. $^1$H NMR (400 MHz, CDCl$_3$) δ ppm 8.78 (s, 1H), 7.71-7.82 (m, 2H), 7.39 (d, J=8.8 Hz, 2H), 7.18 (s, 1H), 6.86 (d, J=8.8 Hz, 2H), 5.65 (s, 2H), 4.42 (d, J=12.4 Hz, 1H), 4.18 (s, 1H), 3.63 (d, J=11.6 Hz, 2H), 2.65 (t, J=12.4 Hz, 2H), 2.28 (s, 6H), 2.04-2.17 (m, 2H), 1.89 (d, J=12.4 Hz, 3H), 1.68-1.83 (m, 4H), 1.61 (s, 3H); MS m/z: 541.1 [M+H]$^+$.

Example 38: Compound 39

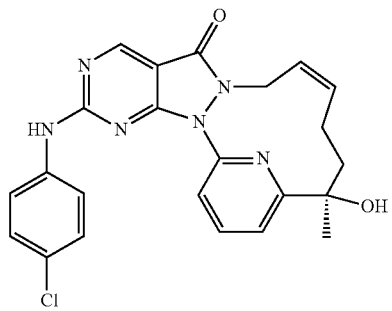 [SMILES: C[C@@]1(O)CC/C=C\Cn2c(=O)c3cnc(Nc4ccc(Cl)cc4)nc3n2-c2cccc1n2]

Synthetic Route

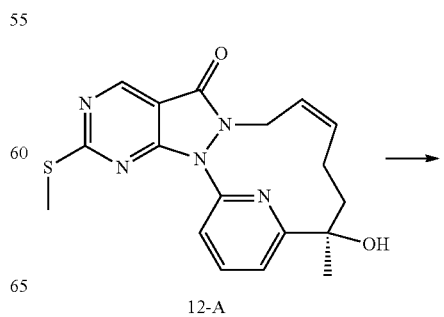

12-A

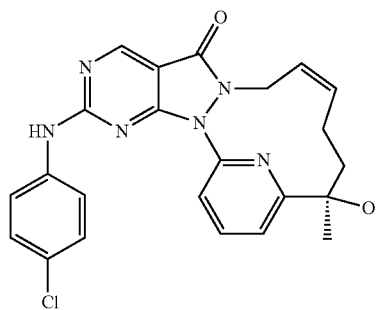

39

Step 1: Synthesis of Compound 39

To a solution of 12-A (100 mg, 270.68 μmol) in toluene (7 mL) was added m-chloroperoxybenzoic acid (70.07 mg, 324.82 μmol), the reaction solution was stirred at 25° C. for 1 hour, 4-chloroaniline (37.98 mg, 297.75 μmol) and N,N-diisopropylethylamine (139.93 mg, 1.08 mmol) were added to the reaction solution, and the reaction solution was stirred at 25° C. for 12 hours. 10 mL of water was added to the reaction solution, the aqueous phase was extracted with ethyl acetate (15 mL×3), the organic phases were combined, then washed with sodium bicarbonate (20 mL) and saturated brine (20 mL), and dried over sodium sulfate and filtered, the filtrate was dried by rotary evaporation to obtain a crude product. The crude product was separated by preparative liquid (neutral) chromatography to obtain 39. $^1$H NMR (400 MHz, CDCl$_3$) δ ppm 8.82 (s, 1H), 7.80-7.85 (m, 1H), 7.69 (d, J=7.8 Hz, 1H), 7.60 (s, 1H), 7.47-7.52 (m, 2H), 7.22-7.25 (m, 2H), 5.64 (s, 2H), 4.45 (d, J=13.2 Hz, 1H), 4.18 (br s, 1H), 2.05-2.14 (m, 1H), 1.85-1.96 (m, 1H), 1.69 (d, J=17.6 Hz, 2H), 1.62 (s, 3H); MS m/z: 449.0 [M+H]$^+$.

Example 39: Compound 40

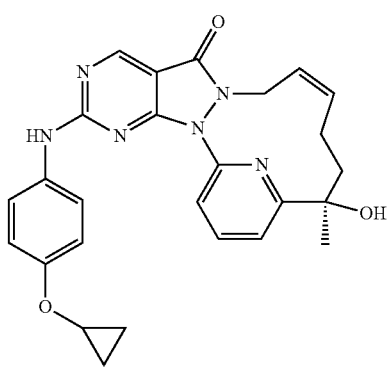 [SMILES: C[C@@]1(O)CC/C=C\Cn2c(=O)c3cnc(Nc4ccc(OC5CC5)cc4)nc3n2-c2cccc1n2]

Synthetic Route

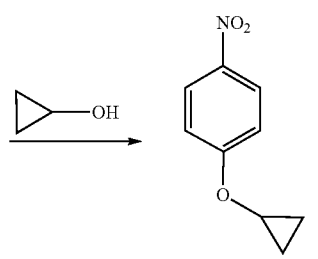

40-A

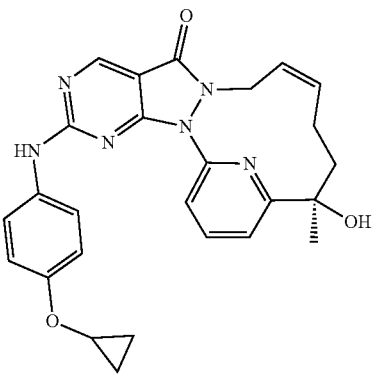

40

Step 1: Synthesis of Compound 40-A

To a solution of sodium hydride in DMF (20 mL) was added potassium iodide (142.91 mg, 860.89 μmol), the reaction solution was stirred at 5-10° C. under nitrogen protection, and a solution of cyclopropanol (500 mg, 8.61 mmol) in DMF (0.5 mL) was slowly added to the reaction solution and stirred at 5-10° C. for 1 hour. Then a solution of p-fluoronitrobenzene (1.34 g, 9.47 mmol) in DMF (0.5 mL) was added to the reaction solution, and the reaction solution was stirred at 25° C. for 12 hours. Saturated ammonium chloride solution (15 mL) was added to the reaction solution, the aqueous phase was extracted with ethyl acetate (20 mL×3), the organic phases were combined and washed once with saturated brine (20 mL) and dried over anhydrous sodium sulfate, filtered, and the filtrate was dried by rotary evaporation to obtain a crude product, which was separated by column chromatography (petroleum ether/ethyl acetate=1-10/1) to obtain 40-A.

$^1$H NMR (400 MHz, CDCl$_3$) δ=8.10-8.16 (m, 2H), 7.05 (d, J=8.06 Hz, 2H), 3.74-3.79 (m, 1H), 0.72-0.84 (m, 4H).

107

Step 2: Synthesis of Compound 40-B

Except that the corresponding raw materials were used, 40-B was obtained in the same method as the synthesis of compound 18-B in Example 17.

$^1$H NMR (400 MHz, CDCl$_3$) δ=6.87-6.93 (m, 2H), 6.64-6.70 (m, 2H), 3.65-3.71 (m, 1H), 0.71-0.80 (m, 4H). MS m/z: 150.0 [M+H]$^+$.

Step 3: Synthesis of Compound 40

Except that the corresponding raw materials were used, 40 was obtained in the same method as the synthesis of compound 22 in Example 21.

$^1$H NMR (400 MHz, CDCl$_3$) δ=8.86 (s, 1H), 7.89-7.83 (t, 1H), 7.82-7.77 (d, 1H), 7.49 (d, J=9.0 Hz, 2H), 7.42 (br s, 1H), 7.25 (d, 1H), 7.05 (d, J=8.8 Hz, 2H), 5.75 (br s, 2H), 4.50 (m, J=12.3 Hz, 1H), 4.33 (br s, 1H), 4.25-4.20 (s, 1H), 3.78-3.73 (m, 1H), 2.22-2.08 (m, 2H), 2.01 (m, J=10.5 Hz, 1H), 1.77 (m, J=13.8 Hz, 1H), 1.68 (s, 3H), 0.82-0.78 (m, 4H). MS m/z: 471.3 [M+H]$^+$.

Example 40: Compound 41

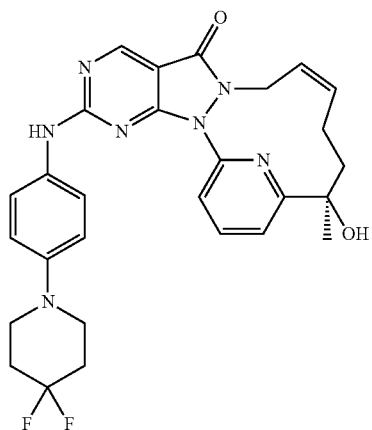 [SMILES: C[C@@]1(O)CC/C=C\Cn2c(=O)c3cnc(Nc4ccc(N5CCC(F)(F)CC5)cc4)nc3n2-c2cccc1n2]

Synthetic Route

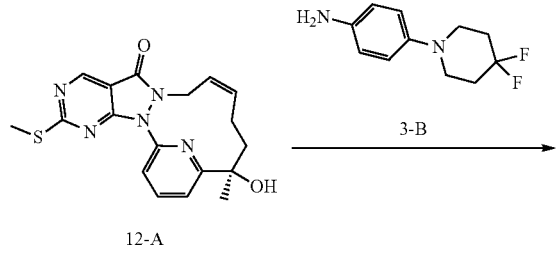

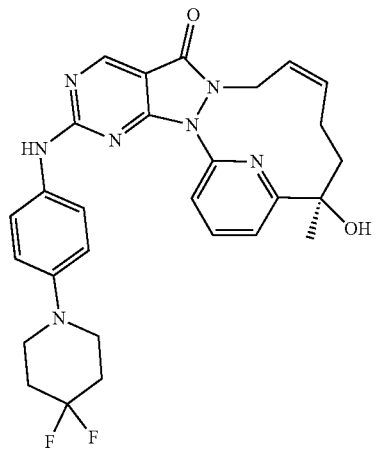

41

Step 1: Synthesis of Compound 41

Except that the corresponding raw materials were used, 40 was obtained in the same method as the synthesis of compound 22 in Example 21.

$^1$H NMR (400 MHz, CDCl$_3$) δ=8.85 (s, 1H), 7.90-7.83 (t, 1H), 7.82-7.76 (d, 1H), 7.49 (d, J=8.8 Hz, 2H), 7.29-7.24 (d, 1H), 6.94 (d, J=8.8 Hz, 2H), 5.72 (br s, 2H), 4.50 (m, J=12.5 Hz, 1H), 4.42-4.29 (br s, 1H), 4.29-4.21 (s, 1H), 3.40-3.26 (m, 4H), 2.20-2.05 (m, 6H), 2.05-1.95 (m, 1H), 1.79-1.74 (m, 1H), 1.68 (s, 3H). MS m/z: 534.1 [M+H]$^+$.

Example 41: Compound 42

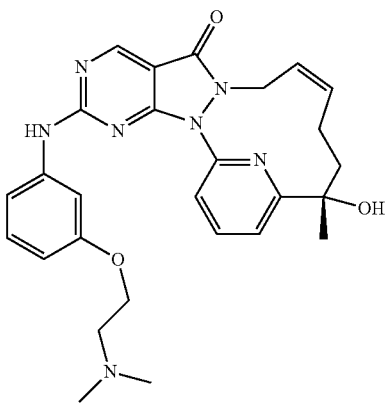 [SMILES: CN(C)CCOc1cccc(Nc2ncc3c(=O)n4n(c3n2)-c2cccc(n2)[C@@](C)(O)CC/C=C\C4)c1]

Synthetic Route

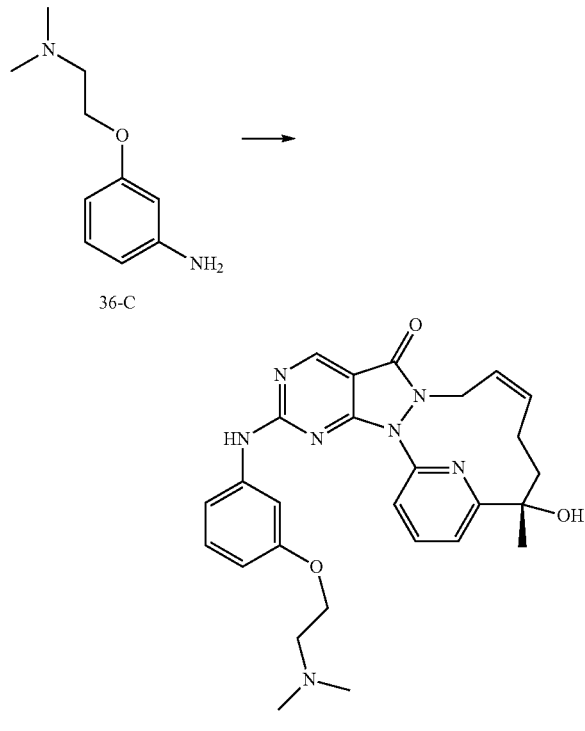

Step 1: Synthesis of Compound 37

Except that the corresponding raw materials were used, 37 was obtained in the same method as the synthesis of compound 26 in Example 25. $^1$H NMR (400 MHz, CDCl$_3$) δ ppm 8.82 (s, 1H) 7.82-7.88 (m, 1H) 7.70-7.81 (m, 1H) 7.58 (br s, 1H) 7.35 (s, 1H) 7.12-7.20 (d, J=8.2 Hz, 1H) 6.58-6.62 (d, J=8.2, 1H) 5.64 (br s, 2H) 4.42-4.51 (d, J=12.0 Hz, 1H) 4.19 (br s, 1H) 3.94-4.01 (t, J=5.6 Hz, 2H) 2.62-2.68 (t, J=5.4 Hz, 2H) 2.27 (s, 6H) 2.03-2.14 (m, 2H) 1.86-1.96 (d, J=11.2 Hz, 1H) 1.69-1.73 (m, 1H) 1.61 (s, 3H); MS m/z: 502.2 [M+H]$^+$.

Experimental Example 1: In Vitro Enzymatic Inhibitory Activity of the Compounds of the Present Invention The experimental tests were conducted at Eurofins, and the results were provided by the company.

In the test system, 20 mM Tris-HCl, pH 8.5, 0.2 mM EDTA, 500 μM polypeptide substrate (LSN-LYHQGKFLQTFCGSPLYRRR) (SEQ ID NO: 1), 10 mM magnesium acetate and 10 μM [γ-$^{33}$P]-ATP (intensity of which is about 500 cpm/pmol). After adding the mixed solution of Mg$^{2+}$ and ATP, the reaction started and the reaction solution was incubated at room temperature for 40 min. 3% phosphate buffer was added to stop the reaction. 10 μL of the reaction solution was filtered on a continuous filter P30, washed three times with 75 mM phosphate buffer, once with methanol, and 5 minutes each time. After drying, the value was read by scintillation counting method.

TABLE 1

Results of in vitro enzymatic activity determination of compounds of the present invention (IC$_{50}$)

| Compound NO. | Wee1 (IC$_{50}$ nM) |
|---|---|
| AZD1775 | 47 |
| Compound 1 | 29 |
| Compound 2 | 58 |
| Compound 3 | 42 |
| Compound 4 | 92 |
| Compound 6 | 46 |
| Compound 7 | 54 |
| Compound 8 | 93 |
| Compound 9 | 41 |
| Compound 10 | 49 |
| Compound 11 | 102 |
| Compound 12 | 59 |
| Compound 13 | 265 |
| Compound 14 | 43 |
| Compound 15 | 114 |
| Compound 16 | 60 |
| Compound 17 | 366 |
| Compound 18 | 29 |
| Compound 19 | 72 |
| Compound 20 | 173 |
| Compound 21 | 280 |
| Compound 22 | 16 |
| Compound 23 | 29 |
| Compound 24 | 57 |
| Compound 25 | 78 |
| Compound 26 | 30 |
| Compound 27 | 37 |
| Compound 28 | 79 |
| Compound 29 | 444 |
| Compound 30 | 67 |
| Compound 31 | 323 |
| Compound 32 | 37 |
| Compound 33 | 151 |
| Compound 34 | 116 |
| Compound 35 | 276 |
| Compound 36 | 35 |
| Compound 37 | 31 |
| Compound 38 | 48 |
| Compound 39 | 54 |
| Compound 40 | 35 |
| Compound 41 | 16 |
| Compound 42 | 221 |

Experimental Conclusion

The compounds of the present invention have good inhibitory effect on Wee1 kinase.

Experimental Example 2: In Vitro Permeability Test of the Compounds of the Present Invention The study used MDR1-MDCK II cells authorized by Piet Borst laboratory of the Netherlands Cancer Institute, which are a kind of Madin-Darby canine kidney cells transfected with human multi-drug resistance gene (MDR1). The cells can stably express the efflux transporter P glycoprotein (P-gp), so they are suitable for screening P-gp substrates or inhibitors, and predict that the compounds have high efflux barrier permeability such as duodenum, blood-brain barrier, hepatocyte nucleus and renal unit. We used the 5$^{th}$ to 35$^{th}$ generation MDR1-MDCK II cells for permeability study.

MDR1-MDCK II cells were cultured with α-MEM medium (α-Minimum Essential Media) under the conditions of 37±1° C., 5% CO$_2$ and saturated relative humidity. After that, the cells were inoculated in a BD Transwell-96-well plate with an inoculation density of 2.3×10$^5$ cells/cm$^2$, and then the cells were placed in a carbon dioxide incubator for 4-7 days and used for transport experiments. The preparation method of α-MEM medium was as follows: the liquid nutrient base was prepared by dissolving powder (α-MEM powder from Gibco, Cat #: 11900) in pure water, and L-glutamine and NaHCO$_3$ were added. 10% FBS (fetal bovine serum), 1% PS (dual antibiotic) and 1% NEAA were added to make it a complete medium when using. The ingredients of α-MEM medium are shown in Table 2.

TABLE 2

αMEM (1L ×) ingredients list
αMEM (1L ×) ingredients list

| Compound (1L ×) | Molecular weight. | Concentration (mM) | Dose (mg/L) |
|---|---|---|---|
| Medium powder | / | / | 1 package |
| L-glutamine | 146 | 2 | 292 |
| NaHCO$_3$ | 84 | 17.85 | 1500 |

AZD1775 (or the compounds of the present invention) and digoxin were administered at a concentration of 2 μM, bi-directionally (A B and B A directions), and duplicated in two wells. Fenoterol and propranolol were tested at a concentration of 2 μM, administered unidirectionally (A-B direction), and duplicated in two wells.

The solution to be used was pre-incubated in a 37±1° C. water bath for 30 minutes. The dosing solution and the receiving solution were added to the corresponding well positions of the cell plate (75 and 250 μL for each top and bottom well, respectively) to start the bidirectional transport experiment. After loading, the cell plates were placed in an incubator at 37±1° C., 5% CO$_2$ and saturated relative humidity for 150 minutes. Samples collection information is shown in table 3.

TABLE 3

Samples collection information

| Sample | Sample volume per well (μL) | Stop solution volume (μL) | Transport buffer volume (μL) |
|---|---|---|---|
| A-B administration side | 50 | 250 | 100 |
| A-B reception side | 150 | 250 | 0 |
| B-A administration side | 50 | 250 | 100 |
| B-A reception side | 50 | 250 | 100 |
| T$_0$ | 50 | 250 | 100 |

Note: T$^0$ represents the initial dosing solution sample.

After vortexing, all samples were centrifuged at 3,220 g for 10 minutes. An appropriate volume of supernatant was transferred to the sample analysis plate, and analyzed by LC/MS/MS. If samples were not analyzed immediately after sealing, they were store at 2-8° C.

After the transport experiment was completed, the integrity of MDR1-MDCK II cells was tested using Lucifer Yellow Rejection Assay. After incubating the fluorescent yellow solution for 30 minutes, the fluorescent yellow samples were collected, and the relative fluorescence unit (RFU) of the fluorescent yellow in the sample was detected at 425/528 nm (excitation/emission) by the 2e plate reader.

Semi-quantitative analysis was used for the test products AZD1775 (or the compound of the present invention), the control products fenoterol, propranolol and digoxin. The ratio of the peak area of the analyte to the internal standard was used as the concentration of the reference substance. The experimental results are shown in Table 4:

TABLE 4

| Penetration rate (10$^{-6}$ cm/s) | | | |
|---|---|---|---|
| | AZD1775 | Compound 1 | Compound 2 |
| A to B | 2.83 | 4.55 | 4.76 |
| B to A | 29.3 | 17.38 | 19.94 |
| Efflux ratio | 10.37 | 3.82 | 4.19 |

Experimental Conclusion

The permeability properties of the compounds of the present invention are greatly improved compared to AZD1775, which is beneficial to the utilization of drugs by organisms.

Experimental Example 3: Compound Pharmacokinetic Evaluation

The purpose of this experiment was to study the pharmacokinetics of AZD1775 (or the compounds of the present invention) in the plasma of female Balb/c Nude mice after a single intravenous, single oral administration.

Twelve mice (provided by Lingchang Biotech) were randomly divided into two groups, 6 females in each group, and samples were collected by cross blood collection. All animals in the intravenous group were given 1 mg/kg of AZD1775 (or compounds of the present invention) by intravenous injection. The formulation was a clear solution of 5% HP-betaCD (Kunshan Ruisk Chemical Materials Co., Ltd.) containing 0.2 mg/mL AZD1775 (or the compounds of the present invention). Animals in the oral group were given AZD1775 (or the compounds of the present invention) at 10 mg/kg by gavage. The formulation was a uniform suspension of 0.5% methylcellulose containing 1 mg/mL AZD1775 (or the compounds of the present invention). In the intravenous group, plasma samples were collected at 9 time points of 5 minutes, 15 minutes, 30 minutes, 1 hour, 2 hours, 4 hours, 6 hours, 8 hours, and 24 hours after administration; in the oral group, plasma samples were collected at 8 time points of 15 minutes, 30 minutes, 1 hour, 2 hours, 4 hours, 6 hours, 8 hours, and 24 hours after administration. Samples were analyzed by LC-MS/MS to obtain plasma concentration data of AZD1775 (or the compounds of the present invention), and pharmacokinetic parameters were calculated, such as peak concentration, peak time, clearance rate, half-life, area under the concentration-time curve, bioavailability, etc. The experimental results are shown in Table 5:

TABLE 5

Pharmacokinetic test results

| Test product (compounds prepared in each Example) | Clearance rate (mL/min/kg) | Half-life T$_{1/2}$ (h) | Concentration integral AUC (nM · hr) | Bioavailability F (%) |
|---|---|---|---|---|
| AZD1775 | 85.7 | 0.252 | 1200 | 31 |
| Compound 1 | 33.5 | 1.69 | 6037 | 62.4 |
| Compound 2 | 46.7 | 1.3 | 5166 | 74.6 |

Conclusion: Compared with AZD1775, the compounds of the present invention significantly improve multiple indexes of pharmacokinetics in mice, among which the in vivo clearance rate, half-life, in vivo concentration integral and bioavailability have obvious advantages.

Experimental Example 4: In Vivo Study (1) In vivo pharmacodynamic study of the compounds on human colon cancer LoVo cell subcutaneous xenograft tumor BALB/c nude mouse model Experimental method: The selected experimental animal (provided by Shanghai Xipu'er-bikai Experimental Animal Co., Ltd.) were BALB/c nude mice, 6-8 weeks old, weighing 18-22 grams.

Human colon cancer LoVo cells were cultured in monolayer in vitro. The culture conditions were Ham's F-12 medium containing 10% fetal bovine serum, 100 U/mL penicillin, 100 µg/mL streptomycin and 2 mM glutamine, 37° C., 5% $CO_2$ culture. Conventional digestion treatment with trypsin-EDTA was performed twice a week for passaging. When the cell saturation was 80%-90%, the cells were collected, counted, and inoculated. 0.1 mL ($10 \times 10^6$) LoVo cells were subcutaneously inoculated into the right back of each nude mouse. When the average tumor volume reached 213 mm$^3$, they were divided into groups and the drug administration was started. Dosage: 40 mg/kg twice daily. The experimental index is to investigate whether the tumor growth is inhibited, delayed or cured. The diameter of the tumor was measured with vernier calipers twice a week. The calculation formula of tumor volume is: $V=0.5 \times a \times b^2$, a and b represent the long and short diameters of the tumor, respectively.

The antitumor efficacy of the compound was evaluated by TGI (%) or relative tumor proliferation rate T/C (%). TGI (%) reflects the tumor growth inhibition rate. Calculation of TGI (%): TGI (%)=[(1−(average tumor volume at the end of administration in a certain treatment group-average tumor volume at the beginning of administration in this treatment group))/(average tumor volume of the solvent control group at the end of treatment-average tumor volume of the solvent control group at the beginning of treatment)]×100%.

After the final administration for 16 days, the experimental results are as follows:

TABLE 6

In vivo drug efficacy results of mice tumors

| Compound | TGI (%) |
|---|---|
| AZD1775 | 26.73 |
| Compound 1 | 84.74 |
| Compound 2 | 48.67 |

Conclusion: Compared with AZD1775, the compounds of the present invention significantly increase the inhibitory effect on tumors in mice, and the chirality of the compound has an unexpected effect on the drug efficacy in vivo.

(2) In vivo pharmacodynamic study of the compound on human pancreatic cancer BxPC-3 BALB/c nude mouse subcutaneously transplanted tumor model Experimental method: The selected experimental animal was BALB/c nude nude mice, 6-8 weeks old, weighing 18-22 grams.

The 10$^{th}$ generation of BxPC-3 cells were cultured in monolayer in vitro. The culture conditions were RPMI 1640 medium (manufacturer: gibco, article number: 22400-089) containing 10% fetal bovine serum, 100 U/mL penicillin and 100 µg/mL streptomycin, 37° C. 5% $CO_2$ culture, passage was performed for 4 times. The passaging method was conventional digestion treatment with trypsin-EDTA twice a week. When the cell saturation reached 80%-90%, the cells were digested with trypsin-EDTA, counted, and resuspended in PBS at a density of $5 \times 10^7$ cells/mL. Each animal was inoculated with 0.1 mL ($5 \times 10^6$) BxPC-3 cells in the right back. When the average tumor volume reached 153 mm$^3$, they were randomly divided into groups according to the tumor volume and the drug administration was started. Dosage: 25 mg/kg, once a day.

The experimental index is to investigate whether the tumor growth is inhibited, delayed or cured. The diameter of the tumor was measured with vernier calipers twice a week. The antitumor efficacy of the compound was evaluated by TGI (%) or relative tumor proliferation rate T/C (%). TGI (%) reflects the tumor growth inhibition rate. Calculation of TGI (%): TGI (%)=[(1−(average tumor volume at the end of administration in a certain treatment group-average tumor volume at the beginning of administration in this treatment group))/(average tumor volume of the solvent control group at the end of treatment-average tumor volume of the solvent control group at the beginning of treatment)]×100%.

After the final administration for 27 days, the experimental results are as follows:

TABLE 7

In vivo drug efficacy results of mice tumors

| Compound | TGI (%) |
|---|---|
| AZD1775 | 24.3 |
| Compound 1 | 73.3 |

Conclusion: It can be seen from Table 7 that the compound of the present invention significantly increases the inhibitory effect on mice body tumors compared with AZD1775.

(3) In vivo anti-tumor efficacy of the compounds on CT26 mouse colon cancer animal transplanted tumor model Experimental method: The selected experimental animal was BALB/c nude mice, 7 weeks old, weighing 16-20 grams, female.

Cells: Mouse colon cancer CT26 cells (the Cell Bank of Typical Culture Preservation Committee of the Chinese Academy of Sciences) were cultured in monolayer in vitro. The culture conditions were RPMI-1640 medium containing 10% fetal bovine serum and 37° C. 5% $CO_2$ incubator. Conventional digestion treatment with trypsin-EDTA was performed twice a week for passaging. When the cells were in the exponential growth phase and the saturation was 80%-90%, the cells were collected, counted, and inoculated. 0.1 mL DPBS (containing $3 \times 10^5$ CT26 cells) was subcutaneously inoculated into the right back of each mouse. When the average tumor volume reached 50-70 mm$^3$, randomized administration was performed according to tumor volume. Dosage: 30 mg/kg twice daily.

The experimental index is to investigate whether the tumor growth is inhibited, delayed or cured. The diameter of the tumor was measured with vernier calipers twice a week. The antitumor efficacy of the compound was evaluated by TGI (%) or relative tumor proliferation rate T/C (%). TGI (%) reflects the tumor growth inhibition rate. Calculation of TGI (%): TGI (%)=[(1−(average tumor volume at the end of administration in a certain treatment group-average tumor volume at the beginning of administration in this treatment group))/(average tumor volume of the solvent control group at the end of treatment-average tumor volume of the solvent control group at the beginning of treatment)]×100%.

After the final administration for 18 days, the experimental results are as follows:

TABLE 8

In vivo drug efficacy results of mice tumors

| Compound | TGI (%) |
|---|---|
| AZD1775 | 66.43 |
| Compound 1 | 93.38 |

Conclusion: It can be seen from Table 8 that the compound of the present invention significantly increases the inhibitory effect on mice body tumors compared with AZD1775.

What is claimed is:

1. A compound represented by formula (II), an (R)-isomer thereof, an (S)-isomer or a pharmaceutically acceptable salt thereof,

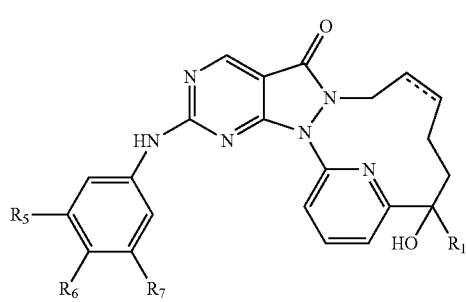

(II)

wherein,

⇜ is a single bond or a double bond;

$R_1$ is selected from H and $C_{1-3}$ alkyl, wherein the $C_{1-3}$ alkyl is optionally substituted by R, and the number of R is 1, 2, or 3;

$R_5$ is selected from H and $C_{1-3}$ alkyl, wherein the $C_{1-3}$ alkyl is optionally substituted by R, and the number of R is 1, 2, or 3;

$R_6$ is selected from $R_{61}$,

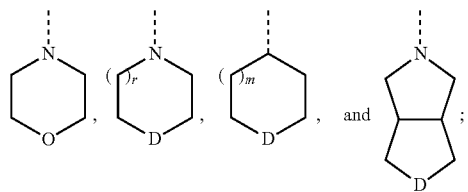

r is 1 or 2;
m is 1 or 2;

D is selected from $-N(R_2)-$, $N^+(O^-)(R_2)-$, and $-C(R_3)(R_4)-$;

$R_2$ is selected from H and $C_{1-3}$ alkyl, wherein the $C_{1-3}$ alkyl is optionally substituted by R, and the number of R is 1, 2, or 3;

$R_3$ and $R_4$ are independently selected from H, F, Cl, Br, I, OH, $NH_2$, and $C_{1-3}$ alkyl wherein the $NH_2$ and the $C_{1-3}$ alkyl are optionally substituted by R, and the number of R is 1, 2, or 3;

alternatively, $R_3$ and $R_4$ together with the carbon atom to which they are attached form a 5-7 membered cycloalkyl or a 5-7 membered heterocycloalkyl, wherein the 5-7 membered cycloalkyl and the 5-7 membered heterocycloalkyl are optionally substituted by R, and the number of R is 1, 2, or 3;

$R_{61}$ is selected from H, F, Cl, Br, I, OH, $NH_2$, $C_{1-3}$ alkoxy, and $-O-C_{3-6}$ cycloalkyl, wherein the $C_{1-3}$ alkoxy and the $-O-C_{3-6}$ cycloalkyl are optionally substituted by R, and the number of R is 1, 2, or 3;

$R_7$ is selected from H, F, Cl, Br, I, OH, $NH_2$, $C_{1-3}$ alkyl, $C_{1-3}$ alkoxy, and 5-6 membered heterocycloalkyl, wherein the $C_{1-3}$ alkyl, $C_{1-3}$ alkoxy, and 5-6 membered heterocycloalkyl are optionally substituted by R, and the number of R is 1, 2, or 3;

alternatively, $R_6$ and $R_7$ together with the ring atoms to which they are attached form ring A, and the moiety

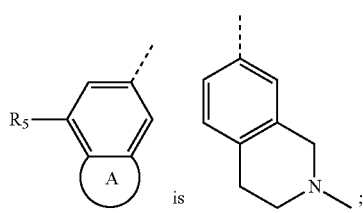 is and
R is independently selected from F, Cl, Br, I, OH, NH$_2$, C$_{1-3}$ alkyl, C$_{1-3}$ alkoxy, and C$_{1-3}$ alkylamino, the C$_{1-3}$ alkylamino being a C$_{1-3}$ alkyl group connected to a part of the molecule via an amino; and the 5-7 membered heterocycloalkyl contains 1, 2, 3 or 4 heteroatoms or heteroatom groups independently selected from —NH—, —S—, and N.

2. The compound the (R)-isomer thereof, the (S)-isomer thereof, or the pharmaceutically acceptable salt thereof as defined in claim 1, wherein the R is independently selected from F, Cl, Br, I, OH, NH$_2$, CH$_3$, Et, —OCH$_3$, and

3. The compound, the (R)-isomer thereof, the (S)-isomer thereof, or the pharmaceutically acceptable salt thereof as defined in claim 1, wherein the R$_1$ is selected from H, CH$_3$, and Et;

or, the R$_2$ is selected from H, CH$_3$, and Et;

or, the R$_3$ and R$_4$ are independently selected from H, F, Cl, Br, I, OH, NH$_2$, —NH(CH$_3$), —N(CH$_3$)$_2$, CH$_3$, and Et;

or, the R$_5$ is selected from H, CH$_3$, and Et, wherein the CH$_3$ and Et are optionally substituted by R, and the number of R is 1, 2, or 3;

or, the R$_{61}$ is selected from H, F, Cl, Br, I, OH, NH$_2$, —OCH$_3$,

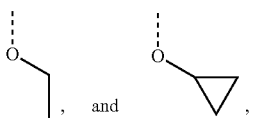

wherein the —OCH$_3$,

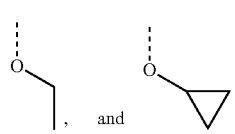

are optionally substituted by R, and the number of R is 1, 2, or 3;

or, the R$_6$ is selected from R$_{61}$,

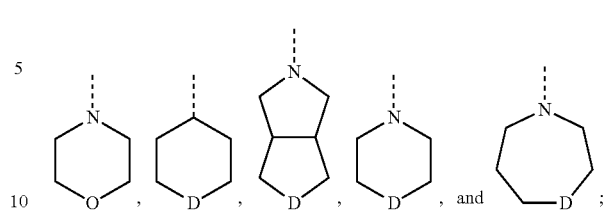

or, the R$_7$ is selected from H, F, Cl, Br, I, OH, NH$_2$, CH$_3$, —OCH$_3$,

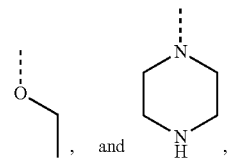

wherein the CH$_3$, —OCH$_3$,

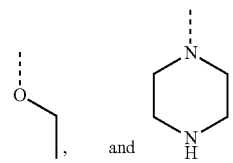

are optionally substituted by R, and the number of R is 1, 2, or 3;

or, the moiety

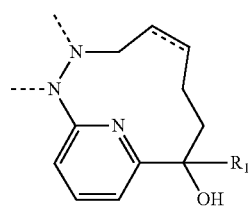

is selected from

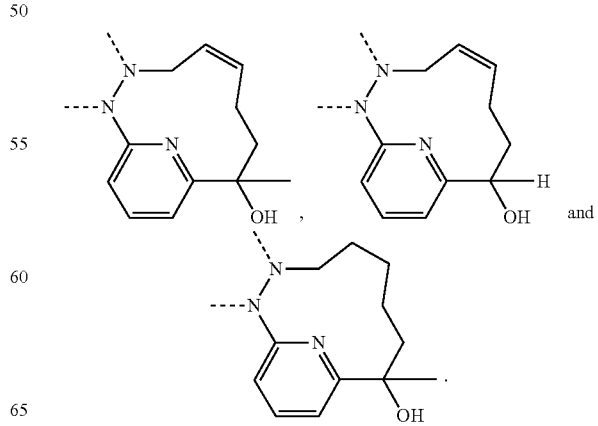

4. The compound, the (R)-isomer thereof, the (S)-isomer thereof, or the pharmaceutically acceptable salt thereof as defined in claim 3, wherein the $R_3$ is selected from H, F, Cl, Br, I, OH, $NH_2$, —$NH(CH_3)$, —$NH(CH_3)_2$, $CH_3$, and Et.

5. The compound, the (R)-isomer thereof, the (S)-isomer thereof, or the pharmaceutically acceptable salt thereof as defined in claim 3, wherein the $R_4$ is selected from H, F, Cl, Br, I, OH, $CH_3$, and Et.

6. The compound, the (R)-isomer thereof, the (S)-isomer thereof, or the pharmaceutically acceptable salt thereof as defined in claim 3, wherein the $R_5$ is selected from H, $CH_3$, and —$CH_2OH$.

7. The compound, the (R)-isomer thereof, the (S)-isomer thereof, or the pharmaceutically acceptable salt thereof as defined in claim 3, wherein the $R_{61}$ is selected from H, F, Cl, Br, I, OH, $NH_2$, —$OCH_3$,

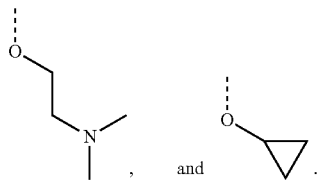
and .

8. The compound, the (R)-isomer thereof, the (S)-isomer thereof, or the pharmaceutically acceptable salt thereof as defined in claim 3, wherein the $R_6$ is selected from $R_{61}$,

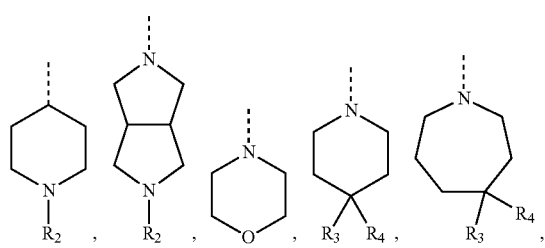

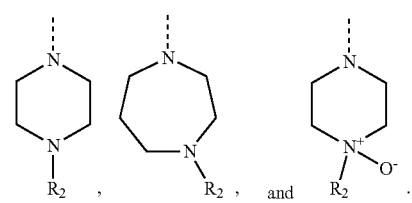

9. The compound, the (R)-isomer thereof, the (S)-isomer thereof, or the pharmaceutically acceptable salt thereof as defined in claim 1, wherein the $R_3$ and $R_4$ together with the carbon atom to which they are attached form a 5-7 membered cycloalkyl or 5-7 membered heterocycloalkyl, and the 5-7 membered cycloalkyl or 5-7 membered heterocycloalkyl is optionally substituted by R, and the number of R is 1, 2, or 3;

then the moiety

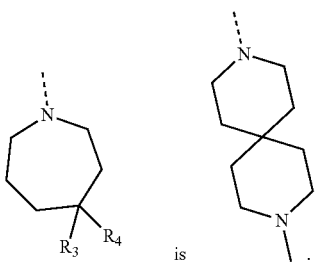
is .

10. The compound, the (R)-isomer thereof, the (S)-isomer thereof, or the pharmaceutically acceptable salt thereof as defined in claim 1, wherein the $R_6$ is selected from H, F, Cl, Br, I, OH, $NH_2$, —$OCH_3$,

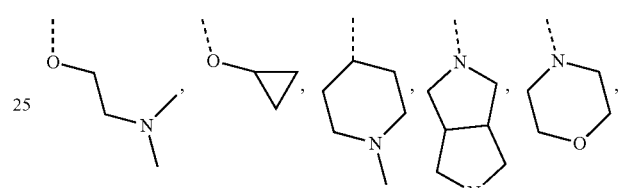

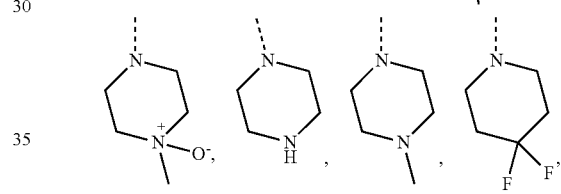

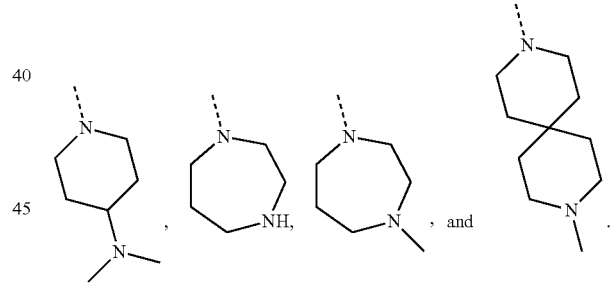

11. The compound, the (R)-isomer thereof, the (S)-isomer thereof, or the pharmaceutically acceptable salt thereof as defined in claim 3, wherein the $R_7$ is selected from H, F, Cl, Br, I, OH, $NH_2$, —$OCH_3$,

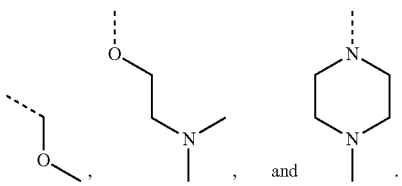

12. The compound, the (R)-isomer thereof, the (S)-isomer thereof, or the pharmaceutically acceptable salt thereof as defined in claim 1, which is selected from (II-1)
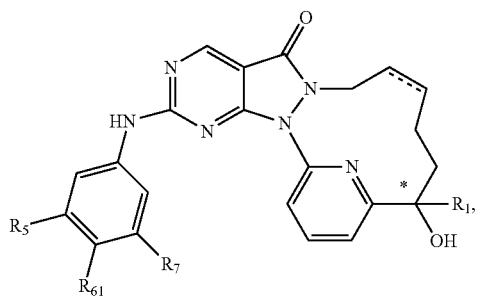

(II-2)
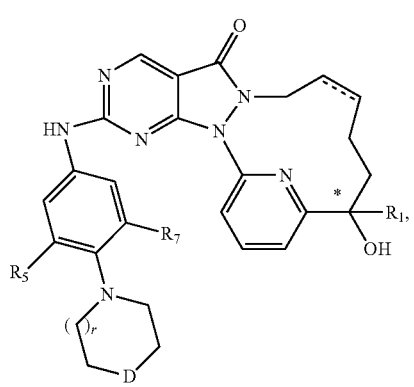

(II-3)
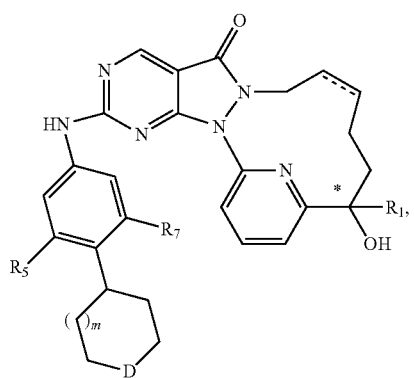

(II-4)
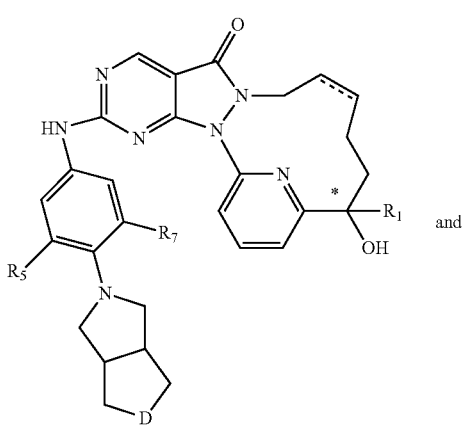

and (II-5)
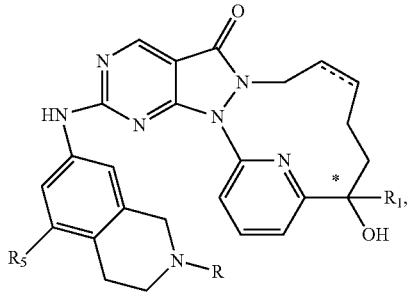

wherein,

D is selected from —N(R$_2$)—, —N$^+$(Q$^-$)(R$_2$)—, and —C(R$_3$)(R$_4$)—;

r, m, R$_1$, R$_2$, R$_3$, R$_4$, R$_5$, R$_{61}$, and R$_7$ are as defined in claim 1;

the carbon atom with "*" is a chiral carbon atom and exists in the form of (R) or (S) single enantiomer or enriched in one enantiomer.

13. The compound, the (R)-isomer thereof, the (S)-isomer thereof, or the pharmaceutically acceptable salt thereof as defined in claim 12, which is selected from (I)
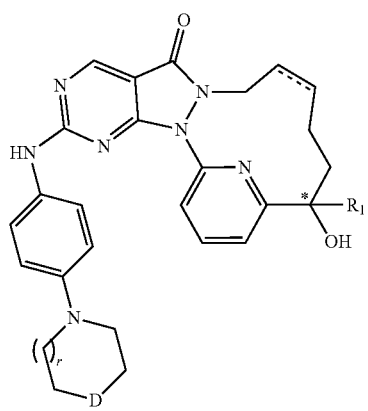

wherein,

D is selected from —N(R$_2$)—, —N$^+$(Q$^-$)(R$_2$)—, and —C(R$_3$)(R$_4$)—;

r, R$_1$, R$_2$, R$_3$, and R$_4$ are as defined in claim 12;

the carbon atom with "*" is a chiral carbon atom and exists in the form of (R) or (S) single enantiomer or enriched in one enantiomer.

14. The compound, the (R)-isomer thereof, the (S)-isomer thereof, or the pharmaceutically acceptable salt thereof as defined in claim 13, which is selected from (I-1)

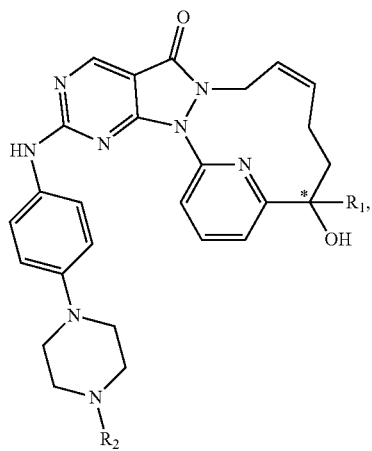

(I-2)

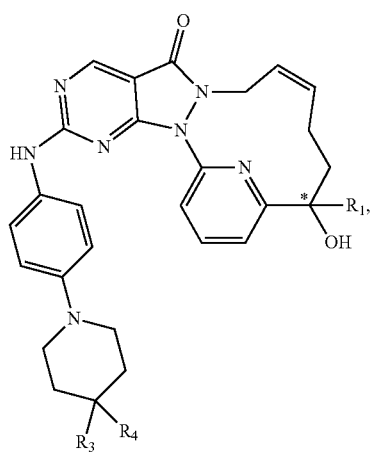

(I-3)

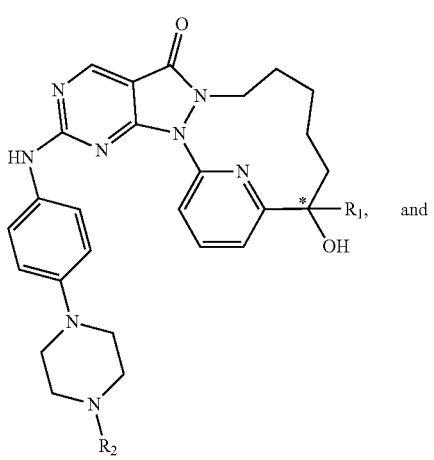

and (I-4)

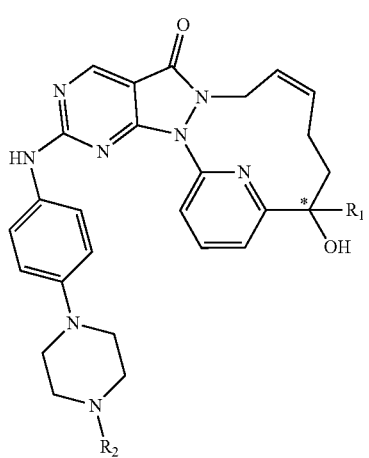

wherein $R_1$, $R_2$, $R_3$, and $R_4$ are as defined in claim 13;

the carbon atom with "*" is a chiral carbon atom and exists in the form of (R) or (S) single enantiomer or enriched in one enantiomer.

15. A method for treating tumors in a subject in need thereof, comprising: administering an effective amount of the compound or the pharmaceutically acceptable salt thereof as defined in claim 1 in a subject in need thereof.

16. A compound as shown below, an (R)-isomer thereof, an (S)-isomer thereof, or a pharmaceutically acceptable salt thereof, which is selected from

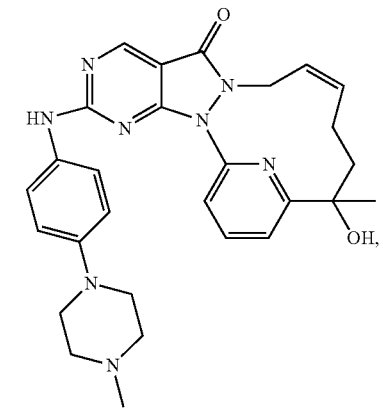

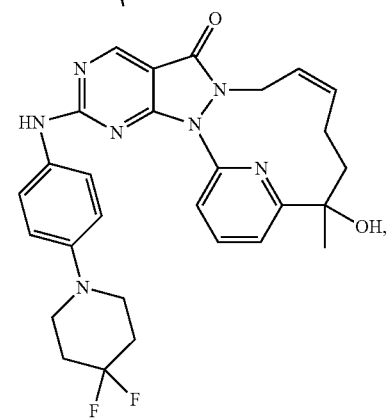

125
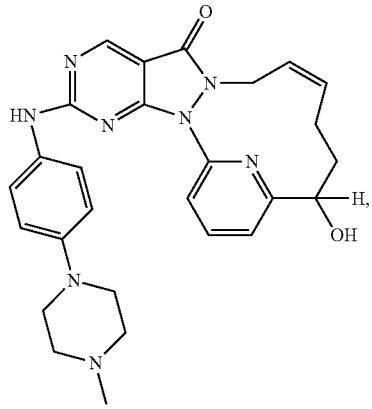
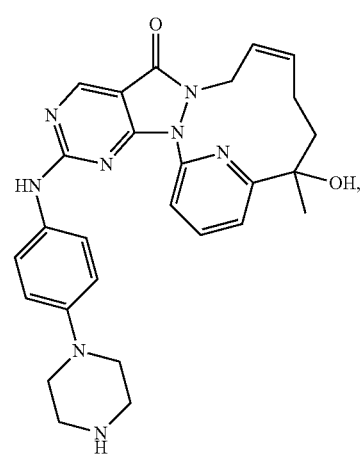
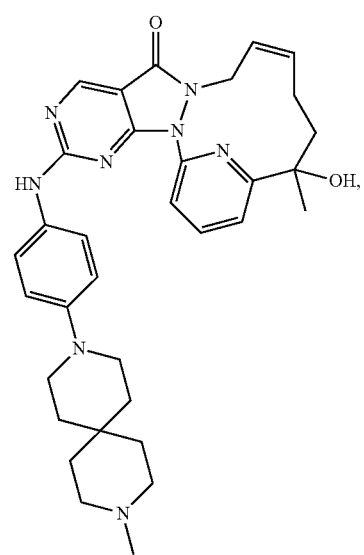
126
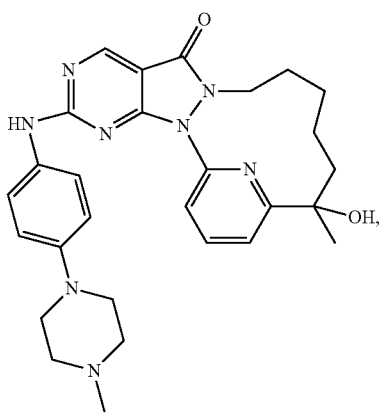
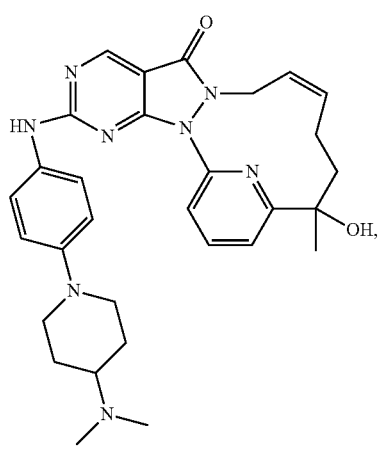
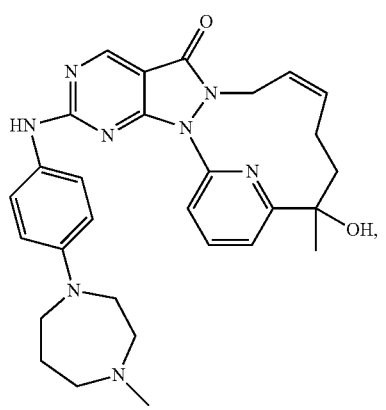
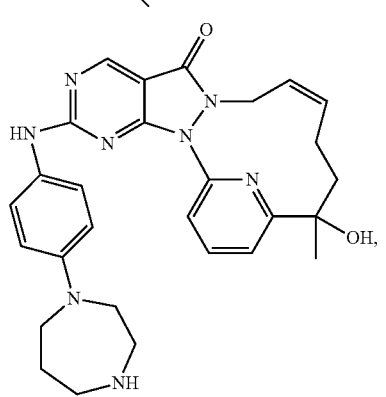

-continued
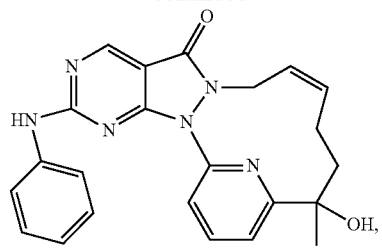
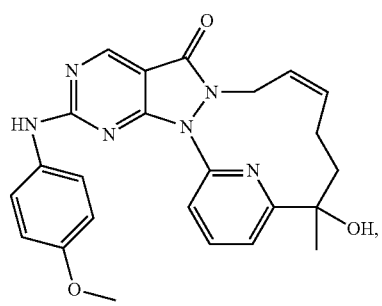
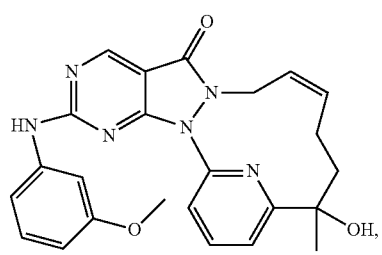
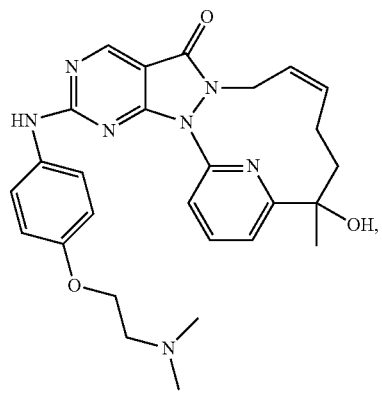
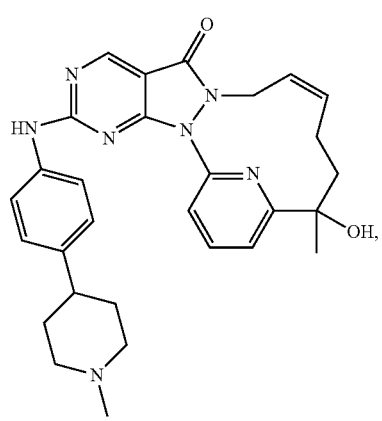
-continued
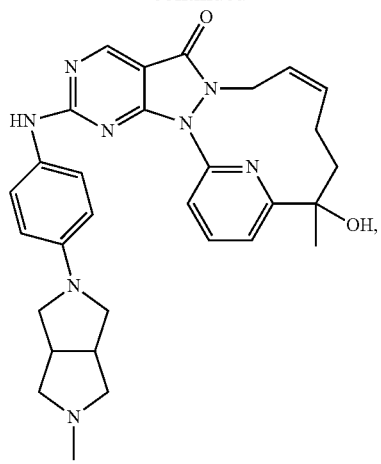
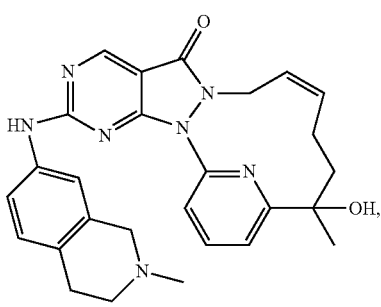
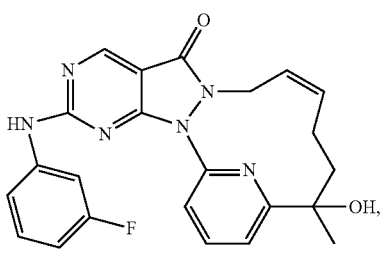
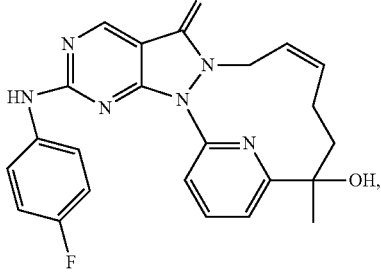
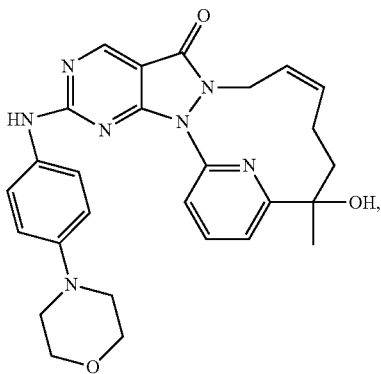

129
-continued
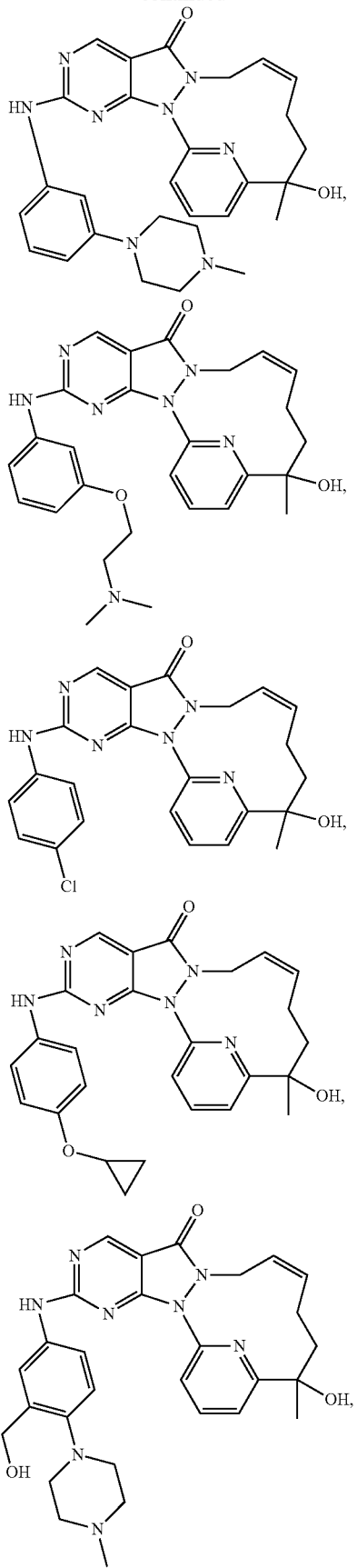
130
-continued
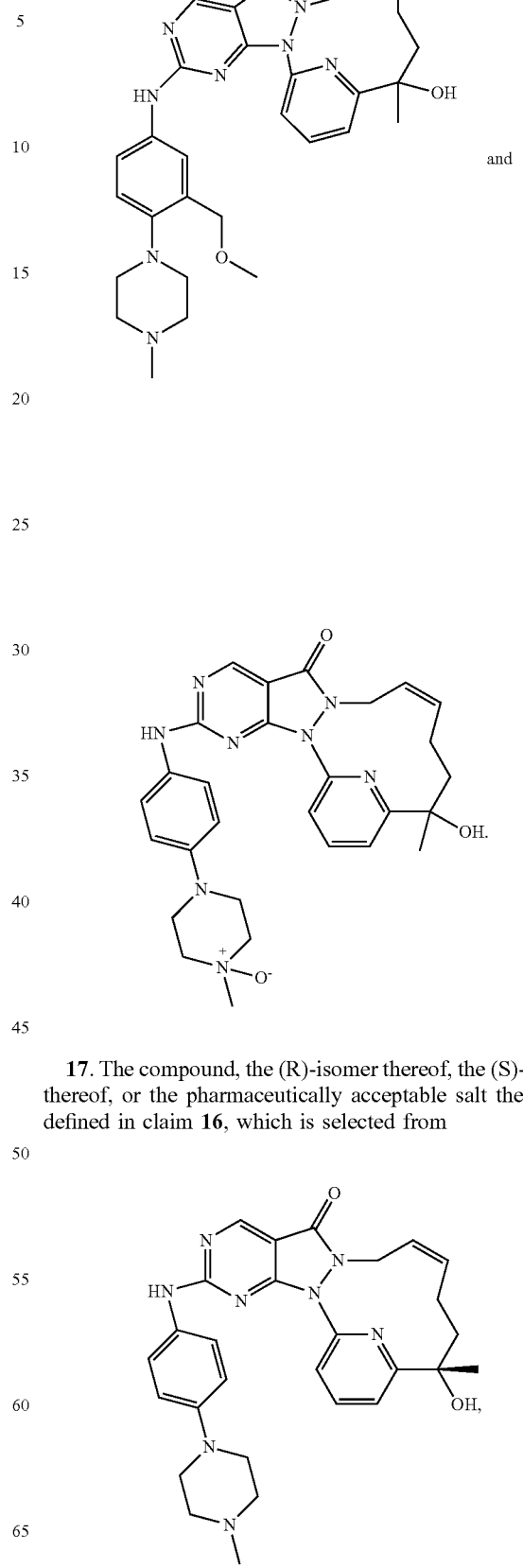
and
17. The compound, the (R)-isomer thereof, the (S)-isomer thereof, or the pharmaceutically acceptable salt thereof as defined in claim 16, which is selected from 131
-continued
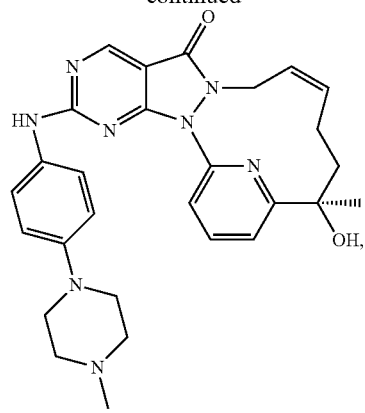
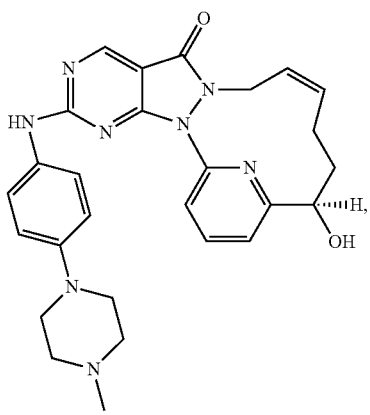
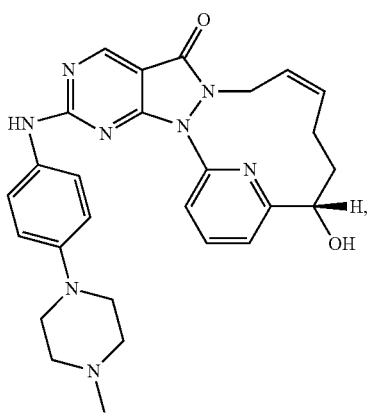
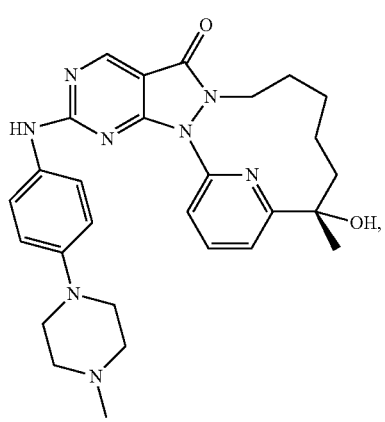
132
-continued
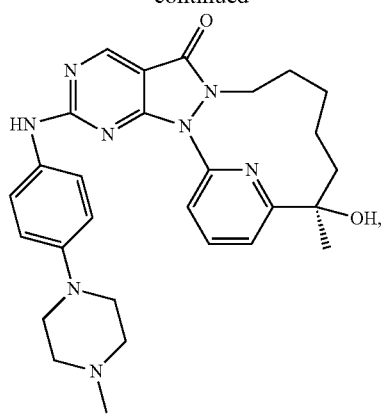
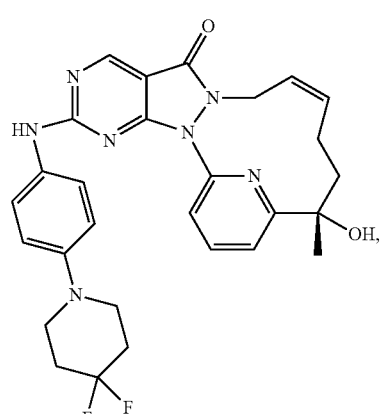
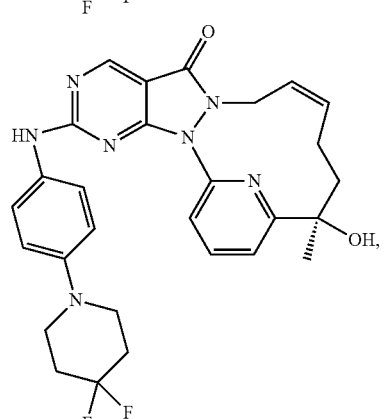
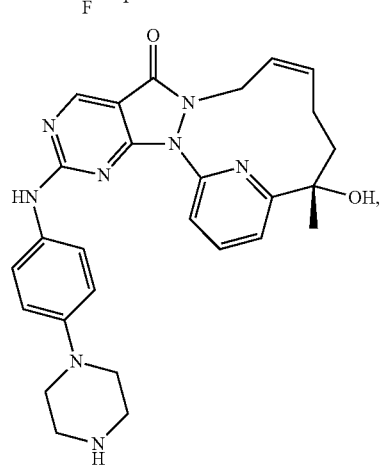

133
-continued
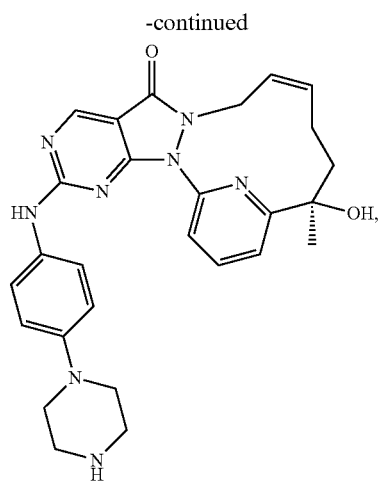
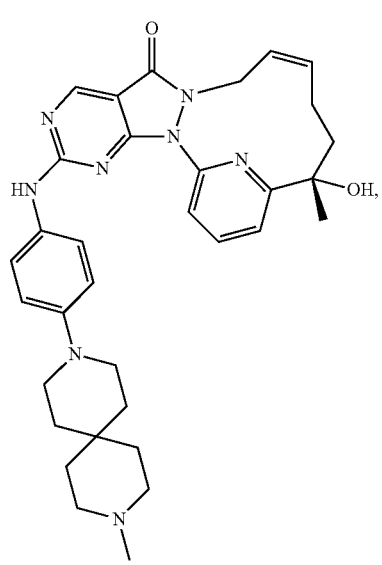
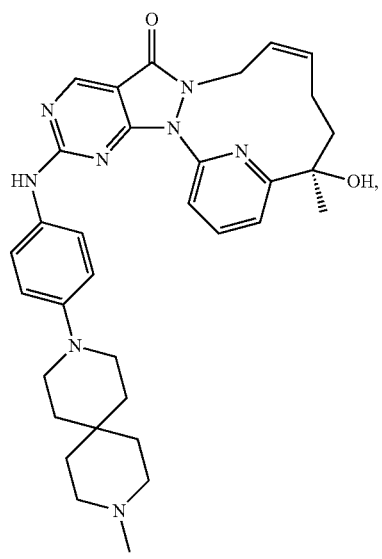
134
-continued
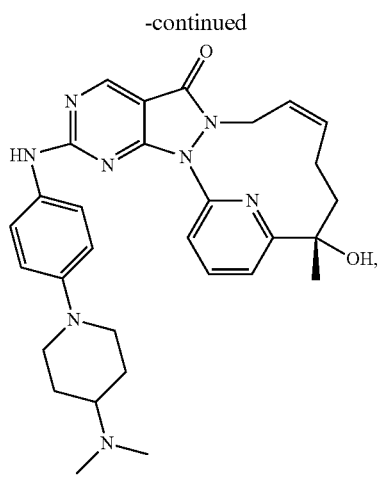
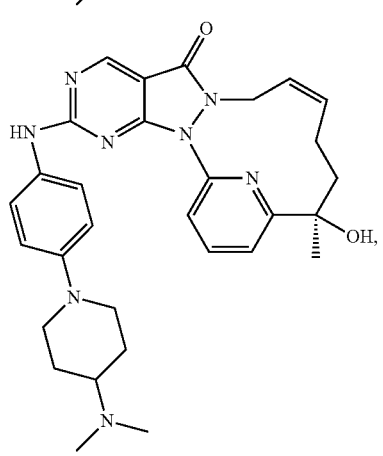
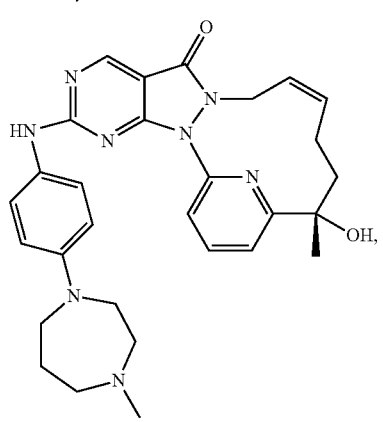
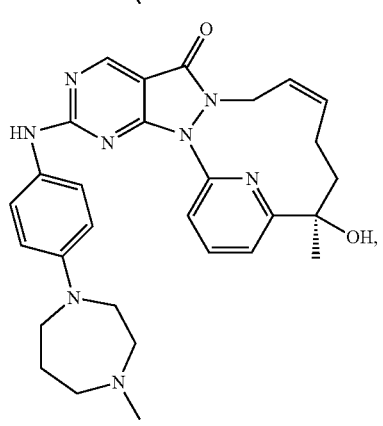

135
-continued
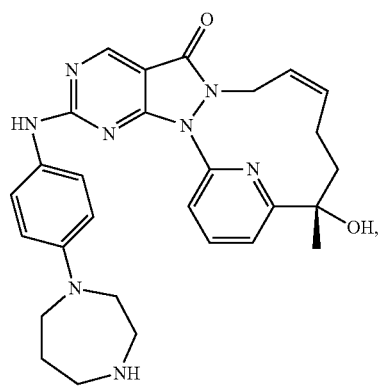
136
-continued
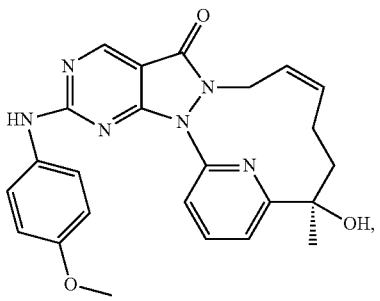
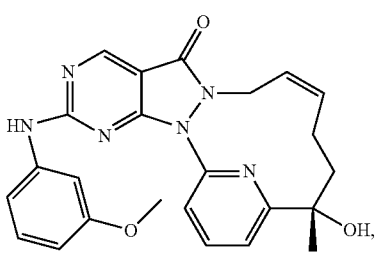
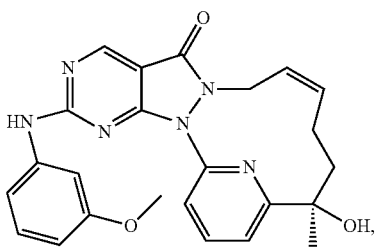
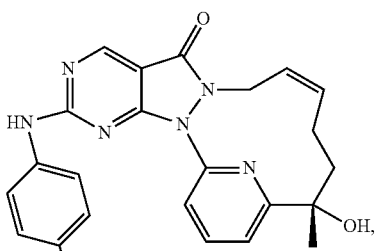
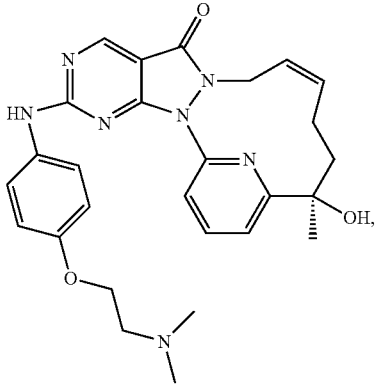

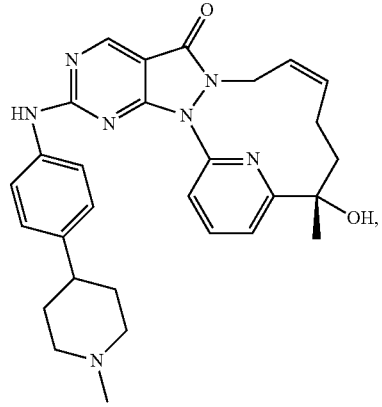
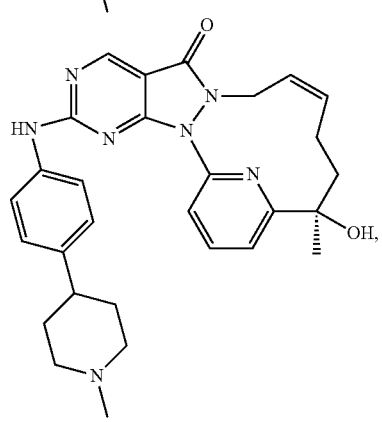
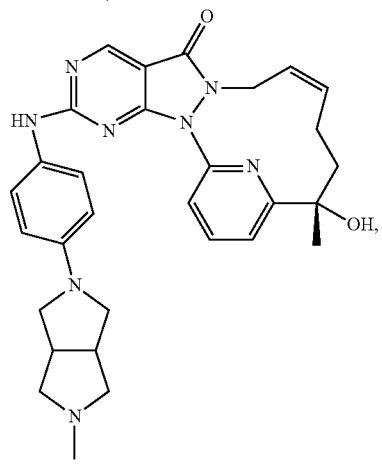
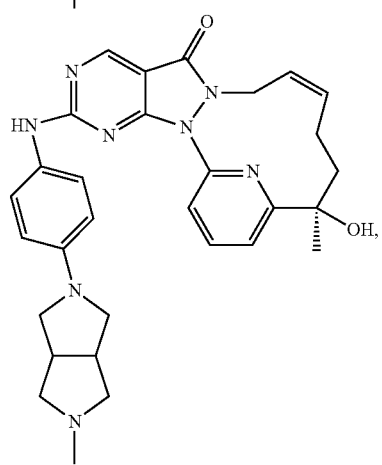
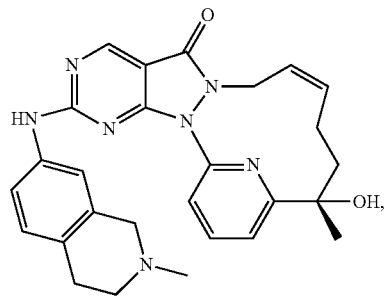
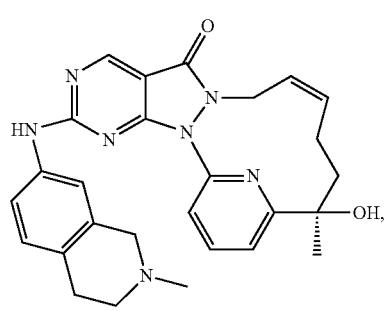
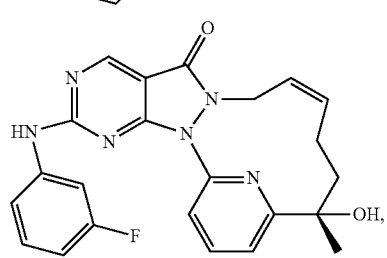
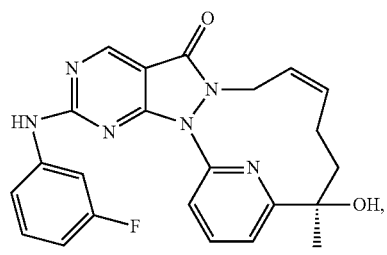
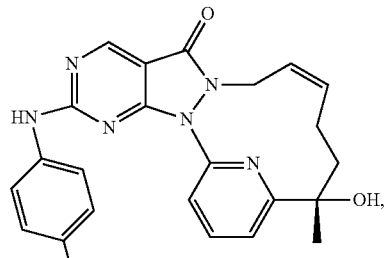
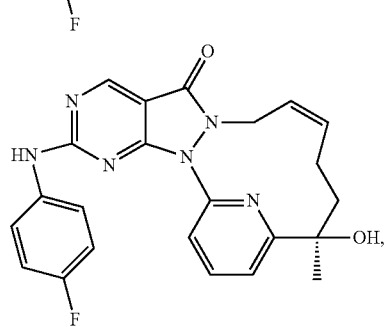

139
-continued
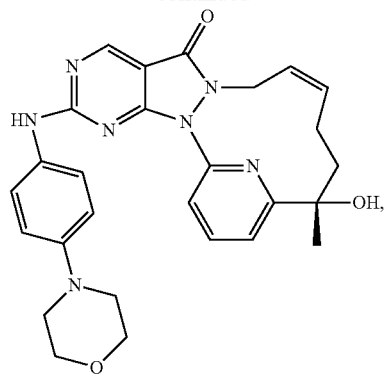
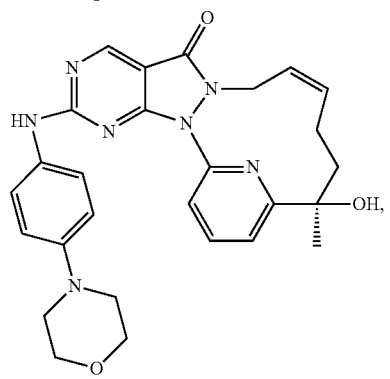
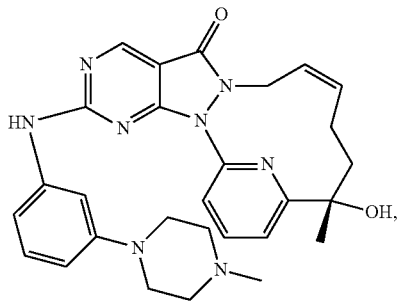
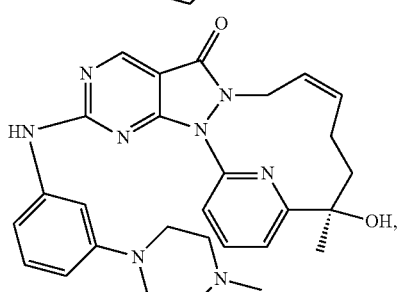
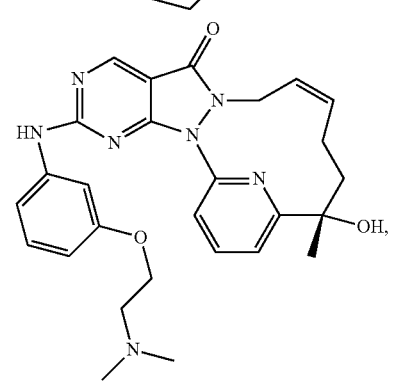
140
-continued
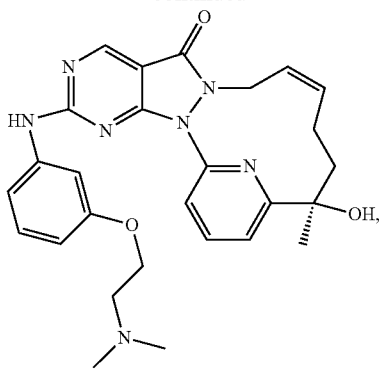
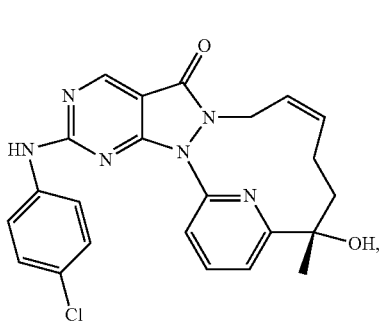
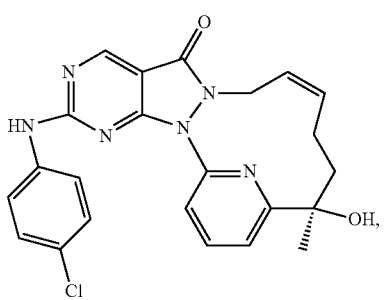
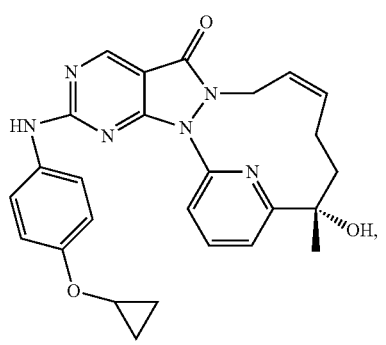
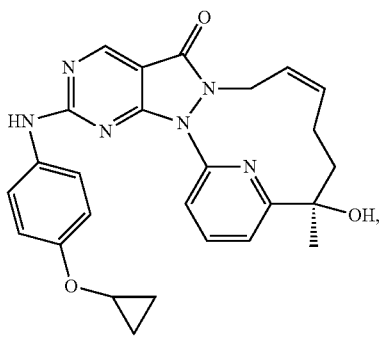

-continued

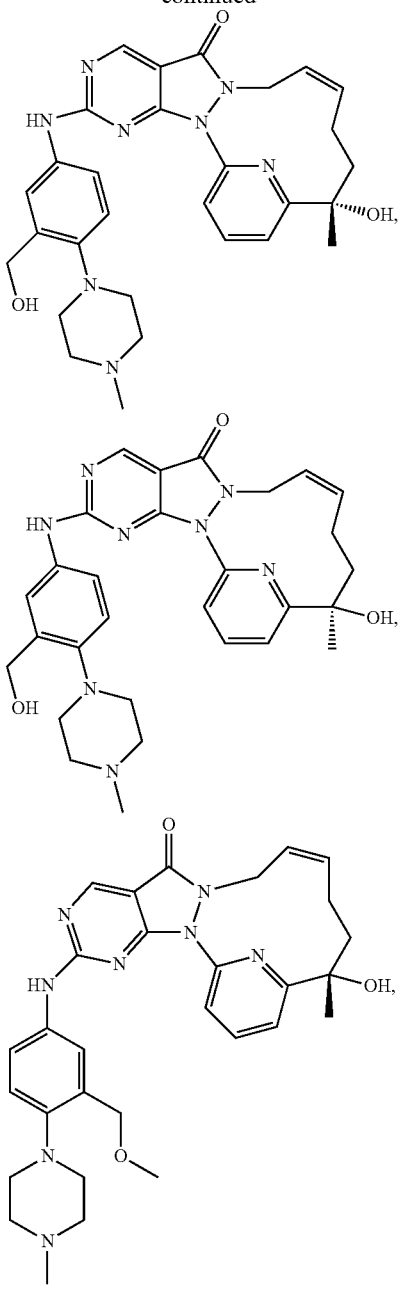

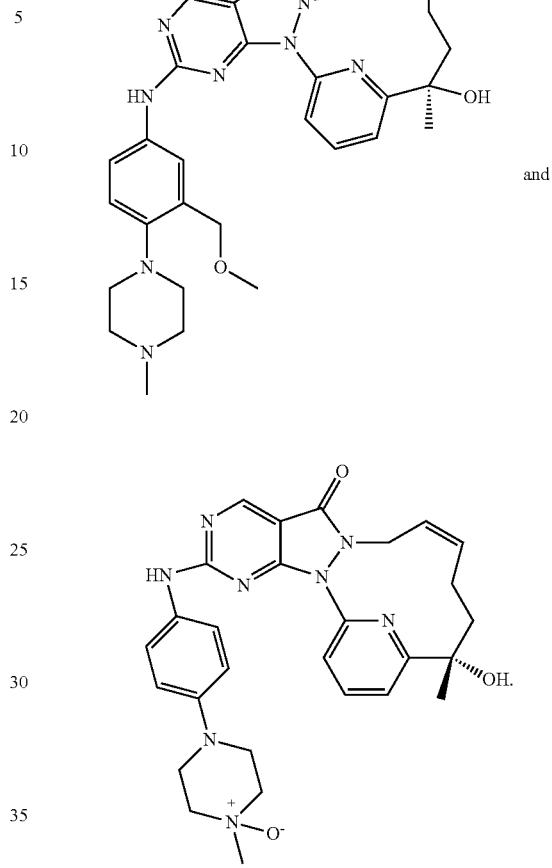

18. A method for treating tumors in a subject in need thereof, comprising: administering an effective amount of the compound or the pharmaceutically acceptable salt thereof as defined in claim 16 in a subject in need thereof.

19. The method for treating tumors in a subject in need thereof as defined in claim 15, wherein the tumors are solid tumors.

20. The method for treating tumors in a subject in need thereof as defined in claim 18, wherein the tumors are solid tumors.

* * * * *